United States Patent
Zatloukal et al.

(10) Patent No.: US 10,662,194 B2
(45) Date of Patent: May 26, 2020

(54) SUBSTITUTED 6-ANILINO-9-HETEROCYCLYLPURINE DERIVATIVES FOR INHIBITION OF PLANT STRESS

(71) Applicant: UNIVERZITA PALACKEHO V OLOMOUCI, Olomouc (CZ)

(72) Inventors: Marek Zatloukal, Sumperk (CZ); Lucie Plihalova, Olomouc (CZ); Jana Klaskova, Olomouc (CZ); Lukas Spichal, Olomouc (CZ); Radoslav Koprna, Olomouc (CZ); Karel Dolezal, Hlubocky (CZ); Miroslav Strnad, Olomouc (CZ)

(73) Assignee: UNIVERZITA PALACKEHO V OLOMOUCI, Olomouc (CZ)

(*) Notice: Subject to any disclaimer, the term of this patent is extended or adjusted under 35 U.S.C. 154(b) by 39 days.

(21) Appl. No.: 15/535,347

(22) PCT Filed: Dec. 9, 2015

(86) PCT No.: PCT/CZ2015/050014
§ 371 (c)(1),
(2) Date: Jun. 12, 2017

(87) PCT Pub. No.: WO2016/095881
PCT Pub. Date: Jun. 23, 2016

(65) Prior Publication Data
US 2017/0342072 A1    Nov. 30, 2017

(30) Foreign Application Priority Data
Dec. 15, 2014   (CZ) .................. PV 2014-907

(51) Int. Cl.
C07D 473/16    (2006.01)
A01N 43/90    (2006.01)
C07D 473/34    (2006.01)

(52) U.S. Cl.
CPC .......... *C07D 473/16* (2013.01); *A01N 43/90* (2013.01); *C07D 473/34* (2013.01)

(58) Field of Classification Search
None
See application file for complete search history.

(56) References Cited

U.S. PATENT DOCUMENTS

| | | | | | |
|---|---|---|---|---|---|
| 3,983,104 | A | * | 9/1976 | Vorbruggen | C07H 19/16 536/27.61 |
| 5,663,154 | A | * | 9/1997 | Burns | C07H 19/16 514/45 |

FOREIGN PATENT DOCUMENTS

| | | |
|---|---|---|
| CZ | 302225 B6 | 12/2010 |
| WO | 97/34485 | 9/1997 |
| WO | 2009/003428 A2 | 1/2009 |
| WO | 2010/130233 A1 | 11/2010 |
| WO | 2012/031574 A1 | 3/2012 |
| WO | WO-2015175813 A1 * | 11/2015 ............ C07D 473/34 |

OTHER PUBLICATIONS

International Search Report and Written Opinion for PCT/CZ2015/050014 filed Dec. 9, 2015.

* cited by examiner

*Primary Examiner* — Erin E Hirt
(74) *Attorney, Agent, or Firm* — Notaro, Michalos & Zaccaria P.C.

(57) ABSTRACT

The invention relates to substituted 6-anilino-9-heterocyclylpurine derivatives of formula I wherein R denotes one to five substituents independently selected from the group hydrogen, halogen, hydroxy, amino, alkyloxy and alkyl group, R2 is selected from the group comprising amino, halogen, hydroxy, thio, and alkylthio group, Cyc is five- or six-membered heterocyclic ring containing one oxygen atom. The derivatives are useful for inhibition of plant stress.

10 Claims, 10 Drawing Sheets

SUBSTITUTED 6-ANILINO-9-HETEROCYCLYLPURINE DERIVATIVES FOR INHIBITION OF PLANT STRESS

TECHNICAL FIELD

The invention relates to 2-substituted-6-anilino-9-heterocyclylpurine derivatives, their use in agriculture and preparations containing these derivatives.

BACKGROUND ART

Cytokinins are plant hormones that regulate a large number of developmental and physiological processes in plants. With the exception of diphenylurea, all naturally occurring cytokinins are 6-substituted purine drivatives that can be further modified by substitution. Cytokinin oxidase/dehydrogenase (CKX) is an enzyme that is responsible for cytokinin degradation. The modulation of cytokinin levels by either exogenous application of cytokinins or regulation of their endogenous levels genetically through cytokinin oxidase/dehydrogenase (CKX, EC 1.5.99.12) have already shown possible applications in agriculture. CKX inhibitors are cytokinin derivatives that can delay cytokinin degradation and therefore prolong the period of cytokinin action. For example, exogenous application of cytokinins led to shortening of the time to anthesis in tomato (Sawhney and Shukla, Am J Bot 81:1640, 1994) or reversion of male sterility in barley (Ahokas, Proc. Natl. Acad. Sci. USA 79:7605, 1992). Anther- and pollen-specific expression of CKX in maize was shown to be a potential tool for generating male sterility for production of hybrid varieties of traditionally non-hybrid crops. Recent work reported CKX involvement in regulation of rice grain production (Ashikari et al., Science 309:741, 2005).

We have recently discovered that novel generations of CKX inhibitors could be based on 2-substituted 6-anilinopurines (CZ302225B6). It is an object of the present invention to provide further compounds having improved selectivity and efficiency index in plants, i.e., having lower toxicity and higher activity than known active substances. The compounds of this invention exhibit surprisingly strong antistress and antisenescence properties on plants.

DISCLOSURE OF THE INVENTION

The object of this invention are 2-substituted-6-anilino-9-heterocyclylpurines of the general formula I

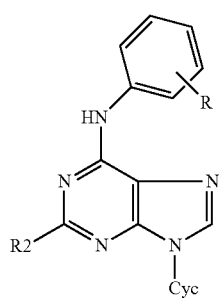

(I)

and pharmaceutically acceptable salts thereof with alkali metals, ammonium or amines, in the form of racemates or optically active isomers, as well as their addition salts with acids, wherein R denotes one to five substituents independently selected from the group comprising hydrogen, halogen, hydroxy, amino, alkyloxy and alkyl group, R2 is selected from the group comprising amino, halogen, hydroxy, thio, and alkylthio group, Cyc is five- or six-membered heterocyclic ring containing one oxygen atom.

Cyc is preferably selected from tetrahydropyranyl and tetrahydrofuranyl, more preferably from tetrahydropyran-2-yl and tetrahydrofuran-2-yl.

R2 is preferably selected from the group comprising chloro, fluoro, bromo, iodo, amino, hydroxy, thio, methylthio.

The generic substituent groups have meanings as follows:
amino denotes the group —NH$_2$,
hydroxy denotes the group —OH,
halogen denotes an atom selected from the group comprising fluorine, bromine, chlorine and iodine atom,
thio denotes the group —SH,
alkyl denotes branched or unbranched alkyl group containing 1 to 6 carbon atoms, preferably 1 to 4 carbon atoms,
hydroxy denotes the group —OH,
alkyloxy denotes the group —ORa, wherein Ra is alkyl,
alkylthio denotes the group —SRb, wherein Rb is alkyl.

In accordance with the invention, substituted 6-anilino-9-heterocyclylpurine derivatives of the general formula I are selected from: 2-(chloro, fluoro, bromo, iodo, amino, hydroxy, thio, methylthio)-6-anilino-9-(tetrahydropyran-2-yl or tetrahydrofuran-2-yl)purine purine, 2-(chloro, fluoro, bromo, iodo, amino, hydroxy, thio, methylthio)-6-(2-chloroanilino)-9-(tetrahydropyran-2-yl or tetrahydrofuran-2-yl)purine, 2-(chloro, fluoro, bromo, iodo, amino, nitro, thio, methylthio, methyl)-6-(3-chloroanilino)-9-(tetrahydropyran-2-yl or tetrahydrofuran-2-yl)purine, 2-(chloro, fluoro, bromo, iodo, amino, hydroxy, thio, methylthio)-6-(4-chloroanilino)-9-(tetrahydropyran-2-yl or tetrahydrofuran-2-yl)purine, 2-(chloro, fluoro, bromo, iodo, amino, hydroxy, thio, methylthio)-6-(2-fluoroanilino)-9-(tetrahydropyran-2-yl or tetrahydrofuran-2-yl)purine, 2-(chloro, fluoro, bromo, iodo, amino, hydroxy, thio, methylthio)-6-(3-fluoroanilino)-9-(tetrahydropyran-2-yl or tetrahydrofuran-2-yl)purine, 2-(chloro, fluoro, bromo, iodo, amino, hydroxy, thio, methylthio)-6-(4-fluoroanilino)-9-(tetrahydropyran-2-yl or tetrahydrofuran-2-yl)purine, 2-(chloro, fluoro, bromo, iodo, amino, hydroxy, thio, methylthio)-6-(2-bromoanilino)-9-(tetrahydropyran-2-yl or tetrahydrofuran-2-yl)purine, 2-(chloro, fluoro, bromo, iodo, amino, nitro, thio, methylthio, methyl)-6-(3-bromoanilino)-9-(tetrahydropyran-2-yl or tetrahydrofuran-2-yl)purine, 2-(chloro, fluoro, bromo, iodo, amino, nitro, thio, methylthio, methyl)-6-(4-bromoanilino)-9-(tetrahydropyran-2-yl or tetrahydrofuran-2-yl)purine, 2-(chloro, fluoro, bromo, iodo, amino, nitro, thio, methylthio, methyl)-6-(2-methoxyanilino)-9-(tetrahydropyran-2-yl or tetrahydrofuran-2-yl)purine, 2-(chloro, fluoro, bromo, idodo, amino, nitro, thio, methylthio, methyl)-6-(3-methoxyanilino)-9-(tetrahydropyran-2-yl or tetrahydrofuran-2-yl)purine, 2-(chloro, fluoro, bromo, iodo, amino, hydroxy, thio, methylthio)-6-(4-methoxyanilino)-9-(tetrahydropyran-2-yl or tetrahydrofuran-2-yl)purine, 2-(chloro, fluoro, bromo, iodo, amino, hydroxy, thio, methylthio)-6-(2-ethoxyanilino)-9-(tetrahydropyran-2-yl or tetrahydrofuran-2-yl)purine, 2-(chloro, fluoro, bromo, iodo, amino, hydroxy, thio, methylthio)-6-(3-ethoxyanilino)-9-(tetrahydropyran-2-yl or tetrahydrofuran-2-yl)purine, 2-(chloro, fluoro, bromo, iodo, amino, hydroxy, thio, methylthio)-6-(4-ethoxyanilino)-9-(tetrahydropyran-2-yl or tetrahydrofuran-2-yl)purine, 2-(chloro, fluoro, bromo, iodo, amino, hydroxy, thio, methylthio)-6-(2-aminoanilino)-9-(tetrahydropyran-2-yl or tetrahydrofuran-2-yl)purine, 2-(chloro, fluoro, bromo, iodo, amino, hydroxy, thio, methylthio)-6-(3-aminoanilino)-9-(tetrahydropyran-2-yl or tetrahydrofuran-2-yl)purine, 2-(chloro, fluoro, bromo, iodo, amino, hydroxy, thio, methylthio)-6-(4-aminoanilino)-9-(tetrahydropyran-2-yl or tetrahydrofuran-2-yl)purine, 2-(chloro, fluoro, bromo, iodo,amino, hydroxy, thio, methylthio)-6-(2-methylanilino)-9-(tetrahydropyran-2-yl or tetrahydrofuran-2-yl)purine, 2-(chloro, fluoro, bromo, iodo, amino, hydroxy, thio, methylthio)-6-(3-methylanilino)-9-(tetrahydropyran-2-yl or tetrahydrofuran-2-yl)purine, 2-(chloro, fluoro, bromo, iodo,amino, hydroxy, thio, methylthio)-6-(4-methylanilino)-9-(tetrahydropyran-2-yl or tetrahydrofuran-2-yl)purine, 2-(chloro, fluoro, bromo, iodo, amino, hydroxy, thio, methylthio)-6-(2-hydroxyanilino)-9-(tetrahydropyran-2-yl or tetrahydrofuran-2-yl)purine, 2-(chloro, fluoro, bromo, iodo, amino, hydroxy, thio, methylthio)-6-(3-hydroxyanilino)-9-(tetrahydropyran-2-yl or tetrahydrofuran-2-yl)purine, 2-(chloro, fluoro, bromo, iodo, amino, hydroxy, thio, methylthio)-6-(4-hydroxyanilino)-9-(tetrahydropyran-2-yl or tetrahydrofuran-2-yl)purine, 2-(chloro, fluoro, bromo, iodo, amino, hydroxy, thio, methylthio)-6-(2,3-difluoroanilino)-9-(tetrahydropyran-2-yl or tetrahydrofuran-2-yl)purine, 2-(chloro, fluoro, bromo, iodo, amino, hydroxy, thio, methylthio)-6-(2,4-difluoroanilino)-9-(tetrahydropyran-2-yl or tetrahydrofuran-2-yl)purine, 2-(chloro, fluoro, bromo, iodo, amino, hydroxy, thio, methylthio)-6-(2,3,4-trifluoroanilino)-9-(tetrahydropyran-2-yl or tetrahydrofuran-2-yl)purine, 2-(chloro, fluoro, bromo, iodo, amino, hydroxy, thio, methylthio)-6-(2,4,5-trifluorooniline)-9-(tetrahydropyran-2-yl or tetrahydrofuran-2-yl)purine, 2-(chloro, fluoro, bromo, iodo, amino, hydroxy, thio, methylthio)-6-(2,3-dichloroanilino)-9-(tetrahydropyran-2-yl or tetrahydrofuran-2-yl)purine, 2-(chloro, fluoro, bromo, iodo, amino, hydroxy, thio, methylthio)-6-(2,4-dichloroanilino)-9-(tetrahydropyran-2-yl or tetrahydrofuran-2-yl)purine, 2-(chloro, fluoro, bromo, iodo, amino, hydroxy, thio, methylthio)-6-(2,4-dimethoxyanilino)-9-(tetrahydropyran-2-yl or tetrahydrofuran-2-yl)purine, 2-(chloro, fluoro, bromo, iodo, amino, nitro, thio, methylthio, methyl)-6-(2,3-dimethoxyanilino)-9-(tetrahydropyran-2-yl or tetrahydrofuran-2-yl)purine, 2-(chloro, fluoro, bromo, iodo, amino, hydroxy, thio, methylthio)-6-(3,4-dimethoxyanilino)-9-(tetrahydropyran-2-yl or tetrahydrofuran-2-yl)purine, 2-(chloro, fluoro, bromo, iodo, amino, hydroxy, thio, methylthio)-6-(2,5-dimethoxyanilino)-9-(tetrahydropyran-2-yl or tetrahydrofuran-2-yl)purine, 2-(chloro, fluoro, bromo, iodo,amino, hydroxy, thio, methylthio)-6-(3,4,5-trimethoxyanilino)-9-(tetrahydropyran-2-yl or tetrahydrofuran-2-yl)purine, 2-(amino, chloro, fluoro, bromo, iodo,amino, hydroxy, thio, methylthio)-6-(2,4,6-trimethoxyanilino)-9-(tetrahydropyran-2-yl or tetrahydrofuran-2-yl)purine, 2-(chloro, fluoro, bromo, amino, nitro, thio, methylthio, methyl)-6-(2,3-dimethylanilino)-9-(tetrahydropyran-2-yl or tetrahydrofuran-2-yl)purine, 2-(chloro, fluoro, bromo, iodo, amino, hydroxy, thio, methylthio)-6-(2,4-dimethylanilino)-9-(tetrahydropyran-2-yl or tetrahydrofuran-2-yl)purine, 2-(chloro, fluoro, bromo, iodo, amino, hydroxy, thio, methylthio)-6-(3,4-dimethylanilino)-9-(tetrahydropyran-2-yl or tetrahydrofuran-2-yl)purine, 2-(chloro, fluoro, bromo, iodo, amino, hydroxy, thio, methylthio)-6-(3,5-dimethylanilino)-9-(tetrahydropyran-2-yl or tetrahydrofuran-2-yl)purine, 2-(chloro, fluoro, bromo, iodo, amino, hydroxy, thio, methylthio)-6-(2,3-dihydroxyanilino)-9-(tetrahydropyran-2-yl or tetrahydrofuran-2-yl)purine, 2-(chloro, fluoro, bromo, iodo, amino, hydroxy, thio, methylthio)-6-(2,4-dihydroxyanilino)-9-(tetrahydropyran-2-yl or tetrahydrofuran-2-yl)purine, 2-(chloro, fluoro, bromo, iodo, amino, hydroxy, thio, methylthio)-6-(2,5-dihydroxyanilino)-9-(tetrahydropyran-2-yl or tetrahydrofuran-2-yl)purine, 2-(amino, chloro, fluoro, bromo, iodo, amino, hydroxy, thio, methylthio)-6-(3,5-dihydroxyanilino)-9-(tetrahydropyran-2-yl or tetrahydrofuran-2-yl)purine, 2-(chloro, fluoro, bromo, iodo, amino, hydroxy, thio, methylthio)-6-(3-hydroxy-2-methylanilino)-9-(tetrahydropyran-2-yl or tetrahydrofuran-2-yl)purine, 2-(chloro, fluoro, bromo, iodo, amino, hydroxy, thio, methylthio)-6-(3-hydroxy-4-methylanilino)-9-(tetrahydropyran-2-yl or tetrahydrofuran-2-yl)purine, 2-(chloro, fluoro, bromo, iodo, amino, hydroxy, thio, methylthio)-6-(2-hydroxy-5-methylanilino)-9-(tetrahydropyran-2-yl or tetrahydrofuran-2-yl)purine, 2-(chloro, fluoro, bromo, iodo, amino, hydroxy, thio, methylthio)-6-(3-hydroxy-2-methoxyanilino)-9-(tetrahydropyran-2-yl or tetrahydrofuran-2-yl)purine, 2-(chloro, fluoro, bromo, iodo, amino, hydroxy, thio, methylthio)-6-(3-hydroxy-4-methoxyanilino)-9-(tetrahydropyran-2-yl or tetrahydrofuran-2-yl)purine, 2-(chloro, fluoro, bromo, iodo, amino, hydroxy, thio, methylthio)-6-(2-hydroxy-3-methoxyanilino)-9-(tetrahydropyran-2-yl or tetrahydrofuran-2-yl)purine, 2-(chloro, fluoro, bromo, iodo, amino, hydroxy, thio, methylthio)-6-(2-hydroxy-5-methoxyanilino)-9-(tetrahydropyran-2-yl or tetrahydrofuran-2-yl)purine, 2-(chloro, fluoro, bromo, iodo, amino, hydroxy, thio, methylthio)-6-(4-hydroxy-3,5-dimethoxyanilino)-9-(tetrahydropyran-2-yl or tetrahydrofuran-2-yl)purine, 2-(chloro, fluoro, bromo, iodo, amino, hydroxy, thio, methylthio)-6-(2-chloro-4-methoxyanilino)-9-(tetrahydropyran-2-yl or tetrahydrofuran-2-yl)purine, 2-(chloro, fluoro, bromo, iodo, amino, hydroxy, thio, methylthio)-6-(2-chloro-5-methoxyanilino)-9-(tetrahydropyran-2-yl or tetrahydrofuran-2-yl)purine, 2-(chloro, fluoro, bromo, iodo, amino, hydroxy, thio, methylthio)-6-(2-chloro-3-methoxyanilino)-9-(tetrahydropyran-2-yl or tetrahydrofuran-2-yl)purine, 2-(chloro, fluoro, bromo, iodo, amino, hydroxy, thio, methylthio)-6-(2-bromo-3-methoxyanilino)-9-(tetrahydropyran-2-yl or tetrahydrofuran-2-yl)purine, 2-(chloro, fluoro, bromo, iodo, amino, hydroxy, thio, methylthio)-6-(2-methoxy-3-chloroanilino)-9-(tetrahydropyran-2-yl or tetrahydrofuran-2-yl)purine, 2-(chloro, fluoro, bromo, iodo, amino, hydroxy, thio, methylthio)-6-(2-methoxy-4-chloroanilino)-9-(tetrahydropyran-2-yl or tetrahydrofuran-2-yl)purine, and salts thereof with alkali metals, ammonium or amines, in the forms of racemates or optically active isomers, as well as their addition salts with acids.

The following substituted 6-anilino-9-heterocyclylpurine derivatives are particularly preferred, namely: 2-(chloro, fluoro, bromo)-6-(3-methoxyanilino)-9-(tetrahydropyran-2-yl or tetrahydrofuran-2-yl)purine, 2-(chloro, fluoro, bromo)-6-(2-hydroxy-3-methoxyanilino)-9-(tetrahydropyran-2-yl or tetrahydrofuran-2-yl)purine, 2-(chloro, fluoro, bromo)-6-(2-chloro-3-methoxyanilino)-9-(tetrahydropyran-2-yl or tetrahydrofuran-2-yl)purine, 2-(chloro, fluoro, bromo)-6-(2-bromo-3-methoxyanilino)-9-(tetrahydropyran-2-yl or tetrahydrofuran-2-yl)purine, 2-(chloro, fluoro, bromo)-6-(4-hydroxyanilino)-9-(tetrahydropyran-2-yl or tetrahydrofuran-2-yl)purine, and salts thereof with alkali metals, ammonium or amines, in the forms of racemates or optically active isomers, as well as their addition salts with acids.

The present invention further includes antisenescent and/or antistress preparations comprising at least one compound of general formula I or salts thereof with alkali metals, ammonium or amines, in the forms of racemates or optically active isomers, as well as their addition salts with acids, and auxiliary substances.

The invention further includes antisenescent and/or antistress preparations for plants, plant organs and plant cells, comprising at least one compound of the general formula I or a salt thereof, and at least one auxiliary substance.

A further aspect of this invention is use of at least one substituted 6-anilino-9-hetercyclylpurine derivative of general formula I for inhibiting stress in whole plants, plant organs, plant tissues and/or plant cells.

A further aspect of this invention is use of at least one substituted 6-anilino-9-hetercyclylpurine derivative of general formula I for stimulation of growth and/or development of plant shoots without inhibiting growth and/or development of roots.

A further aspect of this invention is use of at least one substituted 6-anilino-9-hetercyclylpurine derivative of general formula I as plant antistress factor, in particular for increasing the yield and quality of agricultural product in harmful conditions. Harmful conditions may include drought, heat, salinity, light, freezing and flowage stress. The use as plant antistress factor relates in particular to agricultural use.

A further aspect of the invention is a method of inhibiting and/or preventing senescence and/or stress in plants, plant organs, plant tissues and/or plant cells, comprising the application of at least one 2-substituted-6-anilino-9-heterocyclylpurine derivative of the general formula I or a salt thereof for to said whole plant, plant organs, tissues and cells.

Another aspect of the invention is a method of stimulation of plant shoot growth and/or development without inhibition of root growth and/or development, comprising the application of at least one 2-substituted-6-anilino-9-heterocyclylpurine derivative of the general formula I or a salt thereof to a plant, a seedling or a seed.

A further aspect of the invention is use of 2-substituted-6-anilino-9-heterocyclylpurine derivatives of the general formula I in tissue cultures for stimulation of proliferation and morphogenesis.

A further aspect of the invention is use of 2-substituted-6-anilino-9-heterocyclylpurine derivatives of the general formula I as plant antistress factors in agriculture, in particular to increase crop production in stress conditions to dispatch grain filling and to increase grain and fruit size of plants, to shorten plant seed germination period, to increase the yield and quality of agricultural products, to enhance root and shoot growth, and to increase stress resistance to environmental factors. The compounds of this invention show stimulation of plant shoot growth and development without root growth inhibition.

A further particular aspect of the invention is the use of 2-substituted-6-anilino-9-heterocyclylpurine derivatives of the general formula I as plant antistress factors for decreasing of stress-induced sensencence in the production of crops, in particular cereals (wheat, barley, rice, maize, rye, oat, sorghum, and related species), beet (sugar beet and fodded beet); pomes, drupes and soft fruits (apples, pears, plums, peaches, almonds, cherries, strawberries, raspberries and blackberries); leguminous plants (beans, lentils, peas, soybeans); oil plants (rape, mustard, poppy, olives, sunflowers, coconut, *Ricinus*, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, *cinnamomum*, camphor) or plants such as tobacco, nuts, eggplants, sugar cane, tea, vine grapes, hops, bananas and natural rubber and medicinal plants, as well as ornamentals. Crops include those which have been rendered tolerant towards classes of growth factors by conventional breeding methods or genetic engineering methods.

A further aspect of the invention is the use of 2-substituted-6-anilino-9-heterocyclylpurine derivatives of the general formula I as plant antistress factors for delaying the aging and senescence of plant cells, plant tissues, plant organs and/or the whole plants.

A further aspect of the invention is the use of 2-substituted-6-anilino-9-heterocyclylpurine derivatives of the general formula I, for plant embryonic cells production and plant cloning.

The compounds of the general formula I are used in unmodified form or, preferably, together with the auxiliary substances conventionally employed in the art of preparations. To this end they are conveniently formulated as concentrates of active compounds as well as suspensions and dispersions, preferably isotonic water solutions, suspensions and dispersion, diluted emulsions, soluble powders, dusts, granulates, creams, gels, oil suspensions and also encapsulations, e.g. in polymeric substances. As with the type of the preparation, the methods of application, such as spraying, atomizing, dusting, scattering, coating or pouring, are chosen in accordance with the intended objectives and the prevailing circumstances. The preparations may be sterilized and/or contain further auxiliary substances of neutral character, such as preservatives, stabilizers, wetting agents, emulgators, solubilizing agents, fertilizers, micronutrient donors or other substances for obtaining special effects.

The compounds of the formula I can be mixed with other plant growth regulators, herbicides, fungicides and insecticides, resulting in synergistic activities.

Preparations

The preparations comprising the compounds (active ingredients) of formula I, optionally in the form of salts, and, where appropriate, one or more solid or liquid auxiliary substances, are prepared in a manner known per se, e.g. by intimately mixing and/or grinding the active ingredients with the auxiliary substances, e.g. solvents or solid carriers. In addition, surface-active compounds (surfactants) may also be used in the preparation of the formulations.

Depending on the nature of the compound of formula I to be formulated, suitable surface-active compounds are non-ionic, cationic and/or anionic surfactants and surfactant mixtures having good emulsifying, dispersing and wetting properties. Examples of suitable anionic, non-ionic and cationic surfactants are listed, for example, in WO 97/34485.

Also suitable in the preparation of the growth regulator compositions according to the invention are the surfactants conventionally used in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, MunichNienna, 1981 and M. and J. Ash, "Encyclopedia of Surfactants", Voll-111, Chemical Publishing Co., New York, 1980-81. The reparations usually contain from 0.1 to 99% by weight, especially from 0.1 to 95% by weight, of active ingredient mixture comprising a compound of formula I, from 1 to 99.9% by weight of a solid or liquid adjuvant, and from 0.1 to 25% by weight, especially from 0.1 to 25% by weight, of a surfactant.

Whereas commercial products are usually formulated as concentrates, the end user will normally employ dilute formulations. The composition can thus contain also further additives, such as stabilizers, e.g., plant oils or epoxidized plant oils (epoxidized palm oil 0;1, rapeseed or olive oil), defoamers, e.g., silicon oil, preservatives, wetting agents or emulgators, viscosity agent, binders, glues, and also fertilizers and other active additives. Preferred formulations have especially the following compositions: (%=percent by weight)

Emulsifiable Concentrates:
active ingredient mixture: 1 to 90%, preferably 5 to 20%
surfactant: 1 to 30%, preferably 10 to 20%
liquid carrier: 5 to 98%, preferably 60 to 85%
Dusts:
active ingredient mixture: 0.1 to 10%, preferably 0.1 to 5%
solid carrier: 99.9 to 90%, preferably 99.9 to 99%
Suspension Concentrates:
active ingredient mixture: 5 to 75%, preferably 10 to 50%
water: 94 to 24%, preferably 88 to 30%
surfactant: 1 to 40%, preferably 2 to 30%
Wettable Powders:
active ingredient mixture: 0.5 to 90%, preferably 1 to 80%
surfactant: 0.5 to 20%, preferably 1 to 15%
solid carrier: 5 to 99%, preferably 15 to 90%
Granules:
active ingredient mixture: 0.1 to 30%, preferably 0.1 to 15%
solid carrier: 99.9 to 70%, preferably 99.9 to 85%

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of growth factors of formula I, or of compositions comprising them, various methods and techniques come into consideration, such as, for example, the following:

i) Seed Dressing a) Dressing of the seeds with a wettable powder formulation of a compound of the general formula I by shaking in a vessel until uniformly distributed over the seed surface (dry dressing). In that procedure approximately from 1 to 500 g of compound of the general formula I (4 g to 2 kg of wettable powder) are used per 100 kg of seed.

b) Dressing of the seeds with an emulsifiable concentrate of a compound of formula I according to method a) (wet dressing).

c) Dressing by immersing the seeds for from 1 to 72 hours in a liquor comprising from 100 to 1000 ppm of a compound of formula I and optionally subsequently drying the seeds (immersion dressing).

Dressing the seed or treating the germinated seedling are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also enables the addition of other active ingredients or micronutrients: the concentration limits indicated can be varied up or down (repeat dressing).

ii) Application as a Tank Mixture

A liquid formulation of a mixture of antidote and growth regulator is used (ratio by weight of the one to the other from 10:1 to 1:100), the rate of application of growth regulator being from 0.005 to 5.0 kg per hectare. Such tank mixtures are applied before or after sowing.

iii) Application to the Seed Furrow

The compounds of formula I are introduced into the open, sown seed furrow in the form of an emulsifiable concentrate, wettable powder or granules. Once the seed furrow has been covered over, the growth regulator is applied in the usual manner in the pre-emergence process.

iv) Controlled Release of the Active Ingredient

The compounds of formula I are applied in solution to mineral granule carriers or polymerised granules (urea/formaldehyde) and dried. If desired, it is also possible to apply a coating that allows the active ingredient to be released in metered amounts over a specific period of time (coated granules).

EXAMPLES OF CARRYING OUT THE INVENTION

Figure 1:
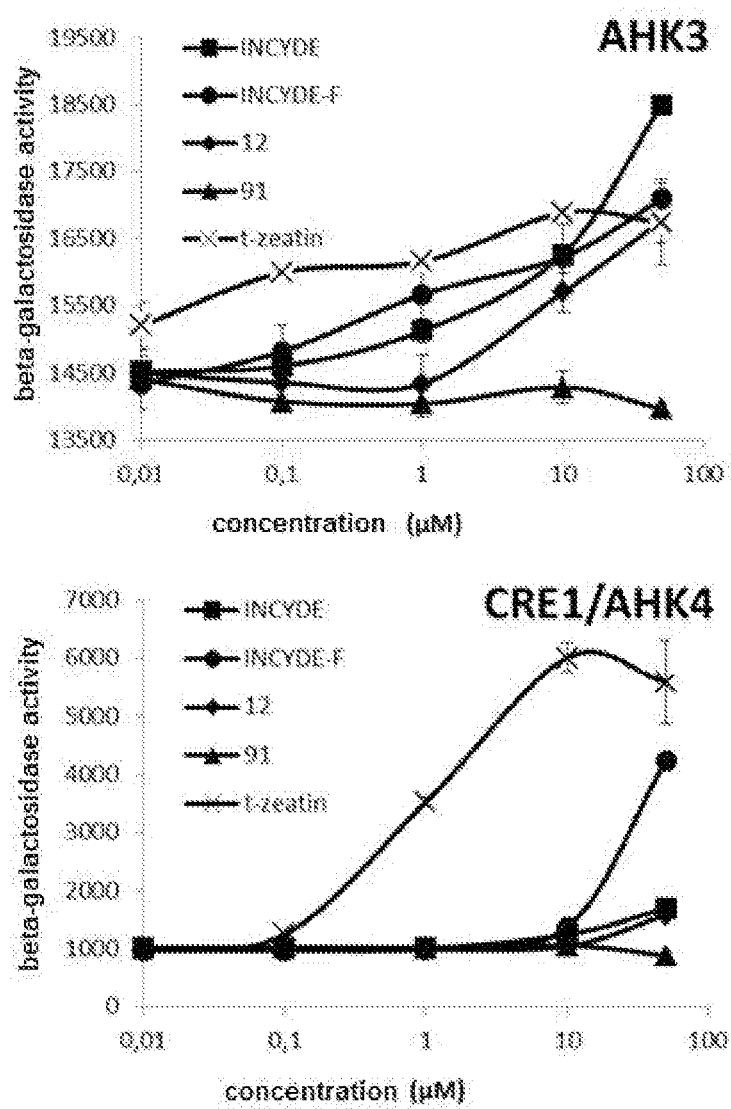
FIG. 1 shows differences in dose-dependent activation of cytokinin receptors AHK3 (upper chart) and CRE1/AHK4 (lower chart) in *Escherichia coli* receptor assay (Spíchal et al., 2004) by cytokinin trans-zeatin (tZ), inhibitors of cytokinin oxidase-dehydrogenase INCYDE (2-chloro-6-(3-methoxyanilino)purine) and INCYDE-F (2-fluoro-6-(3-methoxyanilino)purine) and representatives of the novel derivatives, compounds 12 and 91. Values represent means of three repetitions, error bars represent SD.

The starting material for the compounds of the formula I is 2,6-dichloro-9-(tetrahydropyran-2-yl)purine or 2,6-dichloro-9-(tetrahydrofuran-2yl)purine prepared from 2,6-dichloropurine and 3,4-dihydro-2H-pyran or 2,3-dihydrofuran in acidic conditions of trifluoroacetic acid. Another starting material can be 2-amino-6-chloro-9-(tetrahydropyran-2-yl) or 9-(tetrahydrofuran-2-yl)purine or 2-fluoro-6-chloro-9-(tetrahydropyran-2-yl) or 9-(tetrahydrofuran-2-yl)purine, synthesised from 2-amino-6-chloropurine by reaction with tetrafluoroboric acid in the presence of sodium nitrate aqueous solution (Beach et al., 1992). Another starting compound, 2-bromo-6-chloro-9-(tetrahydropyran-2yl) and 9-(tetrahydrofuran-2-yl)purine, can be prepared from 2-amino-6-chloropurine (Kim Hak Sung et al.; J. Med. Chem. 46; 23; 2003; 4974-4987). Yet another starting material can be 2-methyl-6-chloro-9-(tetrahydropyran-2yl) or 9-(tetrahydrofuran-2yl)purine (Kim et al., 2003). Yet another starting material can be 2-nitro-6-chloro-9-Boc-purine, which can be prepared from 6-chloropurine (Rodenko et al.; J. Am. Chem. Soc. 2005, 127, 5957-5963). Starting substituted phenylamines, not commercially available (others obtained via Sigma Aldrich or Fluorochem), were prepared from the corresponding aldehydes in the presence of suitable catalyst. These, which have more hydroxyl groups, may also be prepared by demethylation of appropriate methoxyderivatives using 48% HBr in $N_2$ atmosphere.

Elemental analyses (C, H and N) were performed on an EA1108 CHN analyser (Fissons Instruments). The melting points were determined on a BÜCHI Melting Point B-540 apparatus. Analytical thin layer chromatography (TLC) was carried out using silica gel 60 $WF_{254}$ plates (Merck), mobile phase $CHCl_3$:MeOH: (9:1, v/v). ES+ mass spectra were recorded using direct probe on Waters ZMD 2000 mass spectrometer. The mass monitoring interval was 10-1500 amu. The spectra were collected using 3.0 second cyclical scans and applying sample cone voltage 25 V at source block temperature 150° C., desolvation temperature 80° C. and desolvation gas flow rate 200 l/hour. The mass spectrometer was directly coupled to a MassLynx data system. NMR spectra were measured in a Bruker Avance AV 300 spectrometer operating at a temperature of 300 K and a frequency of 300.13 MHz ($^1H$) and 75.48 MHz ($^{13}C$), respectively. Samples were prepared by dissolving the compounds in DMSO-$d_6$. Tetramethylsilane (TMS) was used as the internal standard.

Example 1

2-Chloro-6-anilino-9-(tetrahydropyran-2-yl)purine

Aniline (4.96 g; 0.05 mol) was added to a suspension of 2,6-dichloro-9-(tetrahydropyran-2-yl)purine (8.19 g; 0.03 mol) in n-propanol (60 ml) and N,N'-ethyldiisopropylamine (6.44 g; 0.05 mol) was added. The reaction mixture was stirred at 100° C. for 5 hours. After cooling to room temperature the precipitate was filtered off, washed with n-propanol (2×10 ml) and water (3×10 ml) and dried in the drying oven at 60° C. into constant weight. Yield: 6.26 g yellowish substance (84.9%). TLC (chloroform-methanol; 9:1): one single spot; free of the starting material, HPLC purity: 98+%. 1H-NMR, DMSO-$d_6$, TMS, ppm: 1.58m (2H, THP), 1.72-1.78m (1H, THP), 1.98d (2H, THP), 2.18-2.31m (1H, THP), 3.65-3.75m (1H, THP), 4.02d (1H, THP), 5.63d (1H, THP), 7.09t, J=8.0 Hz (1H, Ar—H), 7.37t, J=8.0 Hz (2H, Ar—H), 7.84d, J=8.0 Hz (2H, Ar—H), 8.30s (1H, C8-H), 10.18s (1H, N6-H).

Example 2

2-Chloro-6-(3-chloroanilino)-9-(tetrahydropyran-2-yl) or (tetrahydrofuran-2-yl)purine 2,6-dichloro-9-(tetrahydropyran-2-yl)purine (8.19 g; 0.03 mol) reacted with 3-chloroaniline (3.83 g; 0.03 mol) in n-butanol (40 ml) in the presence of triethylamine (7 ml; 0.05 mol) at 90° C. for 5 hours. After cooling to room temperature, the yellow precipitate was filtered off, washed with cold n-butanol (2×10 ml), water (3×10 ml) and dried in the drying oven at 60° C. into constant weight. Yield: 5.69 g yellow powder (65.8%). The crude product was crystallized from isopropanol. TLC (chloroform-methanol; 9:1): one single spot; free of starting material. HPLC purity: 98+%. 2-chloro-6-(3-chloroanilino)-9-(tetrahydrofuran-2-yl)purin was prepared in an analogical way from 2,6-dichloro-9-(tetrahydrofuran-2-yl)purine and 3-chloraniline 1H-NMR, DMSO-$d_6$, TMS, ppm: 1.58m (2H, THP), 1.72-1.78m (1H, THP), 1.98d (2H, THP), 2.18-2.31m (1H, THP), 3.65-3.75m (1H, THP), 4.02d (1H, THP), 5.63d (1H, THP), 7.11dd, $J_a$=8.2 Hz, $J_b$=2.4 Hz (1H, Ar—H), 7.37t, J=8.2 Hz, (1H, Ar—H), 7.82dd, $J_a$=8.2 Hz, $J_b$=2.1 Hz (1H, Ar—H), 8.06t, J=2.1 Hz (1H, Ar—H), 8.34s (1H, C8-H), 10.37bs (1H, N6-H).

Example 3

2-Chloro-6-(3-fluoroanilino)-9-(tetrahydropyran-2-yl or tetrahydrofuran-2-yl)purine This compound was prepared in a similar manner as described in example 2, by reaction of 2,6-dichloro-9-(tetrahydropyran-2-yl) or (9-tetrahydrofuran-2yl)purine (8.19 g; 7.77 g 0.03 mol) with 3-fluoroaniline (3.33 g, 0.03 mol). The reaction mixture was then evaporated on a rotary vacuum evaporator and the residue was partitioned between ethyl acetate and 0.5 M HCl. The organic layer was washed with water, dried with $MgSO_4$, and evaporated to give a yellow solid (3.72 g). The crude product was purified by flash chromatography. Yield: 2.20 g yellow crystalline powder. TLC (chloroform-methanol; 9:1): homogenous. HPLC purity: 98+%. 1H-NMR, DMSO-$d_6$, TMS, ppm: 1.58m (2H, THP), 1.72-1.78m (1H, THP), 1.98d (2H, THP), 2.18-2.31m (1H, THP), 3.65-3.75m (1H, THP), 4.02d (1H, THP), 5.63d (1H, THP), 6.59dd, $J_a$=8.0 Hz, $J_b$=2.5 Hz (1H, Ar—H), 7.02d, J=2.5 Hz (1H, Ar—H), 7.25dd, $J_a$=8.0 Hz, $J_b$=2.5 Hz (1H, C15-H), 7.32tt, $J_a$=8.0 Hz, $J_b$=2.5 Hz (1H, Ar—H), 8.28s (1H, C8-H), 11.17s (1H, N6-H).

Example 4

2-Chloro-6-(3-hydroxyanilino)-9-(tetrahydropyran-2-yl or tetrahydrofuran-2-yl)purine The compound was prepared by the reaction of 2,6-dichloro-(tetrahydropyran-2-yl) or (9-tetrahydrofuran- 2yl)purine (8.19 g; 7.77 g 0.03 mol), 3-aminophenol (3.27 g; 0.03 mol), and N,N-ethyldiisopropylamine (6.44 g; 0.05 mol) in n-butanol (40 ml) at 90° C. for 4 hours. The reaction mixture was then allowed to cool to room temperature and stirred. The formed crystalline precipitate was collected, rinsed with cold n-butanol (3×10 ml), water (3×10 ml) and dried in the oven into constant weight. TLC (chloroform-methanol; 9:1): homogenous. HPLC purity: 98+%. 1H-NMR, DMSO-d$_6$, TMS, ppm: 1.58m (2H, THP), 1.72-1.78m (1H, THP), 1.97d (2H, THP), 2.18-2.31m (1H, THP), 3.65-3.75m (1H, THP), 4.02d (1H, THP), 5.63d (1H, THP), 7.13t (1H, Ar—H), 7.28d (1H, Ar—H), 7.38s (1H, Ar—H), 8.30s (1H, C8-H), 9.44s (1H, N6-H), 10.09s (1H, OH).

Example 5

2-Chloro-6-(3-methoxyanilino)-9-(tetrahydropyran-2-yl or tetrahydrofuran-2-yl)purine To a suspension of 2,6-dichloro-9-(tetrahydropyran-2yl) or 9-(tetrahydrofuran-2yl)purine (8.19 g; 7.77 g 0.03 mol) and m-anisidine (3.69 g; 0.03 mol) in n-pentanol (40 ml), triethylamine (7 ml; 0.05 mol) was added. The reaction mixture was stirred at 90° C. for 4 hours and then it was allowed to cool to the room temperature. The white precipitate was collected, washed with isopropanol (2×10 ml) and water (3×10 ml). The crude product was purified by the crystallization from methanol in the presence of activated charcoal to give white crystals. Yield: 4.36 g (77.8%). TLC (chloroform-methanol; 9:1): one single spot, free of starting material, HPLC purity: 98+%

Alternative Procedure:

To a suspension of 2-chloro-6-(3-methoxyanilino)purine (10 g; 0.036 mol) in dioxane (250 ml) and 3,4-dihydropyran (10 ml; 0.1 mol), trifluoroacetic acid (10 ml; 0.13 mol) was added dropwise. The reaction mixture was then warmed up to 60° C. and stirred for 2 hours at the same temperature. Then it was cooled to 25° C. and neutralized with 7 M methanolic ammonia (20 ml). The solvent and an excess of trifluoroacetic acid was removed in vacuum rotary evaporator, the residue was partitioned between ethyl acetate (200 ml) and water (200 ml). Water phase was extracted with ethyl acetate (2×50 ml). The combined extracts were washed with brine (30 ml), dried with anhydrous sodium sulphate and evaporated to give a crude product (foam; 12.95 g, quant.). Purity (HPLC-MS min. 93%). The crude product was re-crystallized from ethyl acetate-petrolether (1:10); yield: 10.0 g (77.0%). HPLC purity: 97+%. 1H-NMR, DMSO-d$_6$, TMS, ppm: 1.58m (2H, THP), 1.72-1.78m (1H, THP), 1.98d (2H, THP), 2.18-2.31m (1H, THP), 3.65-3.75m (1H, THP), 3.76s (3H, CH$_3$), 4.02d (1H, THP), 5.63d (1H, THP), 6.66-6.70 m (1H, Ar—H), J$_a$=8, J$_b$=2.2 Hz), 7.26t (1H, Ar—H), J=8 Hz), 7.45d (H, Ar—H), J=8.0 Hz), 7.58t (1H, Ar—H), J=2.2 Hz), 8.54s (1H, C8), 10.27s (H, N6-H).

TABLE 1

Compounds Prepared by the methods of Examples 1-5

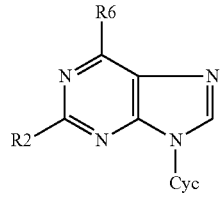

| | PURINE SUBSTITUENT | | | CHN ANALYSES | MS ANALYSES-ZMD | |
|---|---|---|---|---|---|---|
| | R6 | R2 | Cyc | [%] | [M − H]$^−$ a) | [M + H]$^+$ b) |
| 1 | anilino | chloro | tetrahydropyranyl | C = 58.5; H = 4.9; N = 21.0 | 328 | 330 |
| 2 | 2-chloroanilino | chloro | tetrahydropyranyl | C = 53.1; H = 3.9; N = 18.7 | 362 | 364 |
| 3 | 3-chloroanilino | chloro | tetrahydropyranyl | C = 53.3; H = 3.8; N = 18.9 | 362 | 364 |
| 4 | 4-chloroanilino | chloro | tetrahydropyranyl | C = 53.1; H = 4.0; N = 18.7 | 362 | 364 |
| 5 | 2-fluoroanilino | chloro | tetrahydropyranyl | C = 55.4; H = 4.1; N = 19.7 | 346 | 348 |
| 6 | 3-fluoroanilino | chloro | tetrahydropyranyl | C = 55.3; H = 4.1; N = 19.8 | 346 | 348 |
| 7 | 4-fluoroanilino | chloro | tetrahydropyranyl | C = 55.3; H = 4.1; N = 19.8 | 346 | 348 |
| 8 | 2-hydroxyanilino | chloro | tetrahydropyranyl | C = 55.9; H = 4.7; N = 20.0 | 344 | 346 |
| 9 | 3-hydroxyanilino | chloro | tetrahydropyranyl | C = 56.0; H = 4.5; N = 19.9 | 344 | 346 |
| 10 | 4-hydroxyanilino | chloro | tetrahydropyranyl | C = 55.9; H = 4.7; N = 19.8 | 344 | 346 |
| 11 | 2-methoxyanilino | chloro | tetrahydropyranyl | C = 57.0; H = 5.2; N = 19.2 | 358 | 360 |
| 12 | 3-methoxyanilino | chloro | tetrahydropyranyl | C = 56.9; H = 5.2; N = 19.1 | 358 | 360 |
| 13 | 4-methoxyanilino | chloro | tetrahydropyranyl | C = 57.0; H = 5.2; N = 18.9 | 358 | 360 |
| 14 | 2-aminoanilino | chloro | tetrahydropyranyl | C = 56.0; H = 5.0; N = 24.1 | 343 | 345 |
| 15 | 3-aminoanilino | chloro | tetrahydropyranyl | C = 55.9; H = 5.1; N = 23.9 | 343 | 345 |
| 16 | 4-aminoanilino | chloro | tetrahydropyranyl | C = 55.9; H = 5.0; N = 23.9 | 343 | 345 |
| 17 | 3,4-dimethoxyanilino | chloro | tetrahydropyranyl | C = 55.9; H = 5.3; N = 17.6 | 388 | 390 |
| 18 | 2,5-dimethoxyanilino | chloro | tetrahydropyranyl | C = 56.1; H = 5.3; N = 17.4 | 388 | 390 |
| 19 | 3,4,5-trimethoxyanilino | chloro | tetrahydropyranyl | C = 54.9; H = 5.2; N = 16.0 | 418 | 420 |
| 20 | 3,4-dihydroxyanilino | chloro | tetrahydropyranyl | C = 53.5; H = 4.6; N = 19.1 | 360 | 362 |
| 21 | 2,5-dihydroxyanilino | chloro | tetrahydropyranyl | C = 53.3; H = 4.5; N = 19.0 | 360 | 362 |
| 22 | 2-chloro-5-methoxyanilino | chloro | tetrahydropyranyl | C = 52.1; H = 4.5; N = 17.5 | 392 | 394 |
| 23 | 2-chloro-3-methoxyanilino | chloro | tetrahydropyranyl | C = 52.0; H = 4.5; N = 17.8 | 392 | 394 |
| 24 | 2-bromo-3-methoxyanilino | chloro | tetrahydropyranyl | C = 46.9; H = 4.0; N = 15.5 | 437 | 439 |

TABLE 1-continued

Compounds Prepared by the methods of Examples 1-5

|  | PURINE SUBSTITUENT | | | CHN ANALYSES | MS ANALYSES-ZMD | |
|---|---|---|---|---|---|---|
|  | R6 | R2 | Cyc | [%] | [M − H]⁻ a) | [M + H]⁺ b) |
| 25 | 2-methoxy-3-chloroanilino | chloro | tetrahydropyranyl | C = 52.1; H = 4.6; N = 17.6 | 392 | 394 |
| 26 | 3-ethoxyanilino | chloro | tetrahydropyranyl | C = 58.1; H = 5.5; N = 18.6 | 372 | 374 |
| 27 | 2-hydroxy-5-methylanilino | chloro | tetrahydropyranyl | C = 56.9; H = 5.1; N = 19.3 | 358 | 360 |
| 28 | 3-hydroxy-4-methylanilino | chloro | tetrahydropyranyl | C = 57.0; H = 5.1; N = 19.1 | 358 | 360 |
| 29 | 3-hydroxy-2-methylanilino | chloro | tetrahydropyranyl | C = 56.8; H = 5.2; N = 19.1 | 358 | 360 |
| 30 | 3,4-dimethylanilino | chloro | tetrahydropyranyl | C = 60.8; H = 5.7; N = 19.1 | 356 | 358 |
| 31 | 2-hydroxy-3-methoxyanilino | chloro | tetrahydropyranyl | C = 54.7; H = 5.0; N = 18.4 | 374 | 376 |
| 32 | 2-hydroxy-4-methoxyanilino | chloro | tetrahydropyranyl | C = 54.9; H = 5.1; N = 18.3 | 374 | 376 |
| 33 | 4-hydroxy-3,5-dimethoxyanilino | chloro | tetrahydropyranyl | C = 53.5; H = 5.1; N = 16.9 | 404 | 406 |
| 34 | 2,3-difluoroanilino | chloro | tetrahydropyranyl | C = 52.8; H = 4.0; N = 18.8 | 364 | 366 |
| 35 | 2,4-difluoroanilino | chloro | tetrahydropyranyl | C = 52.8; H = 3.9; N = 18.7 | 364 | 366 |
| 36 | 2,3,4-trifluoroanilino | chloro | tetrahydropyranyl | C = 50.5; H = 3.5; N = 17.9 | 382 | 384 |
| 37 | 2,4,5-trifluoroanilino | chloro | tetrahydropyrany | C = 50.3; H = 3.4; N = 18.0 | 382 | 384 |
| 38 | 2,3-dichloroanilino | chloro | tetrahydropyranyl | C = 48.5; H = 3.7; N = 17.0 | 396 | 398 |
| 39 | 2,4-dichloroanilino | chloro | tetrahydropyranyl | C = 48.4; H = 3.6; N = 17.3 | 396 | 398 |
| 40 | 3,5-dichloroanilino | chloro | tetrahydropyranyl | C = 48.5; H = 3.6; N = 17.2 | 396 | 398 |
| 41 | anilino | chloro | tetrahydrofuranyl | C = 57,5; H = 4,3; N = 22,6 | 314 | 316 |
| 42 | 2-chloroanilino | chloro | tetrahydrofuranyl | C = 51.7; H = 3.5; N = 19.7 | 348 | 350 |
| 43 | 3-chloroanilino | chloro | tetrahydrofuranyl | C = 51.7; H = 3.5; N = 19.7 | 348 | 350 |
| 44 | 4-chloroanilino | chloro | tetrahydrofuranyl | C = 51.9; H = 3.5; N = 19.5 | 348 | 350 |
| 45 | 2-fluoroanilino | chloro | tetrahydrofuranyl | C = 54.4; H = 4.0; N = 20.5 | 332 | 334 |
| 46 | 3-fluoroanilino | chloro | tetrahydrofuranyl | C = 54.1; H = 3.9; N = 20.3 | 332 | 334 |
| 47 | 4-fluoroanilino | chloro | tetrahydrofuranyl | C = 54.1; H = 4.0; N = 20.2 | 332 | 334 |
| 48 | 2-hydroxyanilino | chloro | tetrahydrofuranyl | C = 54.7; H = 4.4; N = 20.7 | 330 | 332 |
| 49 | 3-hydroxyanilino | chloro | tetrahydrofuranyl | C = 54.9; H = 4.4; N = 20.6 | 330 | 332 |
| 50 | 4-hydroxyanilino | chloro | tetrahydrofuranyl | C = 54.5; H = 4.4; N = 21.0 | 330 | 332 |
| 51 | 2-methoxyanilino | chloro | tetrahydrofuranyl | C = 55.8; H = 4.8; N = 20.0 | 344 | 346 |
| 52 | 3-methoxyanilino | chloro | tetrahydrofuranyl | C = 56.0; H = 4.4; N = 19.8 | 344 | 346 |
| 53 | 4-methoxyanilino | chloro | tetrahydrofuranyl | C = 56.1; H = 4.7; N = 20.1 | 344 | 346 |
| 54 | 2-aminoanilino | chloro | tetrahydrofuranyl | C = 54.8; H = 4.7; N = 25.1 | 329 | 331 |
| 55 | 3-aminoanilino | chloro | tetrahydrofuranyl | C = 54.6; H = 4.7; N = 25.2 | 329 | 331 |
| 56 | 4-aminoanilino | chloro | tetrahydrofuranyl | C = 54.9; H = 4.9; N = 24.9 | 329 | 331 |
| 57 | 3,4-dimethoxyanilino | chloro | tetrahydrofuranyl | C = 54.6; H = 4.9; N = 18.2 | 374 | 376 |
| 58 | 2,5-dimethoxyanilino | chloro | tetrahydrofuranyl | C = 54.9; H = 5.1; N = 18.1 | 374 | 376 |
| 59 | 3,4,5-trimethoxyanilino | chloro | tetrahydrofuranyl | C = 53.9; H = 5.1; N = 17.0 | 404 | 406 |
| 60 | 3,4-dihydroxyanilino | chloro | tetrahydrofuranyl | C = 53.4; H = 4.6; N = 19.0 | 346 | 348 |
| 61 | 2,5-dihydroxyanilino | chloro | tetrahydrofuranyl | C = 53.6; H = 4.6; N = 18.8 | 346 | 348 |
| 62 | 2-chloro-5-methoxyanilino | chloro | tetrahydrofuranyl | C = 51.0; H = 4.1; N = 18.0 | 378 | 380 |
| 63 | 2-chloro-3-methoxyanilino | chloro | tetrahydrofuranyl | C = 50.9; H = 4.0; N = 18.2 | 378 | 380 |
| 64 | 2-bromo-3-methoxyanilino | chloro | tetrahydrofuranyl | C = 45.5; H = 3.7; N = 15.9 | 423 | 425 |
| 65 | 2-methoxy-3-chloroanilino | chloro | tetrahydrofuranyl | C = 50.7; H = 4.0; N = 18.0 | 378 | 380 |
| 66 | 3-ethoxyanilino | chloro | tetrahydrofuranyl | C = 57.0; H = 5.2; N = 19.3 | 358 | 360 |
| 67 | 2-hydroxy-5-methylanilino | chloro | tetrahydrofuranyl | C = 56.0; H = 4.6; N = 20.0 | 344 | 246 |
| 68 | 3-hydroxy-4-methylanilino | chloro | tetrahydrofuranyl | C = 55.9; H = 4.6; N = 20.0 | 344 | 246 |
| 69 | 3-hydroxy-2-methylanilino | chloro | tetrahydrofuranyl | C = 56.0; H = 4.7; N = 19.8 | 344 | 246 |
| 70 | 3,4-dimethylanilino | chloro | tetrahydrofuranyl | C = 59.8; H = 5.4; N = 20.0 | 342 | 344 |
| 71 | 2-hydroxy-3-methoxyanilino | chloro | tetrahydrofuranyl | C = 53.5; H = 4.5; N = 19.0 | 360 | 362 |

TABLE 1-continued

Compounds Prepared by the methods of Examples 1-5

[Structure: purine with R6 at 6-position, R2 at 2-position, Cyc on N9]

| | PURINE SUBSTITUENT | | | CHN ANALYSES | MS ANALYSES-ZMD | |
|---|---|---|---|---|---|---|
| | R6 | R2 | Cyc | [%] | [M − H]⁻ a) | [M + H]⁺ b) |
| 72 | 2-hydroxy-4-methoxyanilino | chloro | tetrahydrofuranyl | C = 53.4; H = 4.7; N = 19.1 | 360 | 362 |
| 73 | 4-hydroxy-3,5-dimethoxyanilino | chloro | tetrahydrofuranyl | C = 52.5; H = 4.7; N = 17.6 | 390 | 392 |
| 74 | 2,3-difluoroanilino | chloro | tetrahydrofuranyl | C = 51.7; H = 3.5; N = 19.6 | 350 | 352 |
| 75 | 2,4-difluoroanilino | chloro | tetrahydrofuranyl | C = 51.5; H = 3.4; N = 19.8 | 350 | 352 |
| 76 | 2,3,4-trifluoroanilino | chloro | tetrahydrofuranyl | C = 49.0; H = 3.1; N = 18.8 | 368 | 370 |
| 77 | 2,4,5-trifluoroanilino | chloro | tetrahydrofuranyl | C = 49.1; H = 3.1; N = 18.8 | 368 | 370 |
| 78 | 2,3-dichloroanilino | chloro | tetrahydrofuranyl | C = 46.6; H = 3.3; N = 17.9 | 382 | 384 |
| 79 | 2,4-dichloroanilino | chloro | tetrahydrofuranyl | C = 46.5; H = 3.2; N = 17.7 | 382 | 384 |

Example 6

2-Amino-6-(3-methoxytanilino)-9-(tetrahydropyran-2-yl or tetrahydrofuran-2-yl)purine To a suspension of 2-amino-6-chloro-9-(tetrahydropyran-2-yl or tetrahydrofuran-2-yl)purine (2.73 g; 0.01 mol, 2.59 g) and m-anisidine (1.23 g; 0.01 mol) in n-butanol (20 ml), triethylamine (3.5 ml; 0.025 mol) was added. The resulting thick suspension was stirred at 90° C. for 5 hours. The TLC showed the absence of the starting material and the presence of the desired product. The reaction mixture was then cooled to room temperature. The white precipitate was filtered off, rinsed with n-butanol (3×10 ml) and water (3×10 ml) and dried in the drying oven into constant weight. Yield: 2.19 g (85%). 1H-NMR, DMSO-$d_6$, TMS, ppm: 1.58m (2H, THP), 1.72-1.78m (1H, THP), 1.97d (2H, THP), 2.18-2.31m (1H, THP), 3.65-3.75m (1H, THP), 3.79s (3H, CH$_3$), 4.02d (1H, THP), 5.63d (1H, THP), 6.76dd, $J_a$=8.0 Hz, $J_b$=2.2 Hz (1H, Ar—H), 7.30t, J=8 Hz (1H, Ar—H), 7.56d, J=8 Hz (1H, Ar—H), 7.63s (1H, Ar—H), 7.66bs (2H, NH$_2$), 8.34s (1H, C8-H), 11.25s (1H, N6-H).

TABLE 2

Compounds Prepared by the Method of Example 6

[Structure: purine with R6 at 6-position, R2 at 2-position, Cyc on N9]

| | PURINE SUBSTITUENT | | | CHN ANALYSES | MS ANALYSES-ZMD | |
|---|---|---|---|---|---|---|
| | R6 | R2 | Cyc | [%] | [M − H]⁻ a) | [M + H]⁺ b) |
| 128 | anilino | amino | tetrahydropyranyl | C = 62.2; H = 6.2; N = 26.7 | 309 | 311 |
| 130 | 3-chloroanilino | amino | tetrahydropyranyl | C = 56.2; H = 5.2; N = 24.0 | 343 | 345 |
| 131 | 4-chloroanilino | amino | tetrahydropyranyl | C = 56.0; H = 5.0; N = 24.1 | 343 | 345 |
| 132 | 2-fluoroanilino | amino | tetrahydropyranyl | C = 58.9; H = 5.4; N = 25.2 | 327 | 329 |
| 133 | 3-fluoroanilino | amino | tetrahydropyranyl | C = 59.0; H = 5.4; N = 25.3 | 327 | 329 |
| 134 | 4-fluoroanilino | amino | tetrahydropyranyl | C = 59.0; H = 5.4; N = 25.2 | 327 | 329 |
| 135 | 2-hydroxyanilino | amino | tetrahydropyranyl | C = 59.5; H = 5.8; N = 25.1 | 325 | 327 |
| 136 | 3-hydroxyanilino | amino | tetrahydropyranyl | C = 59.1; H = 5.6; N = 25.5 | 325 | 327 |
| 137 | 4-hydroxyanilino | amino | tetrahydropyranyl | C = 59.2; H = 5.6; N = 25.4 | 325 | 327 |
| 138 | 2-methoxyanilino | amino | tetrahydropyranyl | C = 60.3; H = 6.0; N = 24.3 | 339 | 341 |
| 139 | 3-methoxyanilino | amino | tetrahydropyranyl | C = 60.2; H = 6.0; N = 24.2 | 339 | 341 |
| 140 | 4-methoxyanilino | amino | tetrahydropyranyl | C = 60.3; H = 6.0; N = 24.2 | 339 | 341 |
| 141 | 3,4-dimethylanilino | amino | tetrahydropyranyl | C = 64.0; H = 6.7; N = 24.4 | 337 | 339 |
| 142 | anilino | amino | tetrahydropyranyl | C = 61.2; H = 5.6; N = 28.0 | 295 | 297 |
| 144 | 3-chloroanilino | amino | tetrahydrofuranyl | C = 54.6; H = 4.6; N = 25.0 | 329 | 331 |
| 146 | 2-fluoroanilino | amino | tetrahydrofuranyl | C = 57.7; H = 4.9; N = 26..5 | 313 | 315 |

TABLE 2-continued

Compounds Prepared by the Method of Example 6

| | PURINE SUBSTITUENT | | | CHN ANALYSES | MS ANALYSES-ZMD | |
|---|---|---|---|---|---|---|
| | R6 | R2 | Cyc | [%] | [M − H]⁻ a) | [M + H]⁺ b) |
| 147 | 3-fluoroanilino | amino | tetrahydrofuranyl | C = 57.7; H = 4.8; N = 26..5 | 313 | 315 |
| 148 | 4-fluoroanilino | amino | tetrahydrofuranyl | C = 57.4; H = 4.9; N = 26..4 | 313 | 315 |
| 150 | 3-hydroxyanilino | amino | tetrahydrofuranyl | C = 57.8; H = 5.2; N = 26..8 | 311 | 313 |
| 152 | 2-methoxyanilino | amino | tetrahydrofuranyl | C = 59,1; H = 5,6; N = 25..4 | 325 | 327 |
| 153 | 3-methoxyanilino | amino | tetrahydrofuranyl | C = 59,4; H = 5,7; N = 25..5 | 325 | 327 |
| 154 | 4-methoxyanilino | amino | tetrahydrofuranyl | C = 59,1; H = 5,6; N = 25..5 | 325 | 327 |
| 155 | 3,4-dimethylanilino | amino | tetrahydrofuranyl | C = 63,3; H = 6,3; N = 25..6 | 323 | 325 |

Example 7

2-Fluoro-6-(3-methoxyanilino)-9-(tetrahydropyran-2-yl or tetrahydrofuran-2-yl)purine This compound was prepared by the reaction of 2-fluoro-6-chloro-9-(tetrahydropyran-2-yl or tetrahydrofuran-2-yl)purine (2.73 g; 0.01 mol, 2.59 g), m-anisidine (1.23 g; 0.01 mol) and triethylamine (3.5 ml; 0.025 mol) in n-butanol (20 ml) at 90° C. for 4 hours. The reaction mixture was then cooled to the room temperature. The white precipitate was filtered off, rinsed with n-butanol (3×10 ml) and water (3×10 ml) and dried in the drying oven into constant weight. Yield: 5.55 g (61%) of yellowish crystalline powder. TLC (chloroform-methanol; 85:15): one single spot. HPLC purity: 99+%. 1H-NMR, DMSO-$d_6$, TMS, ppm: 1.58m (2H, THP), 1.72-1.75m (1H, THP), 1.97d (2H, THP), 2.20-2.32m (1H, THP), 3.65-3.72m (1H, THP), 3.76s (3H, CH$_3$), 4.01d (1H, THP), 5.60d (1H, THP), 6.69dd, J$_a$=8.1 Hz, J$_b$=2.2 Hz (1H, Ar—H), 7.26t, J=8.1 Hz (1H, Ar—H), 7.45dd, J$_a$=8.1 Hz, J$_b$=2.2 Hz (1H, Ar—H), 7.53t, J=2.2 Hz (1H, Ar—H), 8.51s (1H, C8H), 10.36bs (1H, N6H).

TABLE 3

Compounds Prepared by the Method of Example 7

| | PURINE SUBSTITUENT | | | CHN ANALYSES | MS ANALYSES-ZMD | |
|---|---|---|---|---|---|---|
| | R6 | R2 | Cyc | [%] | [M − H]⁻ a) | [M + H]⁺ b) |
| 80 | anilino | fluoro | tetrahydropyranyl | C = 61.6; H = 5.2; N = 22.2 | 312 | 314 |
| 81 | 2-chloroanilino | fluoro | tetrahydropyranyl | C = 55..5; H = 4.4; N = 20.0 | 346 | 348 |
| 82 | 3-chloroanilino | fluoro | tetrahydropyranyl | C = 55..5; H = 4.4; N = 20.0 | 346 | 348 |
| 83 | 4-chloroanilino | fluoro | tetrahydropyranyl | C = 55..5; H = 4.4; N = 19.8 | 346 | 348 |
| 84 | 2-fluoroanilino | fluoro | tetrahydropyranyl | C = 58.3; H = 4.7; N = 20.7 | 330 | 332 |
| 85 | 3-fluoroanilino | fluoro | tetrahydropyranyl | C = 58.2; H = 4.8; N = 20.9 | 330 | 332 |
| 86 | 4-fluoroanilino | fluoro | tetrahydropyranyl | C = 58.3; H = 4.7; N = 20.8 | 330 | 332 |
| 87 | 2-hydroxyanilino | fluoro | tetrahydropyranyl | C = 58.5; H = 5.1; N = 20.9 | 328 | 330 |
| 88 | 3-hydroxyanilino | fluoro | tetrahydropyranyl | C = 58.7; H = 5.2; N = 21.0 | 328 | 330 |
| 89 | 4-hydroxyanilino | fluoro | tetrahydropyranyl | C = 58.6; H = 5.2; N = 21.0 | 328 | 330 |
| 90 | 2-methoxyanilino | fluoro | tetrahydropyranyl | C = 59.7; H = 5.4; N = 20.1 | 342 | 244 |
| 91 | 3-methoxyanilino | fluoro | tetrahydropyranyl | C = 59.9; H = 5.6; N = 19.9 | 342 | 244 |
| 92 | 4-methoxyanilino | fluoro | tetrahydropyranyl | C = 59.7; H = 5.5; N = 20.0 | 342 | 244 |
| 93 | 3,4-dimethoxyanilino | fluoro | tetrahydropyranyl | C = 58.4; H = 5.5; N = 18.3 | 372 | 374 |
| 94 | 2,5-dimethoxyanilino | fluoro | tetrahydropyranyl | C = 58.6; H = 5.4; N = 18.4 | 372 | 374 |
| 95 | 3,4-dihydroxyanilino | fluoro | tetrahydropyranyl | C = 55.8; H = 4.8; N = 19.9 | 344 | 346 |
| 96 | 2,5-dihydroxyanilino | fluoro | tetrahydropyranyl | C = 55.7; H = 4.7; N = 20.0 | 344 | 346 |
| 97 | 2-chloro-5-methoxyanilino | fluoro | tetrahydropyranyl | C = 54.2; H = 4.7; N = 18.2 | 376 | 378 |

TABLE 3-continued

Compounds Prepared by the Method of Example 7

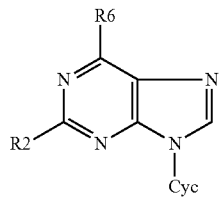

| | PURINE SUBSTITUENT | | | CHN ANALYSES | MS ANALYSES-ZMD | |
|---|---|---|---|---|---|---|
| | R6 | R2 | Cyc | [%] | [M − H]⁻ a) | [M + H]⁺ b) |
| 98 | 2-methoxy-3-chloroanilino | fluoro | tetrahydropyranyl | C = 54.3; H = 4.7; N = 18.2 | 376 | 378 |
| 99 | 3-ethoxyanilino | fluoro | tetrahydropyranyl | C = 60.6; H = 5.7; N = 19.2 | 356 | 358 |
| 100 | 2-hydroxy-5-methylanilino | fluoro | tetrahydropyranyl | C = 59.7; H = 5.4; N = 20.2 | 342 | 344 |
| 101 | 3-hydroxy-4-methylanilino | fluoro | tetrahydropyranyl | C = 59.6; H = 5.4; N = 20.1 | 342 | 344 |
| 102 | 3-hydroxy-2-methylanilino | fluoro | tetrahydropyranyl | C = 59.7; H = 5.4; N = 20.1 | 342 | 344 |
| 103 | 3,4-dimethylanilino | fluoro | tetrahydropyranyl | C = 62,6; H = 6,1; N = 20.4 | 340 | 342 |
| 104 | anilino | fluoro | tetrahydrofuranyl | C = 59.9; H = 4.9; N = 23.2 | 298 | 300 |
| 106 | 3-chloroanilino | fluoro | tetrahydrofuranyl | C = 54..3; H = 4.1; N = 20.8 | 332 | 334 |
| 109 | 3-fluoroanilino | fluoro | tetrahydrofuranyl | C = 57.0; H = 4.3; N = 21.7 | 316 | 318 |
| 112 | 3-hydroxyanilino | fluoro | tetrahydrofuranyl | C = 57.4; H = 4.6; N = 21.9 | 314 | 316 |
| 114 | 2-methoxyanilino | fluoro | tetrahydrofuranyl | C = 58.8; H = 5.1; N = 21.0 | 328 | 330 |
| 115 | 3-methoxyanilino | fluoro | tetrahydrofuranyl | C = 58.7; H = 5.1; N = 21.1 | 328 | 330 |
| 116 | 4-methoxyanilino | fluoro | tetrahydrofuranyl | C = 58.7; H = 5.2; N = 21.1 | 328 | 330 |
| 117 | 3,4-dimethoxyanilino | fluoro | tetrahydrofuranyl | C = 58.2; H = 5.5; N = 18.5 | 358 | 360 |
| 120 | 2,5-dihydroxyanilino | fluoro | tetrahydrofuranyl | C = 54.5; H = 4.4; N = 20.8 | 330 | 332 |
| 121 | 2-chloro-5-methoxyanilino | fluoro | tetrahydrofuranyl | C = 53.1; H = 4.2; N = 19.0 | 362 | 364 |
| 122 | 2-methoxy-3-chloroanilino | fluoro | tetrahydrofuranyl | C = 53.0; H = 4.3; N = 19.1 | 362 | 364 |
| 123 | 3-ethoxyanilino | fluoro | tetrahydrofuranyl | C = 59.6; H = 5.4; N = 20.1 | 342 | 344 |
| 124 | 2-hydroxy-5-methylanilino | fluoro | tetrahydrofuranyl | C = 58.5; H = 5.0; N = 21.0 | 328 | 330 |
| 125 | 3-hydroxy-4-methylanilino | fluoro | tetrahydrofuranyl | C = 58.4; H = 5.0; N = 20.9 | 328 | 330 |
| 126 | 3-hydroxy-2-methylanilino | fluoro | tetrahydrofuranyl | C = 58.5; H = 5.0; N = 20.9 | 328 | 330 |
| 127 | 3,4-dimethylanilino | fluoro | tetrahydrofuranyl | C = 62.4; H = 5.6; N = 21.5 | 326 | 328 |

Example 8

2-Methylthioxanthine

Dimethyl sulfate (77 g, 58 ml) was added dropwise into a freshly prepared solution of 2-thioxanthine (103 g, 0.613 mol) in 2 M NaOH (613 ml) and water (245 ml), temperature was maintained between 25 and 40° C. Reaction mixture was stirred for another hour and then left to stand overnight at room temperature. The dark red liquid was then filtered and the product was precipitated by concentrated acetic acid, filtered and re-crystallized from hot water (1500 ml) with active carbon. The product was crystallized at −10° C., filtered and dried at 95° C. for 3 h, and then over phosphorus (V) oxide to constant weight. Yield: 48%. HPLC purity: 80%.

Example 9

2-Methylthio-6-chloropurin

2-Methylthioxanthine (65 g) was mixed with POCl₃ (975 ml) and N,N-diethylaniline (97.5 ml). Reaction mixture was then refluxed at mechanical stirring for 90 minutes. Excess POCl₃ was removed by vacuum rotary evaporator at 55-60° C. and the residue was mixed with ice (0° C., 1.75 kg) for 10 minutes (until total hydrolysis of POCl₃ was achieved). The product was then extracted by ethyl acetate (4×2.5 l). The extracts were washed with water and evaporated to dryness, yielding a dark brown solid. The raw product was re-crystallized from ethanol with active carbon and dried to constant weight over phosphorus (V) oxide. Yield: 23.6 g (33%). HPLC purity: 99%. TLC (chloroform/methanol, 9/1)—no impurities.

Example 10

2-Methylthio-6-anilinopurine 2-methylthio-6-chloropurine (10 g, 50 mmol), aniline (7.7 g, 63 mmol) and triethylamine (35 ml, 250 mmol) were refluxed in butanol (400 ml) for 2 h. Butanol was removed in vacuo and water (290 ml) added to the cooled residue. pH was adjusted to 8.0, the mixture was left at −16° C. overnight. Filtration and drying over phosphorus pentoxide in vacuo gave 10 g crude yellow-green product. The product was chromatographically purified (250 g silica, Fisons, chloroform); eluted with chloroform/methanol (97/3, v/v). Appropriate fractions were dried in vacuo, re-crystallised from ethanol with decolourisation by active carbon. After dryig to constant weight over $P_2O_5$, yield 5.76 g, (46%), HPLC purity >98%. TLC: chloroform/methanol (9/1, v/v), no contaminants.

Example 11

2-Methylthio-6-anilino-9-(tetrahydropyran-2-yl) purin 3,4-dihydropyrane (10 ml, 0.1 mol) and trifluoroacetic acid (10 ml, 0.13 mol) were added in this order to the suspension of 2-methylthio-6-anilinopurine (10 g; 0.039 mol) in dioxane (250 ml). The reaction mixture was then heated to 60° C., and stirred at this temperature for 2 hours. Then the reaction mixture was cooled to 25° C. and neutralized with 7 M methanolic ammonia at cooling. Dioxane was distilled off under vacuum and the residue was worked up with ethyl acetate (200 ml) and water (200 ml). Aqueous phase was extracted by ethyl acetate (2×50 ml). Combined organic extracts were shaked with saline (30 ml), dried with dehydrated sodium sulfate and evaporater on rotary vacuum evaporator. Yield: 13.4 g (quant.) of beige amorphous product. HPLC purity: 93%+. The raw product was re-crystallized from the mixture ethyl acetate-petrolether (1:10); yield: 10.3 g (77.0%) of off-white product. HPLC purity: 97%+. 1H-NMR, DMSO-$d_6$, TMS, ppm: 1.58m (2H, THP), 1.72-1.78m (1H, THP), 1.98d (2H, THP), 2.18-2.31m (1H, THP), 2.49s (3H, $CH_3S$), 3.65-3.75m (1H, THP), 4.02d (1H, THP), 5.63d (1H, THP), 6.69dd, $J_a$=8.2 Hz, $J_b$=2.2 Hz (1H, Ar—H), 7.29t, J=8.2 Hz, 1H (Ar—H), 7.46dd, $J_a$=8.2 Hz, $J_b$=2.2 Hz (1H, Ar—H), 7.67t, J=2.2 Hz (1H, Ar—H), 9.00s (1H, C8H), 10.74s (1H, N6H).

TABLE 5

Compounds Prepared by the Method of Examples 8-11

| | PURINE SUBSTITUENT | | | CHN ANALYSES | MS ANALYSES-ZMD | |
| --- | --- | --- | --- | --- | --- | --- |
| | R6 | R2 | Cyc | [%] | [M − H]− a) | [M + H]+ b) |
| 157 | anilino | methylthio | tetrahydropyranyl | C = 60.0; H = 5.7; N = 20,3 | 340 | 342 |
| 158 | 3-chloroanilino | methylthio | tetrahydropyranyl | C = 54.6; H = 4.9; N = 18.2 | 374 | 376 |
| 159 | 3-fluoroanilino | methylthio | tetrahydropyranyl | C = 56.9; H = 5.1; N = 19.4 | 358 | 360 |
| 160 | 4-fluoroanilino | methylthio | tetrahydropyranyl | C = 56.9; H = 5.2; N = 19.4 | 358 | 360 |
| 161 | 3-hydroxyanilino | methylthio | tetrahydropyranyl | C = 57.5; H = 5.5; N = 19.2 | 356 | 358 |
| 162 | 2-methoxyanilino | methylthio | tetrahydropyranyl | C = 58.5; H = 5.7; N = 18.6 | 370 | 372 |
| 163 | 3-methoxyanilino | methylthio | tetrahydropyranyl | C = 58.4; H = 5.8; N = 18.7 | 370 | 372 |
| 164 | 4-methoxyanilino | methylthio | tetrahydropyranyl | C = 58.5; H = 5.8; N = 18.7 | 370 | 372 |
| 165 | 3,4-dimethoxyanilino | methylthio | tetrahydropyranyl | C = 56.5; H = 5.9; N = 17.2 | 400 | 402 |
| 166 | 2,5-dimethoxyanilino | methylthio | tetrahydropyranyl | C = 56.7; H = 5.1; N = 17.4 | 400 | 402 |
| 167 | 2-chloro-5-methoxyanilino | methylthio | tetrahydropyranyl | C = 53.5; H = 5.1; N = 17.0 | 404 | 406 |
| 168 | 2-methoxy-3-chloroanilino | methylthio | tetrahydropyranyl | C = 53.6; H = 5.1; N = 17.1 | 404 | 406 |
| 169 | anilino | methylthio | tetrahydrofuranyl | C = 58.9; H = 5.3; N = 21,1 | 326 | 328 |
| 170 | 2-methoxyanilino | methylthio | tetrahydrofuranyl | C = 57.4; H = 5.5; N = 19.2 | 356 | 358 |
| 171 | 3-methoxyanilino | methylthio | tetrahydrofuranyl | C = 57.1; H = 5.5; N = 19.4 | 356 | 358 |
| 172 | 4-methoxyanilino | methylthio | tetrahydrofuranyl | C = 57.2; H = 5.4; N = 19.3 | 356 | 358 |

Example 12

2-Bromo-6-(methoxyanilino)-9-(tetrahydropyran-2-yl or tetrahydrofuran-2-yl)purine 2-Bromo-6-(methoxyanilino)-9-(tetrahydropyran-2-yl or tetrahydrofuran-2-yl)purine was prepared in a similar manner to example 5 by the reaction of 2-bromo-6-chloro-(tetrahydropyran-2-yl or tetrahydrofuran-2-yl)purine (2.73 g; 0.01 mol, 2.59 g) and m-anisidine (molar ratio 1:1) in the presence of triethylamine (2.5 eq.) in n-propanol at 90° C. for 5 hours. After cooling to room temperature the resulting white precipitate was filtered off, washed with cold n-propanol and water and dried in desiccator into constant weight. Yield: 69%. Crude product was purified by crystallization from methanol and free base was obtained by treatment of hydrobromide with 10% aqueous ammonia. HPLC purity: 98+%.

TABLE 6

Compounds Prepared by the Method of Example 12

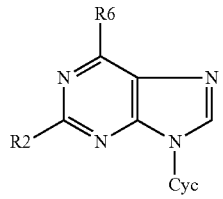

| | PURINE SUBSTITUENT | | | CHN ANALYSES | MS ANALYSES-ZMD | |
|---|---|---|---|---|---|---|
| | R6 | R2 | Cyc | [%] | [M − H]− a) | [M + H]+ b) |
| 173 | Anilino | bromo | tetrahydropyranyl | C = 51.6; H = 4.4; N = 21.1 | 373 | 375 |
| 174 | 2-chloroanilino | bromo | tetrahydropyranyl | C = 47.4; H = 3.8; N = 16.9 | 407 | 409 |
| 175 | 3-chloroanilino | bromo | tetrahydropyranyl | C = 47.2; H = 3.8; N = 17.0 | 407 | 409 |
| 176 | 2-fluoroanilino | bromo | tetrahydropyranyl | C = 49.3; H = 4.0; N = 17.7 | 391 | 393 |
| 177 | 3-fluoroanilino | bromo | tetrahydropyranyl | C = 49.1; H = 3.9; N = 17.6 | 391 | 393 |
| 178 | 3-methoxyanilino | bromo | tetrahydropyranyl | C = 50.7; H = 4.6; N = 17.0 | 403 | 405 |
| 179 | 3-hydroxyanilino | bromo | tetrahydropyranyl | C = 49.5; H = 4.2; N = 17.9 | 389 | 391 |
| 180 | Anilino | bromo | tetrahydrofuranyl | C = 50.2; H = 4.0; N = 19.1 | 359 | 361 |
| 181 | 3-chloroanilino | bromo | tetrahydrofuranyl | C = 45.8; H = 3.3; N = 17.6 | 393 | 395 |
| 182 | 2-fluoroanilino | bromo | tetrahydrofuranyl | C = 48.1; H = 3.6; N = 18.2 | 377 | 379 |
| 183 | 3-fluoroanilino | bromo | tetrahydrofuranyl | C = 48.0; H = 3.5; N = 18.3 | 377 | 379 |
| 184 | 3-methoxyanilino | bromo | tetrahydrofuranyl | C = 49.6; H = 4.3; N = 17.6 | 389 | 391 |
| 185 | 3-hydroxyanilino | bromo | tetrahydrofuranyl | C = 48.0; H = 3.8; N = 18.5 | 375 | 377 |

Example 13

Agonistic Activity of 2-chloro-6-(3-methoxyanilino)-9-(tetrahydropyran-2-yl)purine (Compound 12) and 2-fluoro-6-(3-methoxyanilino)-9-(tetrahydropyran-2-yl)purine (Compound 91) on Cytokinin Receptors

*Escherichia coli* strains KMI001 harbouring the plasmid pIN-III-AHK4 or pSTV28-AHK3 were grown overnight at 25° C. in M9 media enriched with 0.1% casamino acids to $OD_{600}$~1. The preculture was diluted 1:600 in 1 ml M9 medium containing 0.1% casamino acids and 1 μL stock solution of either the tested compound ($10^{-7}$ M-$5 \times 10^{-5}$ M) or solvent control (DMSO, ethanol, methanol) were added. The cultures were further grown at 25° C. in microtiter plate, 200 μL per well. Incubation times of 17 h and 28 h were found to be optimal for CRE1/AHK4 and AHK3, respectively. The cultures were centrifuged and 50 μL aliquots of the supernatant were transferred to microtiter plate containing 2 μL 50 mM 4-methyl umbelliferyl galactoside which was subsequently incubated for 1 h at 37° C. The reaction was stopped by adding 100 μL 0.2 M $Na_2CO_3$. Fluorescence was measured using a Fluoroscan Ascent (Labsystems, Finland) at the excitation and emission wavelengths of 365 and 460 nm, respectively. The $OD_{600}$ of remaining culture was determined and β-galactosidase activity was calculated as nmol 4-methylumbelliferone×$OD_{600}^{-1} \times h^{-1}$.

The curves shown in FIG. 1 show that compared to the cytokinin trans-zeatin (tZ) the novel compound 12 have very low ability to activate the cytokinin receptors AHK3 and CRE1/AHK4, and compound 91 do not activate any of the receptors. This indicates that if a cytokinin-like activity is observed after application of the compounds 12 and 91, it is resulting from mechanism different from direct activation of the cytokinin receptor pathway. The comparison with structurally related CKX inhibitors INCYDE (2-chloro-6-(3-methoxyanilino)purine) and INCYDE-F (2-fluoro-6-(3-methoxyanilino)purine) also indicates that the novel compounds have original mode of action different from the CKX inhibitors INCYDE and INCYDE-F.

Example 14

Induction of Cytokinin Reporter ARR5 Expression after Application of of 2-chloro-6-(3-methoxyanilino)-9-(tetrahydropyran-2-yl)purine (Compound 12)

Cytokinins induce in *Arabidopsis* transcription of gene ARR5, a member of A-type response regulator family classified as cytokinin primary response genes being expressed down-stream of sensing by cytokinin receptors. We cultivated transgenic *Arabidopsis* plants harbouring $P_{ARR5}$::GUS reporter (D'Agostino et al. Plant Physiol. 124: 1706-1717, 2000) in MS medium containing cytokinin BAP, CKX inhibitor INCYDE and novel compounds 12 and 91 in concentrations 0.01, 0.1, 1, 5, 10 μM; DMSO (0.1%) was tested as solvent control. Seeds were surface-sterilized in 70% ethanol and then placed into wells of 6-well microtiter plate (TPP, Switzerland) containing 3 mL of MS medium in each well. After sowing plates were pretreated in dark at 4° C. to synchronize the germination of the seeds. Then the plates were transferred to growth chamber (22° C., 16 h light/8 h dark) and after 2-3 days after germination the tested compounds were applied directly into the media. The plants were incubated with the tested compounds for 17 h. Quantitative estimation of the level of ARR5:GUS gene induction was done according to method published by Romanov et al. (Romanov et al. FEBS Letters 515: 39-43, 2002). After extraction of proteins the GUS activity was determined using incubation with fluorogenic substrate MUG (4-methylumbelliferyl glucuronid; 1 h, 37° C.) and then fluorescence 365 nm and 460 nm (excitation and emission wavelengths) was recorded, as described in detail by Spíchal et al. (Spíchal et al. Plant and Cell Physiology 45: 1299-1305, 2004).

Figure 2:
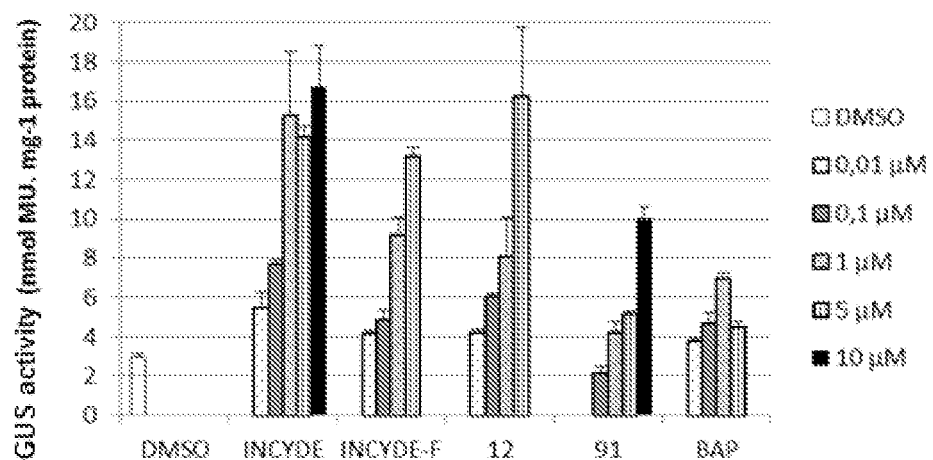
FIG. 2 shows differences in dose-dependent activation of cytokinin responsive reporter gene ARR5:GUS (Romanov et al., 2002) by cytokinin 6-benzylaminopurine (BAP), inhibitors of cytokinin oxidase-dehydrogenase INCYDE and INCYDE-F and representatives of the novel derivatives compound 12 and 91. Bars represent means of three repetitions, error bars represent SD.

Quantitative assay showed compound 12 and 91 dose-dependent induction of ARR5:GUS expression (FIG. 2). Taking into account that the compound 12 activated cytokinin receptors only weakly and compound 91 fails to activate cytokinin receptors at all (see FIG. 1 from previous example), it can be concluded that these compounds do not act as cytokinins directly, but after their application to the plants cytokinin pathway is activated indirectly. Comparison with activities of CKX inhibitors INCYDE (2-chloro-6-(3-methoxyanilino)purine) and INCYDE-F (2-fluoro-6-(3-methoxyanilino)purine) (FIG. 2) also documents that compounds 12 and 91 have different mode of action than the mentioned structuraly related CKX inhibitors.

Example 15

Inhibition of Cytokinin Oxidase/Dehydrogenase Activity $IC_{50}$ measurements were done using the assay in microtitre plate. Each well contained 100 μL of PMS/MTT [phenazine methosulfate/3-(4,5-dimethylthiazol-2-yl)-2,5-diphenyltetrazolium bromide] reaction mixture (final concentrations: 0.1 M $KH_2PO_4$, pH 7.4, 1 mM MTT, 0.2 mM PMS) containing the tested compound ($3 \times 10^{-7}$ M-$3 \times 10^{-4}$ M) and 30 μM $N^6$-isopentenyladenine (iP) as a substrate. 100 μL of cell-free growth medium of S. cerevisiae strain 23344c ura⁻ harboring the plasmid pYES2-AtCKX2 was directly used as a source of AtCKX2. Plates were incubated in the dark for 30 min at 37° C. and the enzymatic reaction was stopped by 25 μL of 35% acetic acid. The absorbance at 578 nm was measured using spectrophotometer Tecan. Absorbance of the sample without iP was subtracted.

The $IC_{50}$ value, the compound concentration that inhibits the enzyme activity to 50%, was calculated from the obtained dose response curves. The values shown in Table 7 are means of three replicates and the entire test was repeated at least twice. More potent compounds than thidiazuron have $IC_{50}$ values lower than thidiazuron. Compound 12 is an effective inhibitor of AtCKX2 activity, app. 3-times stronger that thidiazuron and only app. 3-times weaker than the structuraly related compound INCYDE (2-chloro-6-(3-methoxyanilino)purine). It indicates that compound 12 can directly act as an original inhibitor of CKX activity in plant tissues and thus increase the endogenous cytokinin levels. On the other hand the visible difference in activity of compound 91 and its structurally related CKX inhibitor INCYDE-F (2-fluoro-6-(3-methoxyanilino)purine) indicates that biological activity of compound 91 is caused also by other mechanism different from CKX inhibition.

TABLE 7

The effect of novel compounds on inhibition of recombinant AtCKX2

| No. | Tested compound | | | IC50 ($\mu mol \cdot L^{-1}$) |
|---|---|---|---|---|
| | R6 | R2 | R9 | |
| | thidiazuron | | | 55 |
| | INCYDE | | | 6.7 |
| | INCYDE-F | | | 5.2 |
| 12 | 3-methoxyanilino | chloro | tetrahydropyr | 19.5 |
| 91 | 3-methoxyanilino | fluoro | tetrahydropyr | 380 |

Example 16

Figure 3:
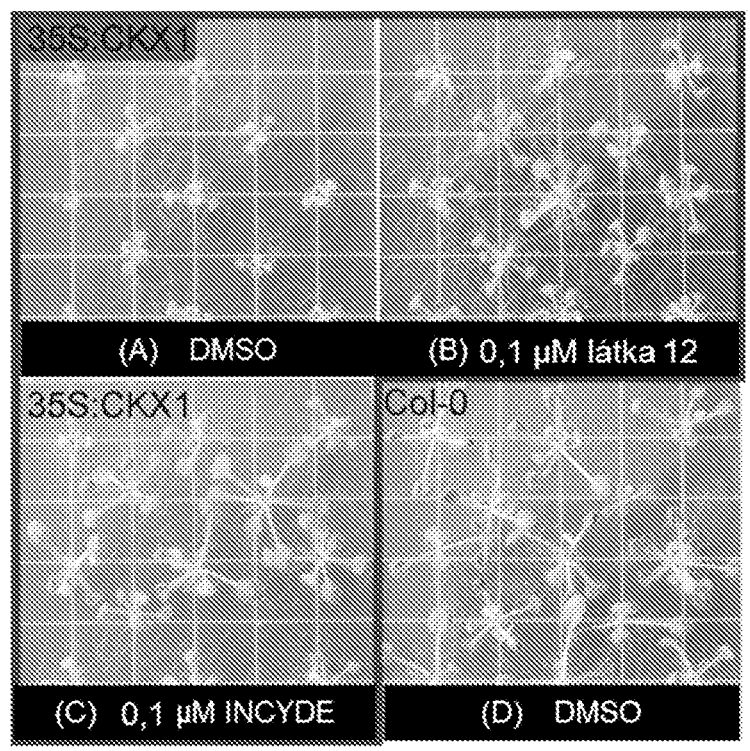
FIG. 3 shows comparison of the effect of compound 12 and CKX inhibitor INCYDE application on complementation of wild-type phenotype of AtCKX1 *Arabidopsis* seedlings. (A) AtCKX1 control, (B) AtCKX1 cultivated on 0.1 μM compound 12, (C) AtCKX1 cultivated on 0.1 μM INCYDE, (D) control plant with wild-type phenotype.
Figure 4:
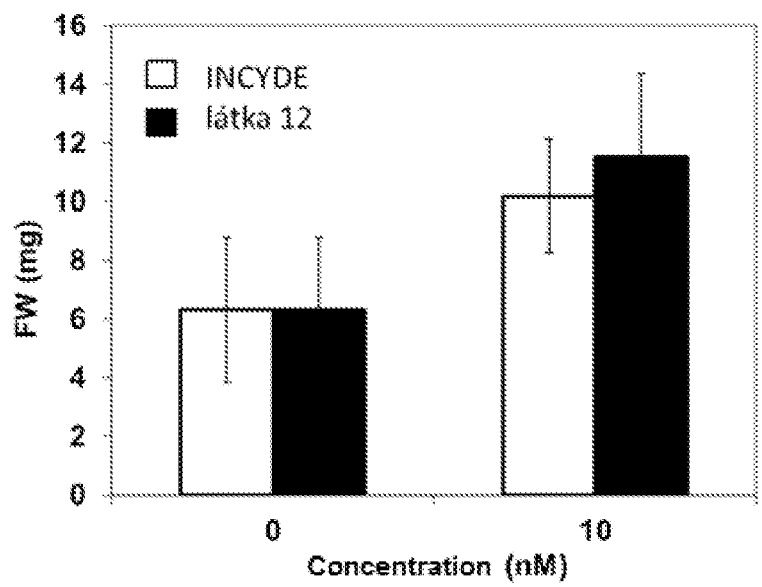
FIG. 4 illustrates similar dose-dependent effect of the compound 12 and structurally related CKX inhibitor INCYDE on complementation of wild-type shoot phenotype of AtCKX1 plants. Bars represent means of fresh weight of rosettes of treated plants, error bars indicate SD (n=30).

In Vitro Effect of 2-chloro-6-(3-methoxyanilino)-9-(tetrahydropyran-2-yl) purine (Compound 12) on Shoot and Root Growth of Cytokinin Deficient *Arabidopsis* Plants To prove that compound 12 has positive effect on plant growth and development through inhibition of the cytokinin degradation enzyme CKX (thus through stabilization of plant endogenous cytokinin levels) and that the phenotype complementation effect is not general effect of exogenously applied cytokinin, CKX1 overproducing (35S:CKX1) *Arabidopsis* seedlings were grown in vitro on a standard MS medium containing 0.1 μM cytokinin BAP, the same concentration of compound 12 and the same concentration of CKX inhibitor INCYDE (2-chloro-6-(3-methoxyanilino)purine). FIG. 3 clearly shows that the application of compound 12 as well as CKX inhibitor INCYDE released the plants from growth inhibition caused by decreased cytokinin level and led to restauration of wild type shoot phenotype in a dose dependent manner (FIG. 4). Such an effect cannot be reached by application of the cytokinin BAP (WO 2008/CZ00074).

Figure 5:
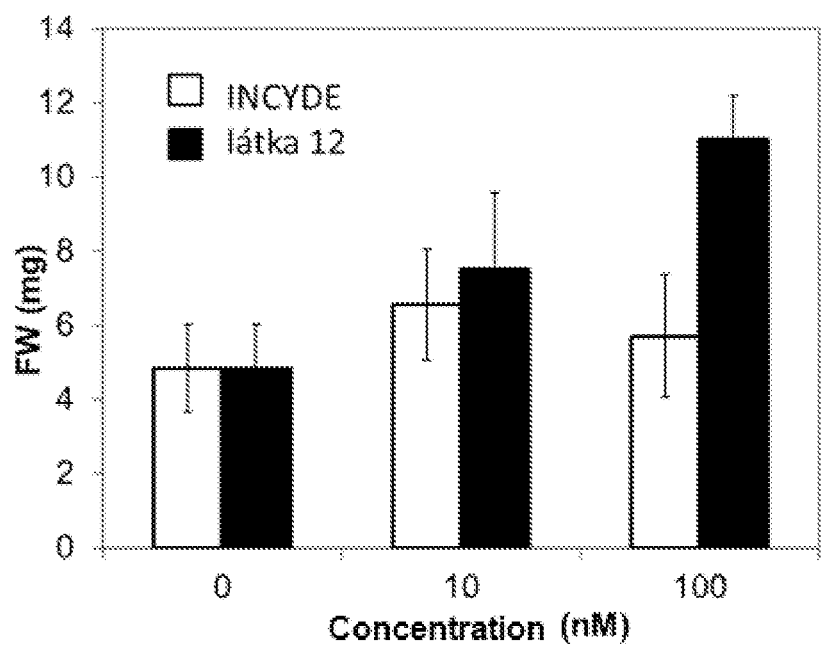
FIG. 5 illustrates clear difference in effect of the compound 12 and structurally related CKX inhibitor INCYDE on stimulation of root biomass of AtCKX1 plants. Bars represent means of fresh weight of roots of treated plants, error bars indicate SD (n=30).

To further prove that the action of the compound 12 is different from structurally similar CKX inhibitor INCYDE (2-chloro-6-(3-methoxyanilino)purine), effect of the both compounds on the root growth of the 35S:CKX1 *Arabidopsis* plants was assessed. As shown in FIG. 5 whereas INCYDE did not influence the root biomass in the tested concentration range, compound 12 exert strong dose-dependent positive effect. Constitutive overexpression of CKX in 35S:CKX1 plants leads to enhanced root growth. If CKX inhibitor can restore WT phenotype, it is expected that inhibition of the CKX activity in 35S:AtCKX1 plants should thus have no effect or inhibit their root growth. Such observation was done in case of INCYDE, but not compound 12. Thus, despite the fact that compound 12 is capable of inhibition of CKX activity (example 16) the result described in this example clearly indicates that the biological activity of compound 12 is different from specific CKX inhibitor INCYDE.

Example 17

Figure 6:
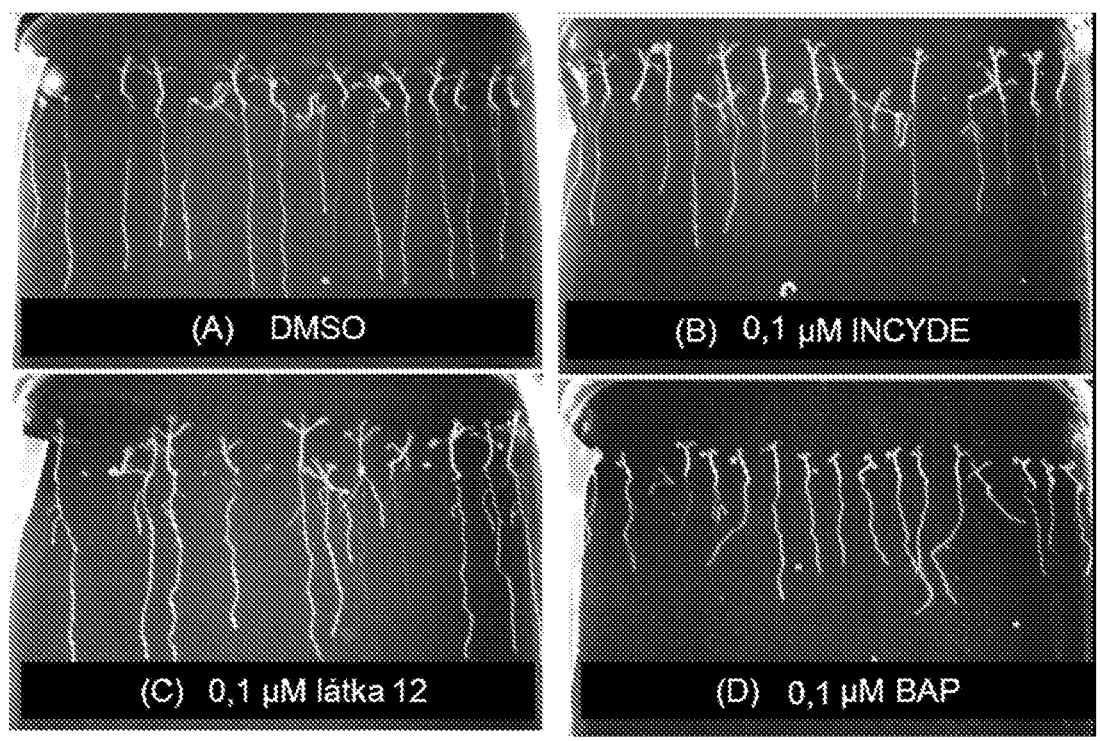
FIG. 6 shows comparison of the effect of 0.1 μM CKX inhibitor INCYDE (B), 0.1 μM compound 12 (C) and cytokinin BAP (D) on wild-type *Arabidopsis* root growth and development (A) in vitro.

In Vitro Effect of 2-chloro-6-(3-methoxyanilino)-9-tetrahydropyran-2-ylpurine (Compound 12) on Root Growth of Wild-Type *Arabidopsis* Plants As shown in previous example presence of compound 12 in the growth medium has positive effect on the root growth of cytokinin-deficient *Arabidopsis* plants. This effect was further studied using wild-type *Arabidopsis* plants and compared with biologically and structurally relevant compounds, a cytokinin BAP and a CKX inhibitor INCYDE. 35S:CKX1 *Arabidopsis* seedlings were grown in vitro on a standard MS medium containing 0.1 μM cytokinin BAP, the same concentration of compound 12 and the same concentration of CKX inhibitor INCYDE (2-chloro-6-(3-methoxyanilino)purine). FIG. 6 clearly shows that whereas cytokinin BAP and CKX inhibitor INCYDE expectedly inhibited root growth, application of compound 12 showed positive effect on the root length and lateral branching.

Example 18

Effect of 2-chloro-6-(3-methoxyanilino)aminopurine (Compound 12) on Leaf Chlorophyll Degradation in Shoot Rosettes of *Arabidopsis*

Figure 7:
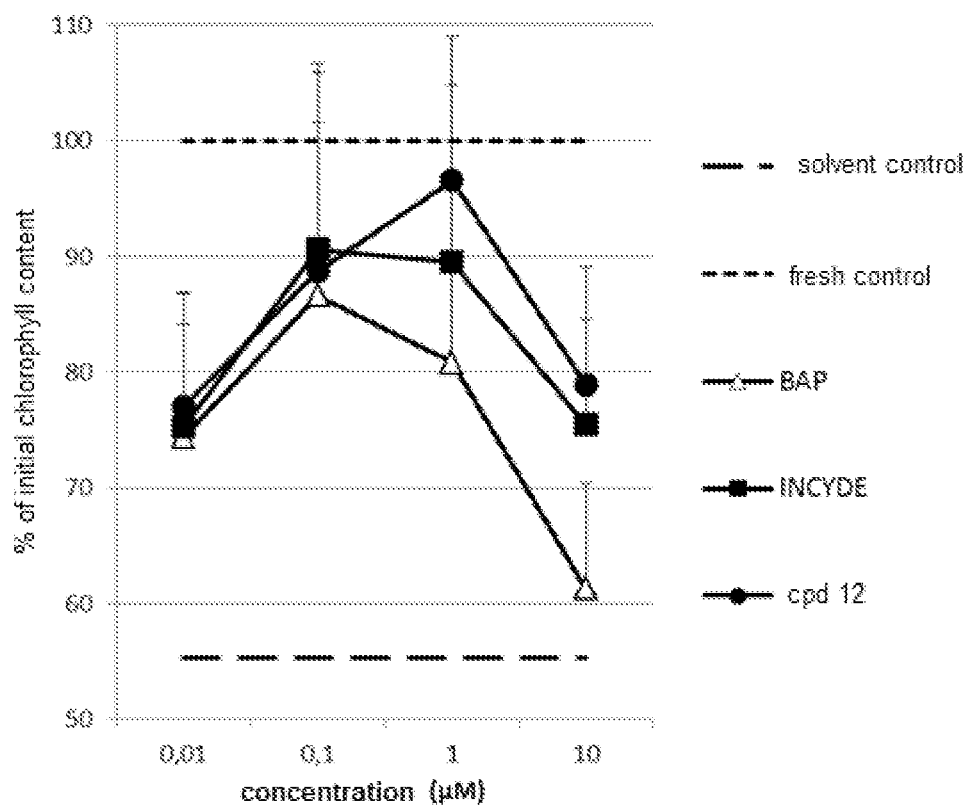
FIG. 7 shows difference in dose-dependent effect of CKX inhibitor INCYDE, compound 12 and cytokinin BAP on retention of chlorophyll in rosettes incubated for 6 days in the dark in the presence of the tested compounds. Values represent means from six replicates, error bars represent SD.

The effect of the compound 12 on retention of chlorophyll in the dark treated plants was tested using app. 18 DAG (days after germination) old *Arabidopsis* plants grown in vitro on standard MS medium (16 h/8 h light/dark regime, light intensity 120 $\mu mol \cdot m^{-1} \cdot s^{-1}$). Shoots of the plants were excised from the roots and the whole rossetes were placed into 6-well plate (one rosete per well) into water (3 mL per well) containing 0.01% DMSO (solvent control), or compound 12, cytokinin BAP and CKX inhibitor INCYDE (2-chloro-6-(3-methoxyanilino)purine), in concentrations of 0.01, 0.1, 1 and 10 μM. The plates were then incubated in the dark for 6 days at 25° C. After incubation chlorophyll from each rosette was extracted into 1.8 mL of 80% ethanol, during 30 min of heating to 80° C. The chlorophyll content in extracts was measured spectrofotometricaly at 665 nm. As shown in FIG. 7, compound 12 showed highest activity in 1 μM concentration exceeding that of both cytokinin BAP and CKX inhibitor INCYDE. In this concentration the rosettes kept around 95% of chlorophyll.

Example 19

Effect of Drenching Application of Compound 12 on Morphological and Yield Traits of *Arabidopsis*

Presence of the compound 12 in the growth medium of in vitro grown cytokinin-deficient *Arabidopsis* plants showed positive effect on both shoot and root growth (see Example 22 and 23). To test the effect on wild-type plants *Arabidopsis* (ecotype Col-0) was grown in soil in controlled conditions in a growth chambre (16 hours light/8 hours dark; light intensity 120 $\mu mol \cdot m^{-1} \cdot s^{-1}$; 22° C.; 60% humidity). In the stage of app. the middle of the principal growth stage 1 and the beginning of principal growth stage 5 (according to *Arabidopsis* growth stages described by Boyes et al., 2001) 1-10 mL of the compound 12 was applied regulary every third day in 0.1 and 1 μM concentration in different application rates (experiment 1-1 mL of 1 μM compound 12 water solution 12-times; experiment 2-10 mL of 0.1 and 1 μM compound 12 water solution 1-, 3- and 5-times) by drenching to each plant pot. DMSO (0.01%) was used as a solvent control. The plants were grown till the end of the generative stage and then morphological parametres (primary inflorescence stem length, number of auxiliary branches, number of of lateral branches, fresh shoot biomass, number of flowers, number of siliques) and the seed yield were recorded.

Figure 8:
FIG. 8 illustrates the effect of compound 12 applied by drenching on shoot growth and biomass development of *Arabidopsis* plants.
Figure 9:
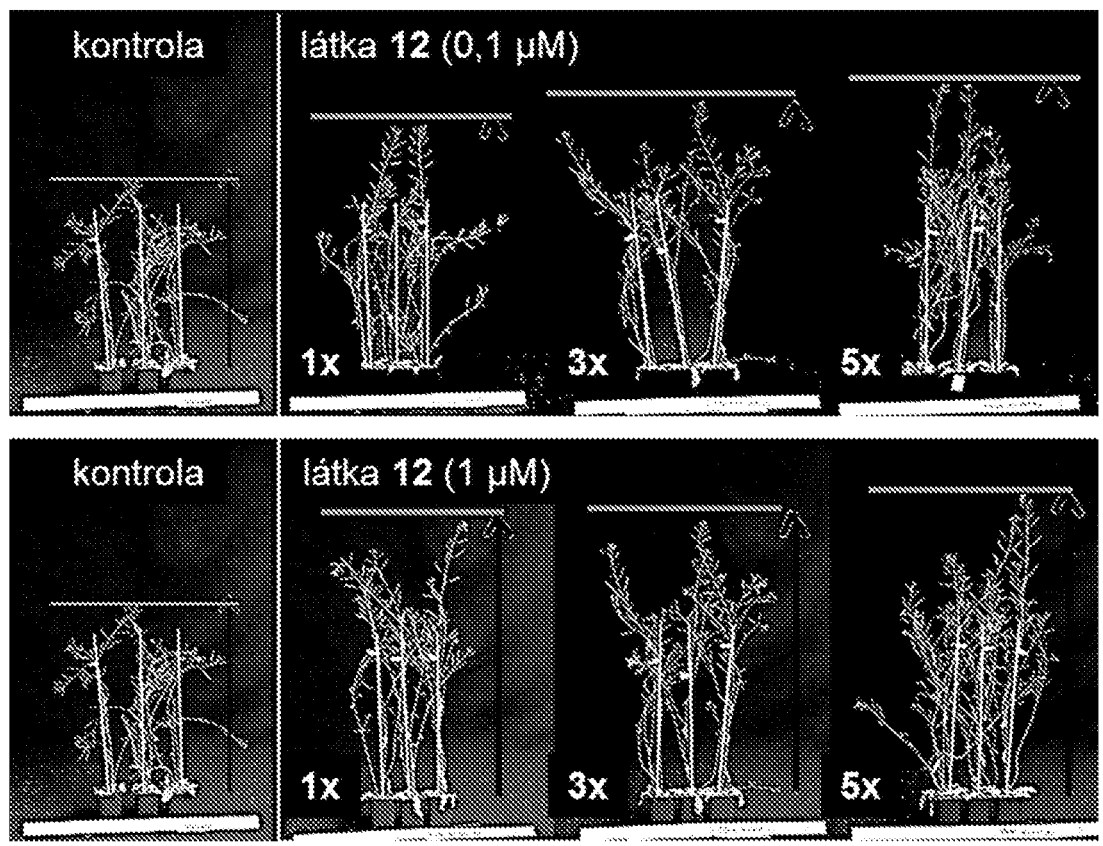
FIG. 9 shows the effect of compound 12 applied by drenching in different application rates on shoot growth and biomass development of *Arabidopsis* plants.

The initial experiment 1 showed that the regular drenching with 1 μM compound 12 leads to stimulation of the overall shoot biomass (FIG. 8). In the subsequent experiment 2 effect of drenching with two concentrations (0.1 and 1 μM) of compound 12 was tested in three application rates (1×, 3×, 5×). All the applications had stimulatory effect on the overall shoot biomass and significantly increased the monitored morphological parametres (FIG. 9). As summarized in Table 8 the higher doses increased the primary inflorescence stem length by 16-34%, number of auxiliary branches by 6-25%, number of of lateral branches by 77-249%, fresh shoot biomass by 6-22%, number of flowers by 20-89%, number of siliques by 5-66%, and the seed yield by 6-26%, compared to control, respectively (for particular values see Table 8).

The presented data indicate that drenching application with compound 12 increases significantly plant performance leading to increase in shoot architecture, biomass and total seed yield of *Arabidopsis* model plant.

Example 20

Effect of Seed Coating with Compound 12 on Shoot and Root Growth of Maize (Pot Experiment)

Figure 10:
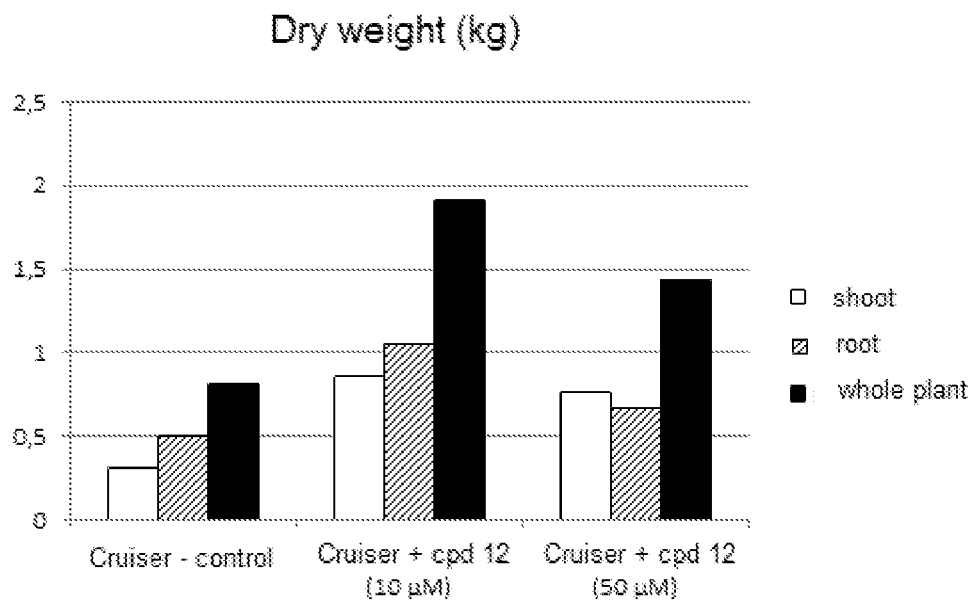
FIG. 10 shows effect of seed coating with compound 12 on formation of root and shoot dry biomass of maize in pot experiment. Values are shown relative to control.

The drenching experiments with model plant *Arabidopsis* pointed to potential application of compound 12 in stimulation of plant growth and development when the roots of the plants are exposed to the chemical. To prove this effect of compound 12 applied by seed coating was tested using maize. In the year 2011 pot experiment was performed with maize (hybrid Amadeo; KWS, FAO 230). The seeds were coated with 10 and 50 μM concentration of compound 12 mixed into seed treatment agent Cruiser OSR (Syngenta; 8 L of solution per 1000 kg of seeds). Seeds coated with only Cruiser OSR were used for control variant. The seeds were dried and then sown into the soil, one plant per 15 L pot (30 plants were used per variant). The plants were harvested after app. one month in stage DC 18 (eight leafs per plant). The shoots and the roots of each plant were separated and dried. The weight of dry shoot and root biomass was recorded. As shown in FIG. 10 compound 12 showed dose-dependent stimulatory effect on the both shoot and root dry biomass. The plants, which seeds were coated with the lower concentration of compound 12, formed 2-times higher root dry biomass and 2.75-times higher shoot dry biomass. In total this was reflected by 2.3-times increase of the total plant dry weight.

This data indicate that compound 12 can be used with advantage for seed applications to improve the biomass of crops such as maize.

Example 21

Effect of Seed Coating with Compound 12 on Shoot Biomass of Silage Maize (Field Experiment)

Based on the results discussed in previous Example 25, field plot experiments were performed on two different locations (Kroměříž Czech Republic; Olomouc, Czech Republic) in years 2012 and 2013 to evaluate the effect of seed coating with compound 12 on biomass formation of maize. In

TABLE 8

Phenotypic analysis of *Arabidopsis* plants treated with compound 12. The experiment was repeated three times with comparable results. In each experiment 30 plants per each variant were used. Stars indicate *P < 0.05, *P < 0.01, ***P < 0.001 (Student's t-test, n = 30).

| | | 0.1 μM | | |
|---|---|---|---|---|
| Trait | Control | application rate 1x | application rate 3x | application rate 5x |
| primary inflorescence stem length (cm) | 33.26 ± 3.4 | 32.78 ± 5.5 (98%) | 39.6 ± 3.8 (119%)*** | 38.61 ± 5.2 (116%)*** |
| No. of auxiliary branches | 3.59 ± 0.7 | 4.06 ± 1.3 (113%) | 3.82 ± 0.6 (106%) | 3.94 ± 1.1 (109%) |
| No. of lateral branches | 4.71 ± 1.8 | 8.59 ± 3.1 (182%)*** | 8.35 ± 3.3 (177%)*** | 9.82 ± 4.4 (208%)*** |
| No. of flowers | 75.71 ± 27.8 | 116.12 ± 70 (153%)* | 91.23 ± 50.1 (120%) | 99.59 ± 59.3 (131%) |
| No. of siliques | 133.59 ± 33.8 | 133.94 ± 47 (100%) | 154.29 ± 25.6 (115%) | 141.24 ± 31.7 (105%) |
| fresh shoot biomass (g) | 1.09 ± 0.3 | 1.18 ± 0.4 (108%) | 1.16 ± 0.2 (106%) | 1.18 ± 0.3 (108%) |
| seed yield (g) per plant | 0.29 ± 0.2 | 0.30 ± 0.1 (102%) | 0.31 ± 0.1 (106%) | 0.35 ± 0.1 (120%) |

| | 1 μM | | |
|---|---|---|---|
| Trait | application rate 1x | application rate 3x | application rate 5x |
| primary inflorescence stem length (cm) | 32.66 ± 3.8 (98%) | 39.07 ± 3.2 (117%)*** | 44.66 ± 5.9 (134%)*** |
| No. of auxiliary branches | 4.29 ± 1.5 (119%) | 4.29 ± 1.1 (119%)* | 4.50 ± 1.3 (125%) |
| No. of lateral branches | 13.35 ± 4.7 (283%)*** | 13.50 ± 3.9 (286%)*** | 16.44 ± 6.1 (349%)*** |
| No. of flowers | 139.65 ± 51.7 (184%)*** | 118.53 ± 36.6 (156%)*** | 143.56 ± 66.3 (189%)*** |
| No. of siliques | 134.82 ± 31.1 (100%) | 155.29 ± 44.1 (116%) | 220.00 ± 37.4 (164%)*** |
| fresh shoot biomass (g) | 1.17 ± 0.3 (107%) | 1.23 ± 0.3 (113%) | 1.81 ± 0.3 (166%)*** |
| seed yield (g) per plant | 0.37 ± 0.1 (126%) | 0.36 ± 0.1 (122%) | 0.33 ± 0.1 (111%) | the season 2012 the seeds of maize (hybrid Amadeo; KWS, FAO 230) were coated with 10 and 50 μM water solution of compound 12 (8 L of solution per 1000 kg of seeds). The seeds were dried and then sown in the sowing rate 90.000 seeds per hectare in 4 replications per each variant in randomized positions (each replication was 10 square meter plot). The plants were harvested when reached the stage of 33-34% of dry mass. The plants were then analyzed for their moisture and standardized dry mass.

The experiment was repeated in the season 2013 with 50 μM concentration of compound 12 in the same experimental design with maize hybrid Zidane (KWS, FAO 250).

The results obtained in all field plot experiments are summarized in Table 9. The data show that the seed treatment with compound 12 positively influenced the dry biomass of maize without any effect on the plant height. The average silage yield counted from all trials performed shows 110.9% increase in case of concentration 10 μM (counted from 2 trials) and 105.3% in case of concentration 50 μM (counted from 3 trials), respectively. This data indicate that compound 12 can be used with advantage for seed applications to improve the biomass of crops such as maize in field conditions.

TABLE 9

Summary of effects of on-seed application of compound 12 on maize silage yield obtained in field plot experiments performed at two localities in years 2012 and 2013 with maize hybrides Amadeo (KWS, FAO 230) and Zidane (KWS, FAO 250). Average silage yield of control was 50.95 t/ha (in Olomouc), and 49.60 t/ha (in Kromeriz), respectively. Asterics indicate P value 0.01-0.05.

| Variant | Absolute green matter/dry matter yield | Relative dry matter yield (% of control) | Height before harvest (cm/ % of control) | Location, year |
|---|---|---|---|---|
| Cpd 12 (50 μM) | 68.78/19.23 | 101.33 | 246.4/100.8 | Olomouc, 2013 |
| | 66.47/22.33 | 107.82* | — | Kroměříž, 2013 |
| Cpd 12 (10 μM) | 43.20/17.01 | 110.94 | 237.3/98.3 | Olomouc, 2012 |
| Cpd 12 (50 μM) | 44.31/17.80 | 116.06 | 235.8/97.7 | Olomouc, 2012 |
| Cpd 12 (10 μM) | 52.19/23.06 | 110.85 | 276.6/101.0 | Kroměříž, 2012 |
| Cpd 12 (50 μM) | 49.52/22.18 | 106.63 | 273.5/99.8 | Kroměříž, 2012 |

Example 22

Effect of Seed Coating with Compound 12 on Tillering of Winter Wheat (Field Experiment)

To evaluate the effect of of seed coating with compound 12 on morphological yield forming traits of winter wheat field plot experiment was performed in year 2012 on locality Olomouc, Czech Republic. Seeds of winter weat bakery variety Diadem (Selgen) were coated with 10 and 50 µM concentration of compound 12 mixed into seed treatment agent Cruiser 350FS (Syngenta; 10 L of solution per 1000 kg of seeds), seeds coated with only Cruiser 350FS were used for control variant. The seeds were dried and then sown in the sowing rate 3.500.000 seeds per hectare in 4 replications per each variant in randomized positions (each replication was 10 square meter plot). The plants were analyzed for number of productive tillers, medium tillers and weak tillers. The data summarized in Table 10 show that seed treatment with compound 12 led to significant dose-dependent increase in number of productive tillers and reduction of medium and weak tillers, respectively. The number of productive tillers was increased to 106-124% compared to untreated control.

This data indicate that compound 12 can used with advantage for seed applications to improve the tillering as an important yield forming trait of cereals such as winter wheat in field conditions.

TABLE 10

Summary of effect of seed application of compound 12 on tillering of winter wheat.
Asterics indicate significant differences, ** $P \geq 0.01$ and * $P = 0.01$-$0.05$.

| Variant | Number of productive tillers (% of control) | Number of medium tillers (% of control) | Number of weak tillers (% of control) | Location, harvest year |
|---|---|---|---|---|
| Control | 2.33 tillers | 1.60 tillers | 1.15 tillers | Olomouc, 2012 |
| Cpd 12 (10 µM) | 106.5 | 75.0* | 102.2 | Olomouc, 2012 |
| Cpd 12 (50 µM) | 124.2** | 78.1* | 80.4 | Olomouc, 2012 |

Example 23

Effect of Seed Coating with Compound 12 on Emergence and Freezing Tolerance of Winter Rapeseed (Field Experiment)

To evaluate the effect of of seed coating with compound 12 on yield forming traits of winter rapeseed field plot experiment was performed in season 2010/2011 on locality Opava, Czech Republic. Seeds of winter rapeseed variety Benefit (Selgen) were coated with 50 µM concentration of compound 12 mixed into the seed coating treatment Cruiser OSR (Syngenta; 15 L of solution per 1000 kg of seeds), seeds coated with only Cruiser OSR were used for control variant. The seeds were dried and then sown in the sowing rate 700.000 seeds per hectare in 4 replications per each variant in randomized positions (each replication was 10 square meter plot). In the experiment plant emergence, freezing tolerance and final seed yield were scored. The frost tolerance was estimated by method described in (Janáček, J., Prášil, I.: Quantification of plant frost injury by nonlinear fitting of an s-shaped function. Cryo-Letters vol. 12, 1991, no. 7, 47-52).

The results summarized in Table 13 show that seed application of compound 12 stimulated plant emergence (app. 20% more plants emerged in the same time compared to control). The treatment significantly decreased leaf biomass compared to control, whereas it had slightly stimulatory effect on the root length, leading to improved ratio between shoot and root towards the root system. The artificially estimated frost tolerance was significantly increased app. by 5%. The treatment in this trial increased the final seed yield by 3.1%.

This data indicate that compound 12 can be used with advantage for seed applications to improve the winter tolerance and subsequent final seed yield of winter rapeseed in field conditions.

TABLE 11

Summary of effect of seed application of compound 12 on yield influencing traits and final seed yield of winter rapeseed. Seed yield was counted as mean from 4 plots, other traits were counted from 15 randomly chosen plants.
Asterics indicate significant differences, ** $P \geq 0.01$ and* $P = 0.01$-$0.05$.

| Trait | control | Cpd 12 (50 µM) |
|---|---|---|
| Seed yield (t/ha) | 5.80 | 5.98 |
| Seed yield (% of control) | 100 | 103.1 |
| Leafs weight - autumn (22th October) | 17.24 | 11.69** |
| Root lenght (cm) - autumn (22th October) | 14.03 | 14.63 |
| Number of emerged plants per sq meter - autumn (11th October, 2010) | 49.5 | 60.0 |
| Plant height (cm) - autumn (11th October, 2010) | 6.0 | 6.6 |
| Estimated frost resistence (atrifical frost test) - Letal Temperature LT50 | −11.7 | −12.3* |

Example 24

In Vitro Cytotoxic Activity of Novel Compounds

Absence of toxic effects against mammalian (especially human) cell lines in a wide concentration range is one of the requirements on compounds intended for use in agriculture and medicine. Because toxic compounds negatively influence metabolic processes in cells, many standard cytotoxicity assays are based on measurement of metabolisation rate of various artificial substrates. Resulting product is then quantified e.g. by means of spectrometry. The assays can be easily modified for use in 96-well plates. For evaluation of cytotoxic effect of compounds of this invention, a microtiter assay based on quantification of metabolisation of Calcein AM was used. The assay is widely used in drug screening programs and in chemosensitivity testing. In live cells, Calcein AM is enzymatically hydrolysed and accumulation of resulting calcein is manifested by green fluorescence.

The cytotoxicity of the studied compounds was determined with human fibroblast lines MRC-5 (lung fibroblasts) and BJ (foreskin fibroblasts). The cells, cultured in DMEM (supplemented with 10% fetal calf serum, 4 mM glutamine, 100 IU/mL penicillin, 100 µg/mL streptomycin) in a humidified $CO_2$ incubator at 37° C., were redistributed into 96-well microtiter plates at appropriate densities for their respective cell sizes and growth rates. After preincubation, test compounds in 3-fold dilutions were added in triplicates. Treatment lasted for 72 h and then calcein AM solution was added. The fluorescence of the live cells was measured at 485 nm/538 nm (excitation/emission) with a Fluoroskan Ascent microplate reader (Labsystems). IC50 values, the drug concentrations reducing number of viable cells to 50%, were determined from the dose-response curves.

Figure 11:
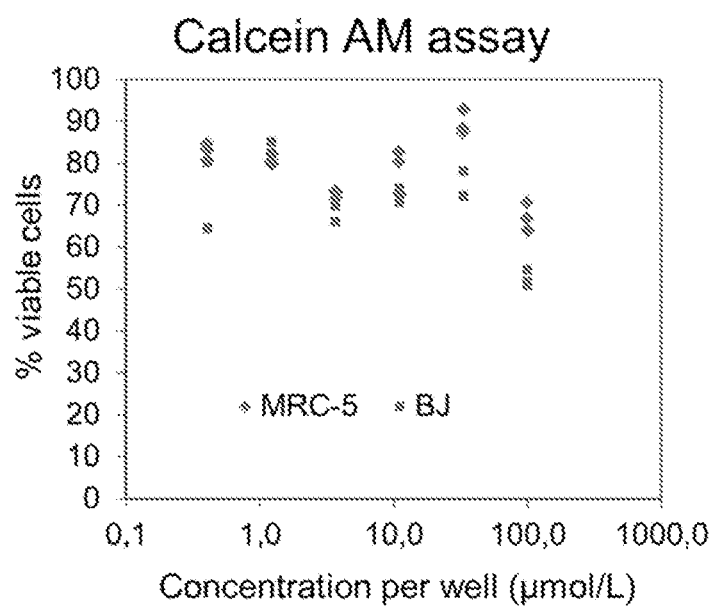
FIG. 11 illustrates the effect of compound 12 on viability of human MRC-5 and BJ cell lines in Calcein AM assay after 3 days. Values are shown relative to control.

The data obtained from a calcein AM viability/cytotoxicity assay are presented in FIG. 11. The obtained IC50 values show that compound 12 did not reach IC50 value even in the concentration 100 µM with both tested primary cell lines.

Example 25

Genotoxicity of Compound 12 in Ames Test

Compound 12 was tested in classical Ames test to assess the mutagenic potential of the compound. A positive test indicates that the chemical might act as a carcinogen (although a number of false-positives and false-negatives are known; Charnley G (2002).

The compound 12 was tested using Ames MPF™ 98/100 Mutagenicity Assay kit (Aniara, Ohio) that is employing Salmonella typhimurium strains TA100 (for the detection of base substitution mutations) and TA98 (for the detection of frameshift mutations) according to the instructions for use.

Figure 12:
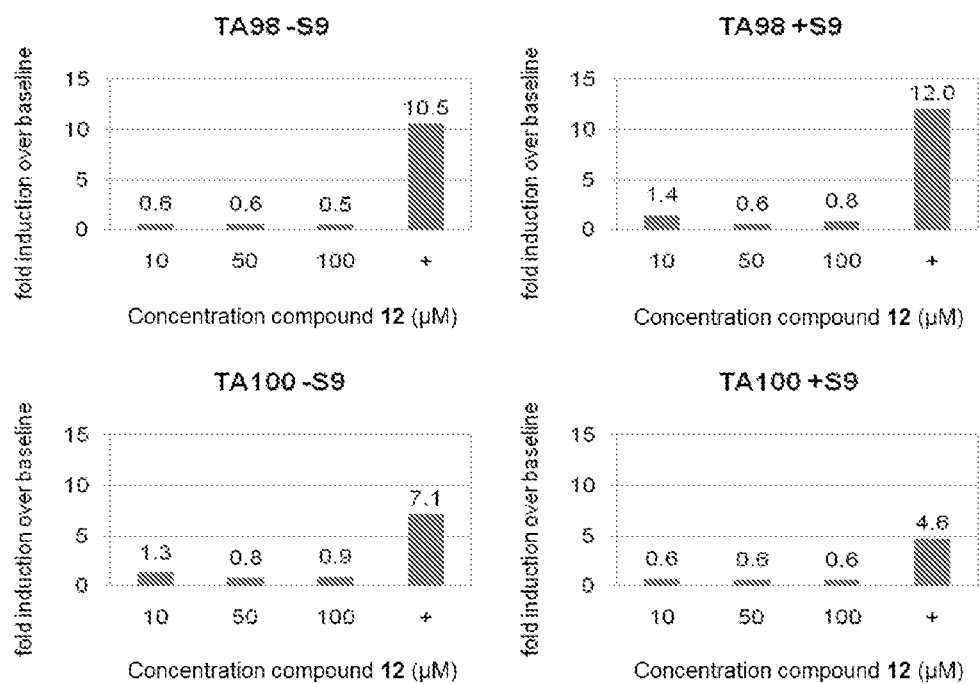
FIG. 12 shows activity of compound 12 in Ames test (Ames MPF™ 98/100 Microplate Format Mutagenicity Assay); +/−S9 means with or without metabolic activation, final concentration of positive controls (labeled as +): for −S9: 2 µg/ml 2-nitrofluorene+0.1 µg/ml 4-nitroquinoline-N-oxide, for +S9: 5 µg/ml 2-aminoanthacene.

The results summarized in FIG. 12 show that the compound 12 did not score positively in the assay up to the highest concentration tested (100 µM).

Example 26

Effect of Compound 12 on Induction of DNA Breakage

Maintenance of genome integrity is essential for homeostasis and survival as impaired DNA damage response may predispose to grave pathologies such as neurodegenerative and immunodeficiency syndromes, cancer and premature aging (Mistrik et al., 2009). The potential effect of compound 12 on stimulation of DNA breakage was thus further estimated through analysis of phosphorylated histone H2AX (gamma-H2AX) quantified by optimized automated single-cell image analysis (Mistrik et al., 2009). The compound 12 was tested in concentration of 100 µM, the highest concentration accessible due to the compound solubility. Induction of DNA breakage was tested using human U2OS cells. The U2OS cells were cultivated at standard cultivation condition (37° C., 5% CO2). As a positive control, cells were irradiated by roentgen radiation (Baltobloc) (0.5 Gy-2 Gy), one hour later fixed and stained for γ-H2AX, a well established marker of the DNA damage. Parallel samples were treated by compound 12 for 24 hours, fixed and also stained for γ-H2AX. Microscopy analysis followed by computer based signal quantification was performed as described previously (Mistrik et al., 2009).

Figure 13:
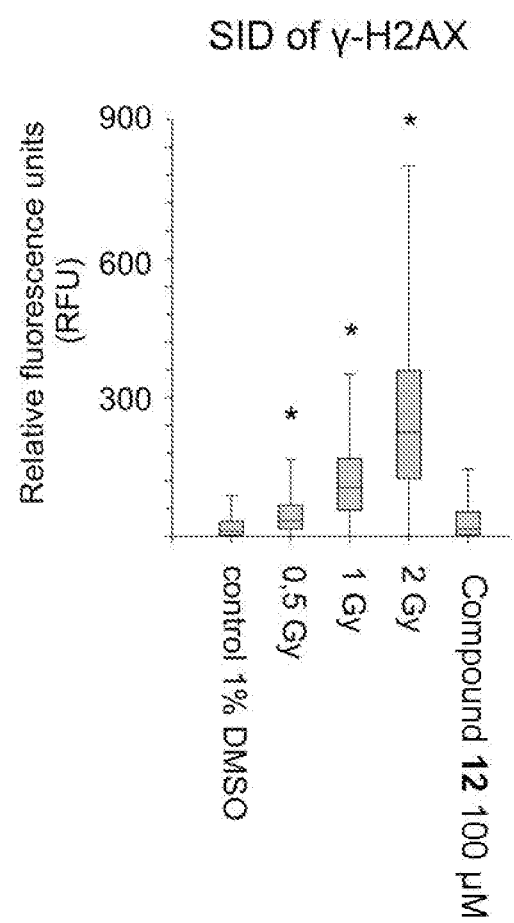
FIG. 13 shows immunofluorescent detection of γ-H2AX (indicator of DNA damage) after the application of compound 12 for 24 h, cell line U-2-OS, positive control: 0.5-2 Gy roentgen radiation (Baltobloc), * significantly different from control, t-test, α=0.01.

As shown in FIG. 13 compound 12 showed no effect on DNA damage confirming the zero mutagenic effects observed in the Ames test.

Example 27

Preparations

The growth regulatory preparations usually contain from 0.1 to 99% (w/w), preferably 0.1 to 95% (w/w), of active ingredient mixture comprising a compound of formula I, from 1 to 99.9% (w/w) of a solid or liquid adjuvant, and from 0.1 to 25% (w/w) of a surfactant. Whereas commercial products are usually formulated as concentrates, the end user will normally employ dilute formulations. The preparations may also comprise further ingredients, such as stabilisers, e.g. vegetable oils or epoxidised vegetable oils (epoxidised coconut oil 0;1, rapeseed oil or soybean oil), antifoams, e.g. silicone oil, preservatives, viscosity regulators, binders, tackifiers, and also fertilisers or other active ingredients. Preferred preparations have especially the following compositions: (%=percent by weight)

| A1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| cyclohexanone | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| A2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for use in the form of microdrops.

| A3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| A4. Coated granules | a) | b) | c) |
|---|---|---|---|
| active ingredient mixture | 0.1% | 5% | 15% |
| highly dispersed silicic acid | 0.9% | 2% | 2% |
| inorganic carrier | 99.0% | 93% | 83% |
| (0.1-1 mm) | | | |
| e.g. CaCO$_3$ or SiO$_2$ | | | |

The active ingredient is dissolved in methylene chloride and applied to the carrier by spraying, and the solvent is then evaporated off in vacuo.

| A5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier | 98.0% | 92% | 80% |
| (AE 0.1-1 mm) | | | |
| e.g. CaCO$_3$ or SiO$_2$ | | | |

The finely ground active ingredient is uniformly applied to the carrier moistened with polyethylene glycol. Non-dusty coated granules are obtained in this manner

| A6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| A7. Dusts | a) | b) | c) |
|---|---|---|---|
| active ingredient mixture | 0.1% | 1% | 5% |
| talc | 39.9% | 49% | 35% |
| kaolin | 60.0% | 50% | 60% |

Ready-to-use dusts are obtained by mixing the active ingredient with the carriers and grinding the mixture in a suitable mill.

| A8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

Example 28

Gel Formulation

The names of the formulation components are given according to the terminology of the registering authorities and their quantity is in grams per 100 g.

| Gel | /100 g |
|---|---|
| Active compound 2-chloro-6-(4-hydroxyanilino)-9-(tetrahydropyran-2-yl or tetrahydrofuran-2-yl)purine | 1.0 g |
| butylhydroxytoluenum (Nipanox BHT) | 0.2 g |
| butylparaben (Nipabutyl) | 0.2 g |
| diethylene glycol monoethyl ether (Transcutol P) | 10.0 g |
| silica colloidalis anhydrica (Zeopharm 177) | 5.0 g |
| propylene glycol laurate (Lauroglycol FCC) | 83.6 g |

The gel consistence may be additionally modified by addition of silica colloidalis anhydrica. It is again expected that the transdermal Transcutol P/Lauroglycol FCC system will increase the efficiency of active compound. Silica colloidalis anhydrica will probably slow down the penetration of the active substance.

The invention claimed is:

1. Substituted-6-anilino-9-heterocyclylpurines of general formula I

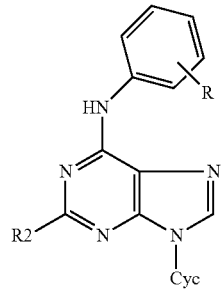

(I)

and pharmaceutically acceptable salts thereof with alkali metals, ammonium or amines; racemates or optically active isomers thereof, as well as their addition salts with acids, wherein R denotes one to five substituents independently selected from the group consisting of halogen, hydroxy, amino, and alkyloxy group, R2 is selected from the group consisting of amino, halogen, hydroxy, thio, and alkylthio group, Cyc is selected from unsubstituted tetrahydropyranyl and tetrahydrofuranyl.

2. Substituted-6-anilino-9-heterocyclylpurines of general formula I according to claim 1, wherein Cyc is selected from tetrahydropyran-2-yl and tetrahydrofuran-2-yl.

3. A method of stimulation of growth and development of plant shoots without inhibiting development of plant roots, comprising the step of applying at least one substituted 6-anilino-9-heterocyclylpurine according to claim 1 to said plant shoots.

4. A method of increasing the yield and quality of agricultural products in harmful conditions selected from the group consisting of drought, heat, salinity, light, freezing and flowage, comprising the step of applying at least one substituted 6-anilino-9-heterocyclylpurine according to claim 1 to plants.

5. A method of inhibiting stress-induced senescence in the production of crops, wherein the stress is selected from the group consisting of drought, heat, salinity, light, freezing and flowage stress, comprising the step of applying at least one substituted 6-anilino-9-heterocyclylpurine according to claim 1 to said crops.

6. Preparations for inhibition of plant stress, wherein the stress is selected from the group consisting of drought, heat, salinity, light, freezing and flowage stress, characterized in that they contain at least one substituted 6-anilino-9-heterocyclylpurine of general formula I according to claim 1 or a salt thereof with metals, ammonium or amines, or an addition salt thereof with acids, and at least one auxiliary substance.

7. A method of inhibiting plant stress, wherein the stress is selected from the group consisting of drought, heat, salinity, light, freezing and flowage stress, characterized in that at least one substituted 6-anilino-9-heterocyclylpurine of general formula I according to claim 1 or a salt thereof with metals, ammonium or amines, or an addition salt thereof with acids, is applied on a whole plant, plant organ, plant tissue, and/or plant cell.

8. The method according to claim 5, wherein the crops are selected from the group consisting of: cereals, beet, pomes, drupes, soft fruits, leguminous plants, oil plants, cucumber plants, citrus fruit, vegetables, tobacco, nuts, eggplants, sugar cane, tea, vine grapes, hops, bananas, natural rubber, medicinal plants, and ornamentals.

9. The substituted-6-anilino-9-heterocyclylpurines of general formula I according to claim 1, selected from the group consisting of:
- 2-chloro-6-(2-chloroanilino)-9-(tetrahydropyran-2-yl)purine,
- 2-fluoro-6-(2-chloroanilino)-9-(tetrahydropyran-2-yl)purine,
- 2-bromo-6-(2-chloroanilino)-9-(tetrahydropyran-2-yl)purine,
- 2-iodo-6-(2-chloroanilino)-9-(tetrahydropyran-2-yl)purine,
- 2-amino-6-(2-chloroanilino)-9-(tetrahydropyran-2-yl)purine,
- 2-hydroxy-6-(2-chloroanilino)-9-(tetrahydropyran-2-yl)purine,
- 2-thio-6-(2-chloroanilino)-9-(tetrahydropyran-2-yl)purine,
- 2-methylthio-6-(2-chloroanilino)-9-(tetrahydropyran-2-yl)purine,
- 2-chloro-6-(2-chloroanilino)-9-(tetrahydrofuran-2-yl)purine,
- 2-fluoro-6-(2-chloroanilino)-9-(tetrahydrofuran-2-yl)purine,
- 2-bromo-6-(2-chloroanilino)-9-(tetrahydrofuran-2-yl)purine,
- 2-iodo-6-(2-chloroanilino)-9-(tetrahydrofuran-2-yl)purine,
- 2-amino-6-(2-chloroanilino)-9-(tetrahydrofuran-2-yl)purine,
- 2-hydroxy-6-(2-chloroanilino)-9-(tetrahydrofuran-2-yl)purine,
- 2-thio-6-(2-chloroanilino)-9-(tetrahydrofuran-2-yl)purine,
- 2-methylthio-6-(2-chloroanilino)-9-(tetrahydrofuran-2-yl)purine,
- 2-chloro-6-(3-chloroanilino)-9-(tetrahydropyran-2-yl)purine,
- 2-fluoro-6-(3-chloroanilino)-9-(tetrahydropyran-2-yl)purine,
- 2-bromo-6-(3-chloroanilino)-9-(tetrahydropyran-2-yl)purine,
- 2-iodo-6-(3-chloroanilino)-9-(tetrahydropyran-2-yl)purine,
- 2-amino-6-(3-chloroanilino)-9-(tetrahydropyran-2-yl)purine,
- 2-thio-6-(3-chloroanilino)-9-(tetrahydropyran-2-yl)purine,
- 2-methylthio-6-(3-chloroanilino)-9-(tetrahydropyran-2-yl)purine,
- 2-chloro-6-(3-chloroanilino)-9-(tetrahydrofuran-2-yl)purine,
- 2-fluoro-6-(3-chloroanilino)-9-(tetrahydrofuran-2-yl)purine,
- 2-bromo-6-(3-chloroanilino)-9-(tetrahydrofuran-2-yl)purine,
- 2-iodo-6-(3-chloroanilino)-9-(tetrahydrofuran-2-yl)purine,
- 2-amino-6-(3-chloroanilino)-9-(tetrahydrofuran-2-yl)purine,
- 2-thio-6-(3-chloroanilino)-9-(tetrahydrofuran-2-yl)purine,
- 2-methylthio-6-(3-chloroanilino)-9-(tetrahydrofuran-2-yl)purine,
- 2-chloro-6-(4-chloroanilino)-9-(tetrahydropyran-2-yl)purine,
- 2-fluoro-6-(4-chloroanilino)-9-(tetrahydropyran-2-yl)purine,
- 2-bromo-6-(4-chloroanilino)-9-(tetrahydropyran-2-yl)purine,
- 2-iodo-6-(4-chloroanilino)-9-(tetrahydropyran-2-yl)purine,
- 2-amino-6-(4-chloroanilino)-9-(tetrahydropyran-2-yl)purine,
- 2-hydroxy-6-(4-chloroanilino)-9-(tetrahydropyran-2-yl)purine,
- 2-thio-6-(4-chloroanilino)-9-(tetrahydropyran-2-yl)purine,
- 2-methylthio-6-(4-chloroanilino)-9-(tetrahydropyran-2-yl)purine,
- 2-chloro-6-(4-chloroanilino)-9-(tetrahydrofuran-2-yl)purine,
- 2-fluoro-6-(4-chloroanilino)-9-(tetrahydrofuran-2-yl)purine,
- 2-bromo-6-(4-chloroanilino)-9-(tetrahydrofuran-2-yl)purine,
- 2-iodo-6-(4-chloroanilino)-9-(tetrahydrofuran-2-yl)purine,
- 2-amino-6-(4-chloroanilino)-9-(tetrahydrofuran-2-yl)purine,
- 2-hydroxy-6-(4-chloroanilino)-9-(tetrahydrofuran-2-yl)purine,
- 2-thio-6-(4-chloroanilino)-9-(tetrahydrofuran-2-yl)purine,
- 2-methylthio-6-(4-chloroanilino)-9-(tetrahydrofuran-2-yl)purine,
- 2-chloro-6-(2-fluoroanilino)-9-(tetrahydropyran-2-yl)purine,
- 2-fluoro-6-(2-fluoroanilino)-9-(tetrahydropyran-2-yl)purine,
- 2-bromo-6-(2-fluoroanilino)-9-(tetrahydropyran-2-yl)purine,
- 2-iodo-6-(2-fluoroanilino)-9-(tetrahydropyran-2-yl)purine,
- 2-amino-6-(2-fluoroanilino)-9-(tetrahydropyran-2-yl)purine,
- 2-hydroxy-6-(2-fluoroanilino)-9-(tetrahydropyran-2-yl)purine, 2-thio-6-(2-fluoroanilino)-9-(tetrahydropyran-2-yl)purine,
2-methylthio-6-(2-fluoroanilino)-9-(tetrahydropyran-2-yl)purine,
2-chloro-6-(2-fluoroanilino)-9-(tetrahydrofuran-2-yl)purine,
2-fluoro-6-(2-fluoroanilino)-9-(tetrahydrofuran-2-yl)purine,
2-bromo-6-(2-fluoroanilino)-9-(tetrahydrofuran-2-yl)purine,
2-iodo-6-(2-fluoroanilino)-9-(tetrahydrofuran-2-yl)purine,
2-amino-6-(2-fluoroanilino)-9-(tetrahydrofuran-2-yl)purine,
2-hydroxy-6-(2-fluoroanilino)-9-(tetrahydrofuran-2-yl)purine,
2-thio-6-(2-fluoroanilino)-9-(tetrahydrofuran-2-yl)purine,
2-methylthio-6-(2-fluoroanilino)-9-(tetrahydrofuran-2-yl)purine,
2-chloro-6-(3-fluoroanilino)-9-(tetrahydropyran-2-yl)purine,
2-fluoro-6-(3-fluoroanilino)-9-(tetrahydropyran-2-yl)purine,
2-bromo-6-(3-fluoroanilino)-9-(tetrahydropyran-2-yl)purine,
2-iodo-6-(3-fluoroanilino)-9-(tetrahydropyran-2-yl)purine,
2-amino-6-(3-fluoroanilino)-9-(tetrahydropyran-2-yl)purine,
2-hydroxy-6-(3-fluoroanilino)-9-(tetrahydropyran-2-yl)purine,
2-thio-6-(3-fluoroanilino)-9-(tetrahydropyran-2-yl)purine,
2-methylthio-6-(3-fluoroanilino)-9-(tetrahydropyran-2-yl)purine,
2-chloro-6-(3-fluoroanilino)-9-(tetrahydrofuran-2-yl)purine,
2-fluoro-6-(3-fluoroanilino)-9-(tetrahydrofuran-2-yl)purine,
2-bromo-6-(3-fluoroanilino)-9-(tetrahydrofuran-2-yl)purine,
2-iodo-6-(3-fluoroanilino)-9-(tetrahydrofuran-2-yl)purine,
2-amino-6-(3-fluoroanilino)-9-(tetrahydrofuran-2-yl)purine,
2-hydroxy-6-(3-fluoroanilino)-9-(tetrahydrofuran-2-yl)purine,
2-thio-6-(3-fluoroanilino)-9-(tetrahydrofuran-2-yl)purine,
2-methylthio-6-(3-fluoroanilino)-9-(tetrahydrofuran-2-yl)purine,
2-chloro-6-(4-fluoroanilino)-9-(tetrahydropyran-2-yl)purine,
2-fluoro-6-(4-fluoroanilino)-9-(tetrahydropyran-2-yl)purine,
2-bromo-6-(4-fluoroanilino)-9-(tetrahydropyran-2-yl)purine,
2-iodo-6-(4-fluoroanilino)-9-(tetrahydropyran-2-yl)purine,
2-amino-6-(4-fluoroanilino)-9-(tetrahydropyran-2-yl)purine,
2-hydroxy-6-(4-fluoroanilino)-9-(tetrahydropyran-2-yl)purine,
2-thio-6-(4-fluoroanilino)-9-(tetrahydropyran-2-yl)purine,
2-methylthio-6-(4-fluoroanilino)-9-(tetrahydropyran-2-yl)purine,
2-chloro-6-(4-fluoroanilino)-9-(tetrahydrofuran-2-yl)purine,
2-fluoro-6-(4-fluoroanilino)-9-(tetrahydrofuran-2-yl)purine,
2-bromo-6-(4-fluoroanilino)-9-(tetrahydrofuran-2-yl)purine,
2-iodo-6-(4-fluoroanilino)-9-(tetrahydrofuran-2-yl)purine,
2-amino-6-(4-fluoroanilino)-9-(tetrahydrofuran-2-yl)purine,
2-hydroxy-6-(4-fluoroanilino)-9-(tetrahydrofuran-2-yl)purine,
2-thio-6-(4-fluoroanilino)-9-(tetrahydrofuran-2-yl)purine,
2-methylthio-6-(4-fluoroanilino)-9-(tetrahydrofuran-2-yl)purine,
2-chloro-6-(2-bromoanilino)-9-(tetrahydropyran-2-yl)purine,
2-fluoro-6-(2-bromoanilino)-9-(tetrahydropyran-2-yl)purine,
2-bromo-6-(2-bromoanilino)-9-(tetrahydropyran-2-yl)purine,
2-iodo-6-(2-bromoanilino)-9-(tetrahydropyran-2-yl)purine,
2-amino-6-(2-bromoanilino)-9-(tetrahydropyran-2-yl)purine,
2-hydroxy-6-(2-bromoanilino)-9-(tetrahydropyran-2-yl)purine,
2-thio-6-(2-bromoanilino)-9-(tetrahydropyran-2-yl)purine,
2-methylthio-6-(2-bromoanilino)-9-(tetrahydropyran-2-yl)purine,
2-chloro-6-(2-bromoanilino)-9-(tetrahydrofuran-2-yl)purine,
2-fluoro-6-(2-bromoanilino)-9-(tetrahydrofuran-2-yl)purine,
2-bromo-6-(2-bromoanilino)-9-(tetrahydrofuran-2-yl)purine,
2-iodo-6-(2-bromoanilino)-9-(tetrahydrofuran-2-yl)purine,
2-amino-6-(2-bromoanilino)-9-(tetrahydrofuran-2-yl)purine,
2-hydroxy-6-(2-bromoanilino)-9-(tetrahydrofuran-2-yl)purine,
2-thio-6-(2-bromoanilino)-9-(tetrahydrofuran-2-yl)purine,
2-methylthio-6-(2-bromoanilino)-9-(tetrahydrofuran-2-yl)purine,
2-chloro-6-(3-bromoanilino)-9-(tetrahydropyran-2-yl)purine,
2-fluoro-6-(3-bromoanilino)-9-(tetrahydropyran-2-yl)purine,
2-bromo-6-(3-bromoanilino)-9-(tetrahydropyran-2-yl)purine,
2-iodo-6-(3-bromoanilino)-9-(tetrahydropyran-2-yl)purine,
2-amino-6-(3-bromoanilino)-9-(tetrahydropyran-2-yl)purine,
2-thio-6-(3-bromoanilino)-9-(tetrahydropyran-2-yl)purine,
2-methylthio-6-(3-bromoanilino)-9-(tetrahydropyran-2-yl)purine,
2-chloro-6-(3-bromoanilino)-9-(tetrahydrofuran-2-yl)purine, 2-fluoro-6-(3-bromoanilino)-9-(tetrahydrofuran-2-yl)purine,
2-bromo-6-(3-bromoanilino)-9-(tetrahydrofuran-2-yl)purine,
2-iodo-6-(3-bromoanilino)-9-(tetrahydrofuran-2-yl)purine,
2-amino-6-(3-bromoanilino)-9-(tetrahydrofuran-2-yl)purine,
2-thio-6-(3-bromoanilino)-9-(tetrahydrofuran-2-yl)purine,
2-methylthio-6-(3-bromoanilino)-9-(tetrahydrofuran-2-yl)purine,
2-chloro-6-(4-bromoanilino)-9-(tetrahydropyran-2-yl)purine,
2-fluoro-6-(4-bromoanilino)-9-(tetrahydropyran-2-yl)purine,
2-bromo-6-(4-bromoanilino)-9-(tetrahydropyran-2-yl)purine,
2-iodo-6-(4-bromoanilino)-9-(tetrahydropyran-2-yl)purine,
2-amino-6-(4-bromoanilino)-9-(tetrahydropyran-2-yl)purine,
2-thio-6-(4-bromoanilino)-9-(tetrahydropyran-2-yl)purine,
2-methylthio-6-(4-bromoanilino)-9-(tetrahydropyran-2-yl)purine,
2-chloro-6-(4-bromoanilino)-9-(tetrahydrofuran-2-yl)purine,
2-fluoro-6-(4-bromoanilino)-9-(tetrahydrofuran-2-yl)purine,
2-bromo-6-(4-bromoanilino)-9-(tetrahydrofuran-2-yl)purine,
2-iodo-6-(4-bromoanilino)-9-(tetrahydrofuran-2-yl)purine,
2-amino-6-(4-bromoanilino)-9-(tetrahydrofuran-2-yl)purine,
2-thio-6-(4-bromoanilino)-9-(tetrahydrofuran-2-yl)purine,
2-methylthio-6-(4-bromoanilino)-9-(tetrahydrofuran-2-yl)purine,
2-chloro-6-(2-methoxyanilino)-9-(tetrahydropyran-2-yl)purine,
2-fluoro-6-(2-methoxyanilino)-9-(tetrahydropyran-2-yl)purine,
2-bromo-6-(2-methoxyanilino)-9-(tetrahydropyran-2-yl)purine,
2-iodo-6-(2-methoxyanilino)-9-(tetrahydropyran-2-yl)purine,
2-amino-6-(2-methoxyanilino)-9-(tetrahydropyran-2-yl)purine,
2-thio-6-(2-methoxyanilino)-9-(tetrahydropyran-2-yl)purine,
2-methylthio-6-(2-methoxyanilino)-9-(tetrahydropyran-2-yl)purine,
2-chloro-6-(2-methoxyanilino)-9-(tetrahydrofuran-2-yl)purine,
2-fluoro-6-(2-methoxyanilino)-9-(tetrahydrofuran-2-yl)purine,
2-bromo-6-(2-methoxyanilino)-9-(tetrahydrofuran-2-yl)purine,
2-iodo-6-(2-methoxyanilino)-9-(tetrahydrofuran-2-yl)purine,
2-amino-6-(2-methoxyanilino)-9-(tetrahydrofuran-2-yl)purine,
2-thio-6-(2-methoxyanilino)-9-(tetrahydrofuran-2-yl)purine,
2-methylthio-6-(2-methoxyanilino)-9-(tetrahydrofuran-2-yl)purine,
2-chloro-6-(3-methoxyanilino)-9-(tetrahydropyran-2-yl)purine,
2-fluoro-6-(3-methoxyanilino)-9-(tetrahydropyran-2-yl)purine,
2-bromo-6-(3-methoxyanilino)-9-(tetrahydropyran-2-yl)purine,
2-iodo-6-(3-methoxyanilino)-9-(tetrahydropyran-2-yl)purine,
2-amino-6-(3-methoxyanilino)-9-(tetrahydropyran-2-yl)purine,
2-thio-6-(3-methoxyanilino)-9-(tetrahydropyran-2-yl)purine,
2-methylthio-6-(3-methoxyanilino)-9-(tetrahydropyran-2-yl)purine,
2-chloro-6-(3-methoxyanilino)-9-(tetrahydrofuran-2-yl)purine,
2-fluoro-6-(3-methoxyanilino)-9-(tetrahydrofuran-2-yl)purine,
2-bromo-6-(3-methoxyanilino)-9-(tetrahydrofuran-2-yl)purine,
2-iodo-6-(3-methoxyanilino)-9-(tetrahydrofuran-2-yl)purine,
2-amino-6-(3-methoxyanilino)-9-(tetrahydrofuran-2-yl)purine,
2-thio-6-(3-methoxyanilino)-9-(tetrahydrofuran-2-yl)purine,
2-methylthio-6-(3-methoxyanilino)-9-(tetrahydrofuran-2-yl)purine,
2-chloro-6-(4-methoxyanilino)-9-(tetrahydropyran-2-yl)purine,
2-fluoro-6-(4-methoxyanilino)-9-(tetrahydropyran-2-yl)purine,
2-bromo-6-(4-methoxyanilino)-9-(tetrahydropyran-2-yl)purine,
2-iodo-6-(4-methoxyanilino)-9-(tetrahydropyran-2-yl)purine,
2-amino-6-(4-methoxyanilino)-9-(tetrahydropyran-2-yl)purine,
2-hydroxy-6-(4-methoxyanilino)-9-(tetrahydropyran-2-yl)purine,
2-thio-6-(4-methoxyanilino)-9-(tetrahydropyran-2-yl)purine,
2-methylthio-6-(4-methoxyanilino)-9-(tetrahydropyran-2-yl)purine,
2-chloro-6-(4-methoxyanilino)-9-(tetrahydrofuran-2-yl)purine,
2-fluoro-6-(4-methoxyanilino)-9-(tetrahydrofuran-2-yl)purine,
2-bromo-6-(4-methoxyanilino)-9-(tetrahydrofuran-2-yl)purine,
2-iodo-6-(4-methoxyanilino)-9-(tetrahydrofuran-2-yl)purine,
2-amino-6-(4-methoxyanilino)-9-(tetrahydrofuran-2-yl)purine,
2-hydroxy-6-(4-methoxyanilino)-9-(tetrahydrofuran-2-yl)purine,
2-thio-6-(4-methoxyanilino)-9-(tetrahydrofuran-2-yl)purine,
2-methylthio-6-(4-methoxyanilino)-9-(tetrahydrofuran-2-yl)purine,
2-chloro-6-(2-ethoxyanilino)-9-(tetrahydropyran-2-yl)purine,
2-fluoro-6-(2-ethoxyanilino)-9-(tetrahydropyran-2-yl)purine, 2-bromo-6-(2-ethoxyanilino)-9-(tetrahydropyran-2-yl)purine,
2-iodo-6-(2-ethoxyanilino)-9-(tetrahydropyran-2-yl)purine,
2-amino-6-(2-ethoxyanilino)-9-(tetrahydropyran-2-yl)purine,
2-hydroxy-6-(2-ethoxyanilino)-9-(tetrahydropyran-2-yl)purine,
2-thio-6-(2-ethoxyanilino)-9-(tetrahydropyran-2-yl)purine,
2-methylthio-6-(2-ethoxyanilino)-9-(tetrahydropyran-2-yl)purine,
2-chloro-6-(2-ethoxyanilino)-9-(tetrahydrofuran-2-yl)purine,
2-fluoro-6-(2-ethoxyanilino)-9-(tetrahydrofuran-2-yl)purine,
2-bromo-6-(2-ethoxyanilino)-9-(tetrahydrofuran-2-yl)purine,
2-iodo-6-(2-ethoxyanilino)-9-(tetrahydrofuran-2-yl)purine,
2-amino-6-(2-ethoxyanilino)-9-(tetrahydrofuran-2-yl)purine,
2-hydroxy-6-(2-ethoxyanilino)-9-(tetrahydrofuran-2-yl)purine,
2-thio-6-(2-ethoxyanilino)-9-(tetrahydrofuran-2-yl)purine,
2-methylthio-6-(2-ethoxyanilino)-9-(tetrahydrofuran-2-yl)purine,
2-chloro-6-(3-ethoxyanilino)-9-(tetrahydropyran-2-yl)purine,
2-fluoro-6-(3-ethoxyanilino)-9-(tetrahydropyran-2-yl)purine,
2-bromo-6-(3-ethoxyanilino)-9-(tetrahydropyran-2-yl)purine,
2-iodo-6-(3-ethoxyanilino)-9-(tetrahydropyran-2-yl)purine,
2-amino-6-(3-ethoxyanilino)-9-(tetrahydropyran-2-yl)purine,
2-hydroxy-6-(3-ethoxyanilino)-9-(tetrahydropyran-2-yl)purine,
2-thio-6-(3-ethoxyanilino)-9-(tetrahydropyran-2-yl)purine,
2-methylthio-6-(3-ethoxyanilino)-9-(tetrahydropyran-2-yl)purine,
2-chloro-6-(3-ethoxyanilino)-9-(tetrahydrofuran-2-yl)purine,
2-fluoro-6-(3-ethoxyanilino)-9-(tetrahydrofuran-2-yl)purine,
2-bromo-6-(3-ethoxyanilino)-9-(tetrahydrofuran-2-yl)purine,
2-iodo-6-(3-ethoxyanilino)-9-(tetrahydrofuran-2-yl)purine,
2-amino-6-(3-ethoxyanilino)-9-(tetrahydrofuran-2-yl)purine,
2-hydroxy-6-(3-ethoxyanilino)-9-(tetrahydrofuran-2-yl)purine,
2-thio-6-(3-ethoxyanilino)-9-(tetrahydrofuran-2-yl)purine,
2-methylthio-6-(3-ethoxyanilino)-9-(tetrahydrofuran-2-yl)purine,
2-chloro-6-(4-ethoxyanilino)-9-(tetrahydropyran-2-yl)purine,
2-fluoro-6-(4-ethoxyanilino)-9-(tetrahydropyran-2-yl)purine,
2-bromo-6-(4-ethoxyanilino)-9-(tetrahydropyran-2-yl)purine,
2-iodo-6-(4-ethoxyanilino)-9-(tetrahydropyran-2-yl)purine,
2-amino-6-(4-ethoxyanilino)-9-(tetrahydropyran-2-yl)purine,
2-hydroxy-6-(4-ethoxyanilino)-9-(tetrahydropyran-2-yl)purine,
2-thio-6-(4-ethoxyanilino)-9-(tetrahydropyran-2-yl)purine,
2-methylthio-6-(4-ethoxyanilino)-9-(tetrahydropyran-2-yl)purine,
2-chloro-6-(4-ethoxyanilino)-9-(tetrahydrofuran-2-yl)purine,
2-fluoro-6-(4-ethoxyanilino)-9-(tetrahydrofuran-2-yl)purine,
2-bromo-6-(4-ethoxyanilino)-9-(tetrahydrofuran-2-yl)purine,
2-iodo-6-(4-ethoxyanilino)-9-(tetrahydrofuran-2-yl)purine,
2-amino-6-(4-ethoxyanilino)-9-(tetrahydrofuran-2-yl)purine,
2-hydroxy-6-(4-ethoxyanilino)-9-(tetrahydrofuran-2-yl)purine,
2-thio-6-(4-ethoxyanilino)-9-(tetrahydrofuran-2-yl)purine,
2-methylthio-6-(4-ethoxyanilino)-9-(tetrahydrofuran-2-yl)purine,
2-chloro-6-(2-aminoanilino)-9-(tetrahydropyran-2-yl)purine,
2-fluoro-6-(2-aminoanilino)-9-(tetrahydropyran-2-yl)purine,
2-bromo-6-(2-aminoanilino)-9-(tetrahydropyran-2-yl)purine,
2-iodo-6-(2-aminoanilino)-9-(tetrahydropyran-2-yl)purine,
2-amino-6-(2-aminoanilino)-9-(tetrahydropyran-2-yl)purine,
2-hydroxy-6-(2-aminoanilino)-9-(tetrahydropyran-2-yl)purine,
2-thio-6-(2-aminoanilino)-9-(tetrahydropyran-2-yl)purine,
2-methylthio-6-(2-aminoanilino)-9-(tetrahydropyran-2-yl)purine,
2-chloro-6-(2-aminoanilino)-9-(tetrahydrofuran-2-yl)purine,
2-fluoro-6-(2-aminoanilino)-9-(tetrahydrofuran-2-yl)purine,
2-bromo-6-(2-aminoanilino)-9-(tetrahydrofuran-2-yl)purine,
2-iodo-6-(2-aminoanilino)-9-(tetrahydrofuran-2-yl)purine,
2-amino-6-(2-aminoanilino)-9-(tetrahydrofuran-2-yl)purine,
2-hydroxy-6-(2-aminoanilino)-9-(tetrahydrofuran-2-yl)purine,
2-thio-6-(2-aminoanilino)-9-(tetrahydrofuran-2-yl)purine,
2-methylthio-6-(2-aminoanilino)-9-(tetrahydrofuran-2-yl)purine,
2-chloro-6-(3-aminoanilino)-9-(tetrahydropyran-2-yl)purine,
2-fluoro-6-(3-aminoanilino)-9-(tetrahydropyran-2-yl)purine,
2-bromo-6-(3-aminoanilino)-9-(tetrahydropyran-2-yl)purine,
2-iodo-6-(3-aminoanilino)-9-(tetrahydropyran-2-yl)purine, 2-amino-6-(3-aminoanilino)-9-(tetrahydropyran-2-yl)purine,
2-hydroxy-6-(3-aminoanilino)-9-(tetrahydropyran-2-yl)purine,
2-thio-6-(3-aminoanilino)-9-(tetrahydropyran-2-yl)purine,
2-methylthio-6-(3-aminoanilino)-9-(tetrahydropyran-2-yl)purine,
2-chloro-6-(3-aminoanilino)-9-(tetrahydrofuran-2-yl)purine,
2-fluoro-6-(3-aminoanilino)-9-(tetrahydrofuran-2-yl)purine,
2-bromo-6-(3-aminoanilino)-9-(tetrahydrofuran-2-yl)purine,
2-iodo-6-(3-aminoanilino)-9-(tetrahydrofuran-2-yl)purine,
2-amino-6-(3-aminoanilino)-9-(tetrahydrofuran-2-yl)purine,
2-hydroxy-6-(3-aminoanilino)-9-(tetrahydrofuran-2-yl)purine,
2-thio-6-(3-aminoanilino)-9-(tetrahydrofuran-2-yl)purine,
2-methylthio-6-(3-aminoanilino)-9-(tetrahydrofuran-2-yl)purine,
2-chloro-6-(4-aminoanilino)-9-(tetrahydropyran-2-yl)purine,
2-fluoro-6-(4-aminoanilino)-9-(tetrahydropyran-2-yl)purine,
2-bromo-6-(4-aminoanilino)-9-(tetrahydropyran-2-yl)purine,
2-iodo-6-(4-aminoanilino)-9-(tetrahydropyran-2-yl)purine,
2-amino-6-(4-aminoanilino)-9-(tetrahydropyran-2-yl)purine,
2-hydroxy-6-(4-aminoanilino)-9-(tetrahydropyran-2-yl)purine,
2-thio-6-(4-aminoanilino)-9-(tetrahydropyran-2-yl)purine,
2-methylthio-6-(4-aminoanilino)-9-(tetrahydropyran-2-yl)purine,
2-chloro-6-(4-aminoanilino)-9-(tetrahydrofuran-2-yl)purine,
2-fluoro-6-(4-aminoanilino)-9-(tetrahydrofuran-2-yl)purine,
2-bromo-6-(4-aminoanilino)-9-(tetrahydrofuran-2-yl)purine,
2-iodo-6-(4-aminoanilino)-9-(tetrahydrofuran-2-yl)purine,
2-amino-6-(4-aminoanilino)-9-(tetrahydrofuran-2-yl)purine,
2-hydroxy-6-(4-aminoanilino)-9-(tetrahydrofuran-2-yl)purine,
2-thio-6-(4-aminoanilino)-9-(tetrahydrofuran-2-yl)purine,
2-methylthio-6-(4-aminoanilino)-9-(tetrahydrofuran-2-yl)purine,
2-chloro-6-(2-hydroxyanilino)-9-(tetrahydropyran-2-yl)purine,
2-fluoro-6-(2-hydroxyanilino)-9-(tetrahydropyran-2-yl)purine,
2-bromo-6-(2-hydroxyanilino)-9-(tetrahydropyran-2-yl)purine,
2-iodo-6-(2-hydroxyanilino)-9-(tetrahydropyran-2-yl)purine,
2-amino-6-(2-hydroxyanilino)-9-(tetrahydropyran-2-yl)purine,
2-hydroxy-6-(2-hydroxyanilino)-9-(tetrahydropyran-2-yl)purine,
2-thio-6-(2-hydroxyanilino)-9-(tetrahydropyran-2-yl)purine,
2-methylthio-6-(2-hydroxyanilino)-9-(tetrahydropyran-2-yl)purine,
2-chloro-6-(2-hydroxyanilino)-9-(tetrahydrofuran-2-yl)purine,
2-fluoro-6-(2-hydroxyanilino)-9-(tetrahydrofuran-2-yl)purine,
2-bromo-6-(2-hydroxyanilino)-9-(tetrahydrofuran-2-yl)purine,
2-iodo-6-(2-hydroxyanilino)-9-(tetrahydrofuran-2-yl)purine,
2-amino-6-(2-hydroxyanilino)-9-(tetrahydrofuran-2-yl)purine,
2-hydroxy-6-(2-hydroxyanilino)-9-(tetrahydrofuran-2-yl)purine,
2-thio-6-(2-hydroxyanilino)-9-(tetrahydrofuran-2-yl)purine,
2-methylthio-6-(2-hydroxyanilino)-9-(tetrahydrofuran-2-yl)purine,
2-chloro-6-(3-hydroxyanilino)-9-(tetrahydropyran-2-yl)purine,
2-fluoro-6-(3-hydroxyanilino)-9-(tetrahydropyran-2-yl)purine,
2-bromo-6-(3-hydroxyanilino)-9-(tetrahydropyran-2-yl)purine,
2-iodo-6-(3-hydroxyanilino)-9-(tetrahydropyran-2-yl)purine,
2-amino-6-(3-hydroxyanilino)-9-(tetrahydropyran-2-yl)purine,
2-hydroxy-6-(3-hydroxyanilino)-9-(tetrahydropyran-2-yl)purine,
2-thio-6-(3-hydroxyanilino)-9-(tetrahydropyran-2-yl)purine,
2-methylthio-6-(3-hydroxyanilino)-9-(tetrahydropyran-2-yl)purine,
2-chloro-6-(3-hydroxyanilino)-9-(tetrahydrofuran-2-yl)purine,
2-fluoro-6-(3-hydroxyanilino)-9-(tetrahydrofuran-2-yl)purine,
2-bromo-6-(3-hydroxyanilino)-9-(tetrahydrofuran-2-yl)purine,
2-iodo-6-(3-hydroxyanilino)-9-(tetrahydrofuran-2-yl)purine,
2-amino-6-(3-hydroxyanilino)-9-(tetrahydrofuran-2-yl)purine,
2-hydroxy-6-(3-hydroxyanilino)-9-(tetrahydrofuran-2-yl)purine,
2-thio-6-(3-hydroxyanilino)-9-(tetrahydrofuran-2-yl)purine,
2-methylthio-6-(3-hydroxyanilino)-9-(tetrahydrofuran-2-yl)purine,
2-chloro-6-(4-hydroxyanilino)-9-(tetrahydropyran-2-yl)purine,
2-fluoro-6-(4-hydroxyanilino)-9-(tetrahydropyran-2-yl)purine,
2-bromo-6-(4-hydroxyanilino)-9-(tetrahydropyran-2-yl)purine,
2-iodo-6-(4-hydroxyanilino)-9-(tetrahydropyran-2-yl)purine,
2-amino-6-(4-hydroxyanilino)-9-(tetrahydropyran-2-yl)purine,
2-hydroxy-6-(4-hydroxyanilino)-9-(tetrahydropyran-2-yl)purine, 2-thio-6-(4-hydroxyanilino)-9-(tetrahydropyran-2-yl)purine,
2-methylthio-6-(4-hydroxyanilino)-9-(tetrahydropyran-2-yl)purine,
2-chloro-6-(4-hydroxyanilino)-9-(tetrahydrofuran-2-yl)purine,
2-fluoro-6-(4-hydroxyanilino)-9-(tetrahydrofuran-2-yl)purine,
2-bromo-6-(4-hydroxyanilino)-9-(tetrahydrofuran-2-yl)purine,
2-iodo-6-(4-hydroxyanilino)-9-(tetrahydrofuran-2-yl)purine,
2-amino-6-(4-hydroxyanilino)-9-(tetrahydrofuran-2-yl)purine,
2-hydroxy-6-(4-hydroxyanilino)-9-(tetrahydrofuran-2-yl)purine,
2-thio-6-(4-hydroxyanilino)-9-(tetrahydrofuran-2-yl)purine,
2-methylthio-6-(4-hydroxyanilino)-9-(tetrahydrofuran-2-yl)purine,
2-chloro-6-(2,3-difluoroanilino)-9-(tetrahydropyran-2-yl)purine,
2-fluoro-6-(2,3-difluoroanilino)-9-(tetrahydropyran-2-yl)purine,
2-bromo-6-(2,3-difluoroanilino)-9-(tetrahydropyran-2-yl)purine,
2-iodo-6-(2,3-difluoroanilino)-9-(tetrahydropyran-2-yl)purine,
2-amino-6-(2,3-difluoroanilino)-9-(tetrahydropyran-2-yl)purine,
2-hydroxy-6-(2,3-difluoroanilino)-9-(tetrahydropyran-2-yl)purine,
2-thio-6-(2,3-difluoroanilino)-9-(tetrahydropyran-2-yl)purine,
2-methylthio-6-(2,3-difluoroanilino)-9-(tetrahydropyran-2-yl)purine,
2-chloro-6-(2,3-difluoroanilino)-9-(tetrahydrofuran-2-yl)purine,
2-fluoro-6-(2,3-difluoroanilino)-9-(tetrahydrofuran-2-yl)purine,
2-bromo-6-(2,3-difluoroanilino)-9-(tetrahydrofuran-2-yl)purine,
2-iodo-6-(2,3-difluoroanilino)-9-(tetrahydrofuran-2-yl)purine,
2-amino-6-(2,3-difluoroanilino)-9-(tetrahydrofuran-2-yl)purine,
2-hydroxy-6-(2,3-difluoroanilino)-9-(tetrahydrofuran-2-yl)purine,
2-thio-6-(2,3-difluoroanilino)-9-(tetrahydrofuran-2-yl)purine,
2-methylthio-6-(2,3-difluoroanilino)-9-(tetrahydrofuran-2-yl)purine,
2-chloro-6-(2,4-difluoroanilino)-9-(tetrahydropyran-2-yl)purine,
2-fluoro-6-(2,4-difluoroanilino)-9-(tetrahydropyran-2-yl)purine,
2-bromo-6-(2,4-difluoroanilino)-9-(tetrahydropyran-2-yl)purine,
2-iodo-6-(2,4-difluoroanilino)-9-(tetrahydropyran-2-yl)purine,
2-amino-6-(2,4-difluoroanilino)-9-(tetrahydropyran-2-yl)purine,
2-hydroxy-6-(2,4-difluoroanilino)-9-(tetrahydropyran-2-yl)purine,
2-thio-6-(2,4-difluoroanilino)-9-(tetrahydropyran-2-yl)purine,
2-methylthio-6-(2,4-difluoroanilino)-9-(tetrahydropyran-2-yl)purine,
2-chloro-6-(2,4-difluoroanilino)-9-(tetrahydrofuran-2-yl)purine,
2-fluoro-6-(2,4-difluoroanilino)-9-(tetrahydrofuran-2-yl)purine,
2-bromo-6-(2,4-difluoroanilino)-9-(tetrahydrofuran-2-yl)purine,
2-iodo-6-(2,4-difluoroanilino)-9-(tetrahydrofuran-2-yl)purine,
2-amino-6-(2,4-difluoroanilino)-9-(tetrahydrofuran-2-yl)purine,
2-hydroxy-6-(2,4-difluoroanilino)-9-(tetrahydrofuran-2-yl)purine,
2-thio-6-(2,4-difluoroanilino)-9-(tetrahydrofuran-2-yl)purine,
2-methylthio-6-(2,4-difluoroanilino)-9-(tetrahydrofuran-2-yl)purine,
2-chloro-6-(2,3,4-trifluoroanilino)-9-(tetrahydropyran-2-yl)purine,
2-fluoro-6-(2,3,4-trifluoroanilino)-9-(tetrahydropyran-2-yl)purine,
2-bromo-6-(2,3,4-trifluoroanilino)-9-(tetrahydropyran-2-yl)purine,
2-iodo-6-(2,3,4-trifluoroanilino)-9-(tetrahydropyran-2-yl)purine,
2-amino-6-(2,3,4-trifluoroanilino)-9-(tetrahydropyran-2-yl)purine,
2-hydroxy-6-(2,3,4-trifluoroanilino)-9-(tetrahydropyran-2-yl)purine,
2-thio-6-(2,3,4-trifluoroanilino)-9-(tetrahydropyran-2-yl)purine,
2-methylthio-6-(2,3,4-trifluoroanilino)-9-(tetrahydropyran-2-yl)purine,
2-chloro-6-(2,3,4-trifluoroanilino)-9-(tetrahydrofuran-2-yl)purine,
2-fluoro-6-(2,3,4-trifluoroanilino)-9-(tetrahydrofuran-2-yl)purine,
2-bromo-6-(2,3,4-trifluoroanilino)-9-(tetrahydrofuran-2-yl)purine,
2-iodo-6-(2,3,4-trifluoroanilino)-9-(tetrahydrofuran-2-yl)purine,
2-amino-6-(2,3,4-trifluoroanilino)-9-(tetrahydrofuran-2-yl)purine,
2-hydroxy-6-(2,3,4-trifluoroanilino)-9-(tetrahydrofuran-2-yl)purine,
2-thio-6-(2,3,4-trifluoroanilino)-9-(tetrahydrofuran-2-yl)purine,
2-methylthio-6-(2,3,4-trifluoroanilino)-9-(tetrahydrofuran-2-yl)purine,
2-chloro-6-(2,4,5-trifluoroanilino)-9-(tetrahydropyran-2-yl)purine,
2-fluoro-6-(2,4,5-trifluoroanilino)-9-(tetrahydropyran-2-yl)purine,
2-bromo-6-(2,4,5-trifluoroanilino)-9-(tetrahydropyran-2-yl)purine,
2-iodo-6-(2,4,5-trifluoroanilino)-9-(tetrahydropyran-2-yl)purine,
2-amino-6-(2,4,5-trifluoroanilino)-9-(tetrahydropyran-2-yl)purine,
2-hydroxy-6-(2,4,5-trifluoroanilino)-9-(tetrahydropyran-2-yl)purine,
2-thio-6-(2,4,5-trifluoroanilino)-9-(tetrahydropyran-2-yl)purine,
2-methylthio-6-(2,4,5-trifluoroanilino)-9-(tetrahydropyran-2-yl)purine, 2-chloro-6-(2,4,5-trifluoroanilino)-9-(tetrahydrofuran-2-yl)purine,
2-fluoro-6-(2,4,5-trifluoroanilino)-9-(tetrahydrofuran-2-yl)purine,
2-bromo-6-(2,4,5-trifluoroanilino)-9-(tetrahydrofuran-2-yl)purine,
2-iodo-6-(2,4,5-trifluoroanilino)-9-(tetrahydrofuran-2-yl)purine,
2-amino-6-(2,4,5-trifluoroanilino)-9-(tetrahydrofuran-2-yl)purine,
2-hydroxy-6-(2,4,5-trifluoroanilino)-9-(tetrahydrofuran-2-yl)purine,
2-thio-6-(2,4,5-trifluoroanilino)-9-(tetrahydrofuran-2-yl)purine,
2-methylthio-6-(2,4,5-trifluoroanilino)-9-(tetrahydrofuran-2-yl)purine,
2-chloro-6-(2,3-dichloroanilino)-9-(tetrahydropyran-2-yl)purine,
2-fluoro-6-(2,3-dichloroanilino)-9-(tetrahydropyran-2-yl)purine,
2-bromo-6-(2,3-dichloroanilino)-9-(tetrahydropyran-2-yl)purine,
2-iodo-6-(2,3-dichloroanilino)-9-(tetrahydropyran-2-yl)purine,
2-amino-6-(2,3-dichloroanilino)-9-(tetrahydropyran-2-yl)purine,
2-hydroxy-6-(2,3-dichloroanilino)-9-(tetrahydropyran-2-yl)purine,
2-thio-6-(2,3-dichloroanilino)-9-(tetrahydropyran-2-yl)purine,
2-methylthio-6-(2,3-dichloroanilino)-9-(tetrahydropyran-2-yl)purine,
2-chloro-6-(2,3-dichloroanilino)-9-(tetrahydrofuran-2-yl)purine,
2-fluoro-6-(2,3-dichloroanilino)-9-(tetrahydrofuran-2-yl)purine,
2-bromo-6-(2,3-dichloroanilino)-9-(tetrahydrofuran-2-yl)purine,
2-iodo-6-(2,3-dichloroanilino)-9-(tetrahydrofuran-2-yl)purine,
2-amino-6-(2,3-dichloroanilino)-9-(tetrahydrofuran-2-yl)purine,
2-hydroxy-6-(2,3-dichloroanilino)-9-(tetrahydrofuran-2-yl)purine,
2-thio-6-(2,3-dichloroanilino)-9-(tetrahydrofuran-2-yl)purine,
2-methylthio-6-(2,3-dichloroanilino)-9-(tetrahydrofuran-2-yl)purine,
2-chloro-6-(2,4-dichloroanilino)-9-(tetrahydropyran-2-yl)purine,
2-fluoro-6-(2,4-dichloroanilino)-9-(tetrahydropyran-2-yl)purine,
2-bromo-6-(2,4-dichloroanilino)-9-(tetrahydropyran-2-yl)purine,
2-iodo-6-(2,4-dichloroanilino)-9-(tetrahydropyran-2-yl)purine,
2-amino-6-(2,4-dichloroanilino)-9-(tetrahydropyran-2-yl)purine,
2-hydroxy-6-(2,4-dichloroanilino)-9-(tetrahydropyran-2-yl)purine,
2-thio-6-(2,4-dichloroanilino)-9-(tetrahydropyran-2-yl)purine,
2-methylthio-6-(2,4-dichloroanilino)-9-(tetrahydropyran-2-yl)purine,
2-chloro-6-(2,4-dichloroanilino)-9-(tetrahydrofuran-2-yl)purine,
2-fluoro-6-(2,4-dichloroanilino)-9-(tetrahydrofuran-2-yl)purine,
2-bromo-6-(2,4-dichloroanilino)-9-(tetrahydrofuran-2-yl)purine,
2-iodo-6-(2,4-dichloroanilino)-9-(tetrahydrofuran-2-yl)purine,
2-amino-6-(2,4-dichloroanilino)-9-(tetrahydrofuran-2-yl)purine,
2-hydroxy-6-(2,4-dichloroanilino)-9-(tetrahydrofuran-2-yl)purine,
2-thio-6-(2,4-dichloroanilino)-9-(tetrahydrofuran-2-yl)purine,
2-methylthio-6-(2,4-dichloroanilino)-9-(tetrahydrofuran-2-yl)purine,
2-chloro-6-(2,4-dimethoxyanilino)-9-(tetrahydropyran-2-yl)purine,
2-fluoro-6-(2,4-dimethoxyanilino)-9-(tetrahydropyran-2-yl)purine,
2-bromo-6-(2,4-dimethoxyanilino)-9-(tetrahydropyran-2-yl)purine,
2-iodo-6-(2,4-dimethoxyanilino)-9-(tetrahydropyran-2-yl)purine,
2-amino-6-(2,4-dimethoxyanilino)-9-(tetrahydropyran-2-yl)purine,
2-hydroxy-6-(2,4-dimethoxyanilino)-9-(tetrahydropyran-2-yl)purine,
2-thio-6-(2,4-dimethoxyanilino)-9-(tetrahydropyran-2-yl)purine,
2-methylthio-6-(2,4-dimethoxyanilino)-9-(tetrahydropyran-2-yl)purine,
2-chloro-6-(2,4-dimethoxyanilino)-9-(tetrahydrofuran-2-yl)purine,
2-fluoro-6-(2,4-dimethoxyanilino)-9-(tetrahydrofuran-2-yl)purine,
2-bromo-6-(2,4-dimethoxyanilino)-9-(tetrahydrofuran-2-yl)purine,
2-iodo-6-(2,4-dimethoxyanilino)-9-(tetrahydrofuran-2-yl)purine,
2-amino-6-(2,4-dimethoxyanilino)-9-(tetrahydrofuran-2-yl)purine,
2-hydroxy-6-(2,4-dimethoxyanilino)-9-(tetrahydrofuran-2-yl)purine,
2-thio-6-(2,4-dimethoxyanilino)-9-(tetrahydrofuran-2-yl)purine,
2-methylthio-6-(2,4-dimethoxyanilino)-9-(tetrahydrofuran-2-yl)purine,
2-chloro-6-(2,3-dimethoxyanilino)-9-(tetrahydropyran-2-yl)purine,
2-fluoro-6-(2,3-dimethoxyanilino)-9-(tetrahydropyran-2-yl)purine,
2-bromo-6-(2,3-dimethoxyanilino)-9-(tetrahydropyran-2-yl)purine,
2-iodo-6-(2,3-dimethoxyanilino)-9-(tetrahydropyran-2-yl)purine,
2-amino-6-(2,3-dimethoxyanilino)-9-(tetrahydropyran-2-yl)purine,
2-thio-6-(2,3-dimethoxyanilino)-9-(tetrahydropyran-2-yl)purine,
2-methylthio-6-(2,3-dimethoxyanilino)-9-(tetrahydropyran-2-yl)purine,
2-chloro-6-(2,3-dimethoxyanilino)-9-(tetrahydrofuran-2-yl)purine,
2-fluoro-6-(2,3-dimethoxyanilino)-9-(tetrahydrofuran-2-yl)purine,
2-bromo-6-(2,3-dimethoxyanilino)-9-(tetrahydrofuran-2-yl)purine, 2-iodo-6-(2,3-dimethoxyanilino)-9-(tetrahydrofuran-2-yl)purine,
2-amino-6-(2,3-dimethoxyanilino)-9-(tetrahydrofuran-2-yl)purine,
2-thio-6-(2,3-dimethoxyanilino)-9-(tetrahydrofuran-2-yl)purine,
2-methylthio-6-(2,3-dimethoxyanilino)-9-(tetrahydrofuran-2-yl)purine,
2-chloro-6-(3,4-dimethoxyanilino)-9-(tetrahydropyran-2-yl)purine,
2-fluoro-6-(3,4-dimethoxyanilino)-9-(tetrahydropyran-2-yl)purine,
2-bromo-6-(3,4-dimethoxyanilino)-9-(tetrahydropyran-2-yl)purine,
2-iodo-6-(3,4-dimethoxyanilino)-9-(tetrahydropyran-2-yl)purine,
2-amino-6-(3,4-dimethoxyanilino)-9-(tetrahydropyran-2-yl)purine,
2-hydroxy-6-(3,4-dimethoxyanilino)-9-(tetrahydropyran-2-yl)purine,
2-thio-6-(3,4-dimethoxyanilino)-9-(tetrahydropyran-2-yl)purine,
2-methylthio-6-(3,4-dimethoxyanilino)-9-(tetrahydropyran-2-yl)purine,
2-chloro-6-(3,4-dimethoxyanilino)-9-(tetrahydrofuran-2-yl)purine,
2-fluoro-6-(3,4-dimethoxyanilino)-9-(tetrahydrofuran-2-yl)purine,
2-bromo-6-(3,4-dimethoxyanilino)-9-(tetrahydrofuran-2-yl)purine,
2-iodo-6-(3,4-dimethoxyanilino)-9-(tetrahydrofuran-2-yl)purine,
2-amino-6-(3,4-dimethoxyanilino)-9-(tetrahydrofuran-2-yl)purine,
2-hydroxy-6-(3,4-dimethoxyanilino)-9-(tetrahydrofuran-2-yl)purine,
2-thio-6-(3,4-dimethoxyanilino)-9-(tetrahydrofuran-2-yl)purine,
2-methylthio-6-(3,4-dimethoxyanilino)-9-(tetrahydrofuran-2-yl)purine,
2-chloro-6-(2,5-dimethoxyanilino)-9-(tetrahydropyran-2-yl)purine,
2-fluoro-6-(2,5-dimethoxyanilino)-9-(tetrahydropyran-2-yl)purine,
2-bromo-6-(2,5-dimethoxyanilino)-9-(tetrahydropyran-2-yl)purine,
2-iodo-6-(2,5-dimethoxyanilino)-9-(tetrahydropyran-2-yl)purine,
2-amino-6-(2,5-dimethoxyanilino)-9-(tetrahydropyran-2-yl)purine,
2-hydroxy-6-(2,5-dimethoxyanilino)-9-(tetrahydropyran-2-yl)purine,
2-thio-6-(2,5-dimethoxyanilino)-9-(tetrahydropyran-2-yl)purine,
2-methylthio-6-(2,5-dimethoxyanilino)-9-(tetrahydropyran-2-yl)purine,
2-chloro-6-(2,5-dimethoxyanilino)-9-(tetrahydrofuran-2-yl)purine,
2-fluoro-6-(2,5-dimethoxyanilino)-9-(tetrahydrofuran-2-yl)purine,
2-bromo-6-(2,5-dimethoxyanilino)-9-(tetrahydrofuran-2-yl)purine,
2-iodo-6-(2,5-dimethoxyanilino)-9-(tetrahydrofuran-2-yl)purine,
2-amino-6-(2,5-dimethoxyanilino)-9-(tetrahydrofuran-2-yl)purine,
2-hydroxy-6-(2,5-dimethoxyanilino)-9-(tetrahydrofuran-2-yl)purine,
2-thio-6-(2,5-dimethoxyanilino)-9-(tetrahydrofuran-2-yl)purine,
2-methylthio-6-(2,5-dimethoxyanilino)-9-(tetrahydrofuran-2-yl)purine,
2-chloro-6-(3,4,5-trimethoxyanilino)-9-(tetrahydropyran-2-yl)purine,
2-fluoro-6-(3,4,5-trimethoxyanilino)-9-(tetrahydropyran-2-yl)purine,
2-bromo-6-(3,4,5-trimethoxyanilino)-9-(tetrahydropyran-2-yl)purine,
2-iodo-6-(3,4,5-trimethoxyanilino)-9-(tetrahydropyran-2-yl)purine,
2-amino-6-(3,4,5-trimethoxyanilino)-9-(tetrahydropyran-2-yl)purine,
2-hydroxy-6-(3,4,5-trimethoxyanilino)-9-(tetrahydropyran-2-yl)purine,
2-thio-6-(3,4,5-trimethoxyanilino)-9-(tetrahydropyran-2-yl)purine,
2-methylthio-6-(3,4,5-trimethoxyanilino)-9-(tetrahydropyran-2-yl)purine,
2-chloro-6-(3,4,5-trimethoxyanilino)-9-(tetrahydrofuran-2-yl)purine,
2-fluoro-6-(3,4,5-trimethoxyanilino)-9-(tetrahydrofuran-2-yl)purine,
2-bromo-6-(3,4,5-trimethoxyanilino)-9-(tetrahydrofuran-2-yl)purine,
2-iodo-6-(3,4,5-trimethoxyanilino)-9-(tetrahydrofuran-2-yl)purine,
2-amino-6-(3,4,5-trimethoxyanilino)-9-(tetrahydrofuran-2-yl)purine,
2-hydroxy-6-(3,4,5-trimethoxyanilino)-9-(tetrahydrofuran-2-yl)purine,
2-thio-6-(3,4,5-trimethoxyanilino)-9-(tetrahydrofuran-2-yl)purine,
2-methylthio-6-(3,4,5-trimethoxyanilino)-9-(tetrahydrofuran-2-yl)purine,
2-chloro-6-(2,4,6-trimethoxyanilino)-9-(tetrahydropyran-2-yl)purine,
2-fluoro-6-(2,4,6-trimethoxyanilino)-9-(tetrahydropyran-2-yl)purine,
2-bromo-6-(2,4,6-trimethoxyanilino)-9-(tetrahydropyran-2-yl)purine,
2-iodo-6-(2,4,6-trimethoxyanilino)-9-(tetrahydropyran-2-yl)purine,
2-amino-6-(2,4,6-trimethoxyanilino)-9-(tetrahydropyran-2-yl)purine,
2-hydroxy-6-(2,4,6-trimethoxyanilino)-9-(tetrahydropyran-2-yl)purine,
2-thio-6-(2,4,6-trimethoxyanilino)-9-(tetrahydropyran-2-yl)purine,
2-methylthio-6-(2,4,6-trimethoxyanilino)-9-(tetrahydropyran-2-yl)purine,
2-chloro-6-(2,4,6-trimethoxyanilino)-9-(tetrahydrofuran-2-yl)purine,
2-fluoro-6-(2,4,6-trimethoxyanilino)-9-(tetrahydrofuran-2-yl)purine,
2-bromo-6-(2,4,6-trimethoxyanilino)-9-(tetrahydrofuran-2-yl)purine,
2-iodo-6-(2,4,6-trimethoxyanilino)-9-(tetrahydrofuran-2-yl)purine,
2-amino-6-(2,4,6-trimethoxyanilino)-9-(tetrahydrofuran-2-yl)purine,
2-hydroxy-6-(2,4,6-trimethoxyanilino)-9-(tetrahydrofuran-2-yl)purine, 2-thio-6-(2,4,6-trimethoxyanilino)-9-(tetrahydrofuran-2-yl)purine,
2-methylthio-6-(2,4,6-trimethoxyanilino)-9-(tetrahydrofuran-2-yl)purine,
2-chloro-6-(2,3-dihydroxyanilino)-9-(tetrahydropyran-2-yl)purine,
2-fluoro-6-(2,3-dihydroxyanilino)-9-(tetrahydropyran-2-yl)purine,
2-bromo-6-(2,3-dihydroxyanilino)-9-(tetrahydropyran-2-yl)purine,
2-iodo-6-(2,3-dihydroxyanilino)-9-(tetrahydropyran-2-yl)purine,
2-amino-6-(2,3-dihydroxyanilino)-9-(tetrahydropyran-2-yl)purine,
2-hydroxy-6-(2,3-dihydroxyanilino)-9-(tetrahydropyran-2-yl)purine,
2-thio-6-(2,3-dihydroxyanilino)-9-(tetrahydropyran-2-yl)purine,
2-methylthio-6-(2,3-dihydroxyanilino)-9-(tetrahydropyran-2-yl)purine,
2-chloro-6-(2,3-dihydroxyanilino)-9-(tetrahydrofuran-2-yl)purine,
2-fluoro-6-(2,3-dihydroxyanilino)-9-(tetrahydrofuran-2-yl)purine,
2-bromo-6-(2,3-dihydroxyanilino)-9-(tetrahydrofuran-2-yl)purine,
2-iodo-6-(2,3-dihydroxyanilino)-9-(tetrahydrofuran-2-yl)purine,
2-amino-6-(2,3-dihydroxyanilino)-9-(tetrahydrofuran-2-yl)purine,
2-hydroxy-6-(2,3-dihydroxyanilino)-9-(tetrahydrofuran-2-yl)purine,
2-thio-6-(2,3-dihydroxyanilino)-9-(tetrahydrofuran-2-yl)purine,
2-methylthio-6-(2,3-dihydroxyanilino)-9-(tetrahydrofuran-2-yl)purine,
2-chloro-6-(2,4-dihydroxyanilino)-9-(tetrahydropyran-2-yl)purine,
2-fluoro-6-(2,4-dihydroxyanilino)-9-(tetrahydropyran-2-yl)purine,
2-bromo-6-(2,4-dihydroxyanilino)-9-(tetrahydropyran-2-yl)purine,
2-iodo-6-(2,4-dihydroxyanilino)-9-(tetrahydropyran-2-yl)purine,
2-amino-6-(2,4-dihydroxyanilino)-9-(tetrahydropyran-2-yl)purine,
2-hydroxy-6-(2,4-dihydroxyanilino)-9-(tetrahydropyran-2-yl)purine,
2-thio-6-(2,4-dihydroxyanilino)-9-(tetrahydropyran-2-yl)purine,
2-methylthio-6-(2,4-dihydroxyanilino)-9-(tetrahydropyran-2-yl)purine,
2-chloro-6-(2,4-dihydroxyanilino)-9-(tetrahydrofuran-2-yl)purine,
2-fluoro-6-(2,4-dihydroxyanilino)-9-(tetrahydrofuran-2-yl)purine,
2-bromo-6-(2,4-dihydroxyanilino)-9-(tetrahydrofuran-2-yl)purine,
2-iodo-6-(2,4-dihydroxyanilino)-9-(tetrahydrofuran-2-yl)purine,
2-amino-6-(2,4-dihydroxyanilino)-9-(tetrahydrofuran-2-yl)purine,
2-hydroxy-6-(2,4-dihydroxyanilino)-9-(tetrahydrofuran-2-yl)purine,
2-thio-6-(2,4-dihydroxyanilino)-9-(tetrahydrofuran-2-yl)purine,
2-methylthio-6-(2,4-dihydroxyanilino)-9-(tetrahydrofuran-2-yl)purine,
2-chloro-6-(2,5-dihydroxyanilino)-9-(tetrahydropyran-2-yl)purine,
2-fluoro-6-(2,5-dihydroxyanilino)-9-(tetrahydropyran-2-yl)purine,
2-bromo-6-(2,5-dihydroxyanilino)-9-(tetrahydropyran-2-yl)purine,
2-iodo-6-(2,5-dihydroxyanilino)-9-(tetrahydropyran-2-yl)purine,
2-amino-6-(2,5-dihydroxyanilino)-9-(tetrahydropyran-2-yl)purine,
2-hydroxy-6-(2,5-dihydroxyanilino)-9-(tetrahydropyran-2-yl)purine,
2-thio-6-(2,5-dihydroxyanilino)-9-(tetrahydropyran-2-yl)purine,
2-methylthio-6-(2,5-dihydroxyanilino)-9-(tetrahydropyran-2-yl)purine,
2-chloro-6-(2,5-dihydroxyanilino)-9-(tetrahydrofuran-2-yl)purine,
2-fluoro-6-(2,5-dihydroxyanilino)-9-(tetrahydrofuran-2-yl)purine,
2-bromo-6-(2,5-dihydroxyanilino)-9-(tetrahydrofuran-2-yl)purine,
2-iodo-6-(2,5-dihydroxyanilino)-9-(tetrahydrofuran-2-yl)purine,
2-amino-6-(2,5-dihydroxyanilino)-9-(tetrahydrofuran-2-yl)purine,
2-hydroxy-6-(2,5-dihydroxyanilino)-9-(tetrahydrofuran-2-yl)purine,
2-thio-6-(2,5-dihydroxyanilino)-9-(tetrahydrofuran-2-yl)purine,
2-methylthio-6-(2,5-dihydroxyanilino)-9-(tetrahydrofuran-2-yl)purine,
2-chloro-6-(3,5-dihydroxyanilino)-9-(tetrahydropyran-2-yl)purine,
2-fluoro-6-(3,5-dihydroxyanilino)-9-(tetrahydropyran-2-yl)purine,
2-bromo-6-(3,5-dihydroxyanilino)-9-(tetrahydropyran-2-yl)purine,
2-iodo-6-(3,5-dihydroxyanilino)-9-(tetrahydropyran-2-yl)purine,
2-amino-6-(3,5-dihydroxyanilino)-9-(tetrahydropyran-2-yl)purine,
2-hydroxy-6-(3,5-dihydroxyanilino)-9-(tetrahydropyran-2-yl)purine,
2-thio-6-(3,5-dihydroxyanilino)-9-(tetrahydropyran-2-yl)purine,
2-methylthio-6-(3,5-dihydroxyanilino)-9-(tetrahydropyran-2-yl)purine,
2-chloro-6-(3,5-dihydroxyanilino)-9-(tetrahydrofuran-2-yl)purine,
2-fluoro-6-(3,5-dihydroxyanilino)-9-(tetrahydrofuran-2-yl)purine,
2-bromo-6-(3,5-dihydroxyanilino)-9-(tetrahydrofuran-2-yl)purine,
2-iodo-6-(3,5-dihydroxyanilino)-9-(tetrahydrofuran-2-yl)purine,
2-amino-6-(3,5-dihydroxyanilino)-9-(tetrahydrofuran-2-yl)purine,
2-hydroxy-6-(3,5-dihydroxyanilino)-9-(tetrahydrofuran-2-yl)purine,
2-thio-6-(3,5-dihydroxyanilino)-9-(tetrahydrofuran-2-yl)purine,
2-methylthio-6-(3,5-dihydroxyanilino)-9-(tetrahydrofuran-2-yl)purine, 2-chloro-6-(3-hydroxy-2-methoxyanilino)-9-(tetrahydropyran-2-yl)purine,
2-fluoro-6-(3-hydroxy-2-methoxyanilino)-9-(tetrahydropyran-2-yl)purine,
2-bromo-6-(3-hydroxy-2-methoxyanilino)-9-(tetrahydropyran-2-yl)purine,
2-iodo-6-(3-hydroxy-2-methoxyanilino)-9-(tetrahydropyran-2-yl)purine,
2-amino-6-(3-hydroxy-2-methoxyanilino)-9-(tetrahydropyran-2-yl)purine,
2-hydroxy-6-(3-hydroxy-2-methoxyanilino)-9-(tetrahydropyran-2-yl)purine,
2-thio-6-(3-hydroxy-2-methoxyanilino)-9-(tetrahydropyran-2-yl)purine,
2-methylthio-6-(3-hydroxy-2-methoxyanilino)-9-(tetrahydropyran-2-yl)purine,
2-chloro-6-(3-hydroxy-2-methoxyanilino)-9-(tetrahydrofuran-2-yl)purine,
2-fluoro-6-(3-hydroxy-2-methoxyanilino)-9-(tetrahydrofuran-2-yl)purine,
2-bromo-6-(3-hydroxy-2-methoxyanilino)-9-(tetrahydrofuran-2-yl)purine,
2-iodo-6-(3-hydroxy-2-methoxyanilino)-9-(tetrahydrofuran-2-yl)purine,
2-amino-6-(3-hydroxy-2-methoxyanilino)-9-(tetrahydrofuran-2-yl)purine,
2-hydroxy-6-(3-hydroxy-2-methoxyanilino)-9-(tetrahydrofuran-2-yl)purine,
2-thio-6-(3-hydroxy-2-methoxyanilino)-9-(tetrahydrofuran-2-yl)purine,
2-methylthio-6-(3-hydroxy-2-methoxyanilino)-9-(tetrahydrofuran-2-yl)purine,
2-chloro-6-(3-hydroxy-4-methoxyanilino)-9-(tetrahydropyran-2-yl)purine,
2-fluoro-6-(3-hydroxy-4-methoxyanilino)-9-(tetrahydropyran-2-yl)purine,
2-bromo-6-(3-hydroxy-4-methoxyanilino)-9-(tetrahydropyran-2-yl)purine,
2-iodo-6-(3-hydroxy-4-methoxyanilino)-9-(tetrahydropyran-2-yl)purine,
2-amino-6-(3-hydroxy-4-methoxyanilino)-9-(tetrahydropyran-2-yl)purine,
2-hydroxy-6-(3-hydroxy-4-methoxyanilino)-9-(tetrahydropyran-2-yl)purine,
2-thio-6-(3-hydroxy-4-methoxyanilino)-9-(tetrahydropyran-2-yl)purine,
2-methylthio-6-(3-hydroxy-4-methoxyanilino)-9-(tetrahydropyran-2-yl)purine,
2-chloro-6-(3-hydroxy-4-methoxyanilino)-9-(tetrahydrofuran-2-yl)purine,
2-fluoro-6-(3-hydroxy-4-methoxyanilino)-9-(tetrahydrofuran-2-yl)purine,
2-bromo-6-(3-hydroxy-4-methoxyanilino)-9-(tetrahydrofuran-2-yl)purine,
2-iodo-6-(3-hydroxy-4-methoxyanilino)-9-(tetrahydrofuran-2-yl)purine,
2-amino-6-(3-hydroxy-4-methoxyanilino)-9-(tetrahydrofuran-2-yl)purine,
2-hydroxy-6-(3-hydroxy-4-methoxyanilino)-9-(tetrahydrofuran-2-yl)purine,
2-thio-6-(3-hydroxy-4-methoxyanilino)-9-(tetrahydrofuran-2-yl)purine,
2-methylthio-6-(3-hydroxy-4-methoxyanilino)-9-(tetrahydrofuran-2-yl)purine,
2-chloro-6-(2-hydroxy-3-methoxyanilino)-9-(tetrahydropyran-2-yl)purine,
2-fluoro-6-(2-hydroxy-3-methoxyanilino)-9-(tetrahydropyran-2-yl)purine,
2-bromo-6-(2-hydroxy-3-methoxyanilino)-9-(tetrahydropyran-2-yl)purine,
2-iodo-6-(2-hydroxy-3-methoxyanilino)-9-(tetrahydropyran-2-yl)purine,
2-amino-6-(2-hydroxy-3-methoxyanilino)-9-(tetrahydropyran-2-yl)purine,
2-hydroxy-6-(2-hydroxy-3-methoxyanilino)-9-(tetrahydropyran-2-yl)purine,
2-thio-6-(2-hydroxy-3-methoxyanilino)-9-(tetrahydropyran-2-yl)purine,
2-methylthio-6-(2-hydroxy-3-methoxyanilino)-9-(tetrahydropyran-2-yl)purine,
2-chloro-6-(2-hydroxy-3-methoxyanilino)-9-(tetrahydrofuran-2-yl)purine,
2-fluoro-6-(2-hydroxy-3-methoxyanilino)-9-(tetrahydrofuran-2-yl)purine,
2-bromo-6-(2-hydroxy-3-methoxyanilino)-9-(tetrahydrofuran-2-yl)purine,
2-iodo-6-(2-hydroxy-3-methoxyanilino)-9-(tetrahydrofuran-2-yl)purine,
2-amino-6-(2-hydroxy-3-methoxyanilino)-9-(tetrahydrofuran-2-yl)purine,
2-hydroxy-6-(2-hydroxy-3-methoxyanilino)-9-(tetrahydrofuran-2-yl)purine,
2-thio-6-(2-hydroxy-3-methoxyanilino)-9-(tetrahydrofuran-2-yl)purine,
2-methylthio-6-(2-hydroxy-3-methoxyanilino)-9-(tetrahydrofuran-2-yl)purine,
2-chloro-6-(2-hydroxy-5-methoxyanilino)-9-(tetrahydropyran-2-yl)purine,
2-fluoro-6-(2-hydroxy-5-methoxyanilino)-9-(tetrahydropyran-2-yl)purine,
2-bromo-6-(2-hydroxy-5-methoxyanilino)-9-(tetrahydropyran-2-yl)purine,
2-iodo-6-(2-hydroxy-5-methoxyanilino)-9-(tetrahydropyran-2-yl)purine,
2-amino-6-(2-hydroxy-5-methoxyanilino)-9-(tetrahydropyran-2-yl)purine,
2-hydroxy-6-(2-hydroxy-5-methoxyanilino)-9-(tetrahydropyran-2-yl)purine,
2-thio-6-(2-hydroxy-5-methoxyanilino)-9-(tetrahydropyran-2-yl)purine,
2-methylthio-6-(2-hydroxy-5-methoxyanilino)-9-(tetrahydropyran-2-yl)purine,
2-chloro-6-(2-hydroxy-5-methoxyanilino)-9-(tetrahydrofuran-2-yl)purine,
2-fluoro-6-(2-hydroxy-5-methoxyanilino)-9-(tetrahydrofuran-2-yl)purine,
2-bromo-6-(2-hydroxy-5-methoxyanilino)-9-(tetrahydrofuran-2-yl)purine,
2-iodo-6-(2-hydroxy-5-methoxyanilino)-9-(tetrahydrofuran-2-yl)purine,
2-amino-6-(2-hydroxy-5-methoxyanilino)-9-(tetrahydrofuran-2-yl)purine,
2-hydroxy-6-(2-hydroxy-5-methoxyanilino)-9-(tetrahydrofuran-2-yl)purine,
2-thio-6-(2-hydroxy-5-methoxyanilino)-9-(tetrahydrofuran-2-yl)purine,
2-methylthio-6-(2-hydroxy-5-methoxyanilino)-9-(tetrahydrofuran-2-yl)purine,
2-chloro-6-(4-hydroxy-3,5-dimethoxyanilino)-9-(tetrahydropyran-2-yl)purine,
2-fluoro-6-(4-hydroxy-3,5-dimethoxyanilino)-9-(tetrahydropyran-2-yl)purine, 2-bromo-6-(4-hydroxy-3,5-dimethoxyanilino)-9-(tetrahydropyran-2-yl)purine,
2-iodo-6-(4-hydroxy-3,5-dimethoxyanilino)-9-(tetrahydropyran-2-yl)purine,
2-amino-6-(4-hydroxy-3,5-dimethoxyanilino)-9-(tetrahydropyran-2-yl)purine,
2-hydroxy-6-(4-hydroxy-3,5-dimethoxyanilino)-9-(tetrahydropyran-2-yl)purine,
2-thio-6-(4-hydroxy-3,5-dimethoxyanilino)-9-(tetrahydropyran-2-yl)purine,
2-methylthio-6-(4-hydroxy-3,5-dimethoxyanilino)-9-(tetrahydropyran-2-yl)purine,
2-chloro-6-(4-hydroxy-3,5-dimethoxyanilino)-9-(tetrahydrofuran-2-yl)purine,
2-fluoro-6-(4-hydroxy-3,5-dimethoxyanilino)-9-(tetrahydrofuran-2-yl)purine,
2-bromo-6-(4-hydroxy-3,5-dimethoxyanilino)-9-(tetrahydrofuran-2-yl)purine,
2-iodo-6-(4-hydroxy-3,5-dimethoxyanilino)-9-(tetrahydrofuran-2-yl)purine,
2-amino-6-(4-hydroxy-3,5-dimethoxyanilino)-9-(tetrahydrofuran-2-yl)purine,
2-hydroxy-6-(4-hydroxy-3,5-dimethoxyanilino)-9-(tetrahydrofuran-2-yl)purine,
2-thio-6-(4-hydroxy-3,5-dimethoxyanilino)-9-(tetrahydrofuran-2-yl)purine,
2-methylthio-6-(4-hydroxy-3,5-dimethoxyanilino)-9-(tetrahydrofuran-2-yl)purine,
2-chloro-6-(2-chloro-4-methoxyanilino)-9-(tetrahydropyran-2-yl)purine,
2-fluoro-6-(2-chloro-4-methoxyanilino)-9-(tetrahydropyran-2-yl)purine,
2-bromo-6-(2-chloro-4-methoxyanilino)-9-(tetrahydropyran-2-yl)purine,
2-iodo-6-(2-chloro-4-methoxyanilino)-9-(tetrahydropyran-2-yl)purine,
2-amino-6-(2-chloro-4-methoxyanilino)-9-(tetrahydropyran-2-yl)purine,
2-hydroxy-6-(2-chloro-4-methoxyanilino)-9-(tetrahydropyran-2-yl)purine,
2-thio-6-(2-chloro-4-methoxyanilino)-9-(tetrahydropyran-2-yl)purine,
2-methylthio-6-(2-chloro-4-methoxyanilino)-9-(tetrahydropyran-2-yl)purine,
2-chloro-6-(2-chloro-4-methoxyanilino)-9-(tetrahydrofuran-2-yl)purine,
2-fluoro-6-(2-chloro-4-methoxyanilino)-9-(tetrahydrofuran-2-yl)purine,
2-bromo-6-(2-chloro-4-methoxyanilino)-9-(tetrahydrofuran-2-yl)purine,
2-iodo-6-(2-chloro-4-methoxyanilino)-9-(tetrahydrofuran-2-yl)purine,
2-amino-6-(2-chloro-4-methoxyanilino)-9-(tetrahydrofuran-2-yl)purine,
2-hydroxy-6-(2-chloro-4-methoxyanilino)-9-(tetrahydrofuran-2-yl)purine,
2-thio-6-(2-chloro-4-methoxyanilino)-9-(tetrahydrofuran-2-yl)purine,
2-methylthio-6-(2-chloro-4-methoxyanilino)-9-(tetrahydrofuran-2-yl)purine,
2-chloro-6-(2-chloro-5-methoxyanilino)-9-(tetrahydropyran-2-yl)purine,
2-fluoro-6-(2-chloro-5-methoxyanilino)-9-(tetrahydropyran-2-yl)purine,
2-bromo-6-(2-chloro-5-methoxyanilino)-9-(tetrahydropyran-2-yl)purine,
2-iodo-6-(2-chloro-5-methoxyanilino)-9-(tetrahydropyran-2-yl)purine,
2-amino-6-(2-chloro-5-methoxyanilino)-9-(tetrahydropyran-2-yl)purine,
2-hydroxy-6-(2-chloro-5-methoxyanilino)-9-(tetrahydropyran-2-yl)purine,
2-thio-6-(2-chloro-5-methoxyanilino)-9-(tetrahydropyran-2-yl)purine,
2-methylthio-6-(2-chloro-5-methoxyanilino)-9-(tetrahydropyran-2-yl)purine,
2-chloro-6-(2-chloro-5-methoxyanilino)-9-(tetrahydrofuran-2-yl)purine,
2-fluoro-6-(2-chloro-5-methoxyanilino)-9-(tetrahydrofuran-2-yl)purine,
2-bromo-6-(2-chloro-5-methoxyanilino)-9-(tetrahydrofuran-2-yl)purine,
2-iodo-6-(2-chloro-5-methoxyanilino)-9-(tetrahydrofuran-2-yl)purine,
2-amino-6-(2-chloro-5-methoxyanilino)-9-(tetrahydrofuran-2-yl)purine,
2-hydroxy-6-(2-chloro-5-methoxyanilino)-9-(tetrahydrofuran-2-yl)purine,
2-thio-6-(2-chloro-5-methoxyanilino)-9-(tetrahydrofuran-2-yl)purine,
2-methylthio-6-(2-chloro-5-methoxyanilino)-9-(tetrahydrofuran-2-yl)purine,
2-chloro-6-(2-chloro-3-methoxyanilino)-9-(tetrahydropyran-2-yl)purine,
2-fluoro-6-(2-chloro-3-methoxyanilino)-9-(tetrahydropyran-2-yl)purine,
2-bromo-6-(2-chloro-3-methoxyanilino)-9-(tetrahydropyran-2-yl)purine,
2-iodo-6-(2-chloro-3-methoxyanilino)-9-(tetrahydropyran-2-yl)purine,
2-amino-6-(2-chloro-3-methoxyanilino)-9-(tetrahydropyran-2-yl)purine,
2-hydroxy-6-(2-chloro-3-methoxyanilino)-9-(tetrahydropyran-2-yl)purine,
2-thio-6-(2-chloro-3-methoxyanilino)-9-(tetrahydropyran-2-yl)purine,
2-methylthio-6-(2-chloro-3-methoxyanilino)-9-(tetrahydropyran-2-yl)purine,
2-chloro-6-(2-chloro-3-methoxyanilino)-9-(tetrahydrofuran-2-yl)purine,
2-fluoro-6-(2-chloro-3-methoxyanilino)-9-(tetrahydrofuran-2-yl)purine,
2-bromo-6-(2-chloro-3-methoxyanilino)-9-(tetrahydrofuran-2-yl)purine,
2-iodo-6-(2-chloro-3-methoxyanilino)-9-(tetrahydrofuran-2-yl)purine,
2-amino-6-(2-chloro-3-methoxyanilino)-9-(tetrahydrofuran-2-yl)purine,
2-hydroxy-6-(2-chloro-3-methoxyanilino)-9-(tetrahydrofuran-2-yl)purine,
2-thio-6-(2-chloro-3-methoxyanilino)-9-(tetrahydrofuran-2-yl)purine,
2-methylthio-6-(2-chloro-3-methoxyanilino)-9-(tetrahydrofuran-2-yl)purine,
2-chloro-6-(2-bromo-3-methoxyanilino)-9-(tetrahydropyran-2-yl)purine,
2-fluoro-6-(2-bromo-3-methoxyanilino)-9-(tetrahydropyran-2-yl)purine,
2-bromo-6-(2-bromo-3-methoxyanilino)-9-(tetrahydropyran-2-yl)purine,
2-iodo-6-(2-bromo-3-methoxyanilino)-9-(tetrahydropyran-2-yl)purine, 2-amino-6-(2-bromo-3-methoxyanilino)-9-(tetrahydropyran-2-yl)purine,
2-hydroxy-6-(2-bromo-3-methoxyanilino)-9-(tetrahydropyran-2-yl)purine,
2-thio-6-(2-bromo-3-methoxyanilino)-9-(tetrahydropyran-2-yl)purine,
2-methylthio-6-(2-bromo-3-methoxyanilino)-9-(tetrahydropyran-2-yl)purine,
2-chloro-6-(2-bromo-3-methoxyanilino)-9-(tetrahydrofuran-2-yl)purine,
2-fluoro-6-(2-bromo-3-methoxyanilino)-9-(tetrahydrofuran-2-yl)purine,
2-bromo-6-(2-bromo-3-methoxyanilino)-9-(tetrahydrofuran-2-yl)purine,
2-iodo-6-(2-bromo-3-methoxyanilino)-9-(tetrahydrofuran-2-yl)purine,
2-amino-6-(2-bromo-3-methoxyanilino)-9-(tetrahydrofuran-2-yl)purine,
2-hydroxy-6-(2-bromo-3-methoxyanilino)-9-(tetrahydrofuran-2-yl)purine,
2-thio-6-(2-bromo-3-methoxyanilino)-9-(tetrahydrofuran-2-yl)purine,
2-methylthio-6-(2-bromo-3-methoxyanilino)-9-(tetrahydrofuran-2-yl)purine,
2-chloro-6-(2-methoxy-3-chloroanilino)-9-(tetrahydropyran-2-yl)purine,
2-fluoro-6-(2-methoxy-3-chloroanilino)-9-(tetrahydropyran-2-yl)purine,
2-bromo-6-(2-methoxy-3-chloroanilino)-9-(tetrahydropyran-2-yl)purine,
2-iodo-6-(2-methoxy-3-chloroanilino)-9-(tetrahydropyran-2-yl)purine,
2-amino-6-(2-methoxy-3-chloroanilino)-9-(tetrahydropyran-2-yl)purine,
2-hydroxy-6-(2-methoxy-3-chloroanilino)-9-(tetrahydropyran-2-yl)purine,
2-thio-6-(2-methoxy-3-chloroanilino)-9-(tetrahydropyran-2-yl)purine,
2-methylthio-6-(2-methoxy-3-chloroanilino)-9-(tetrahydropyran-2-yl)purine,
2-chloro-6-(2-methoxy-3-chloroanilino)-9-(tetrahydrofuran-2-yl)purine,
2-fluoro-6-(2-methoxy-3-chloroanilino)-9-(tetrahydrofuran-2-yl)purine,
2-bromo-6-(2-methoxy-3-chloroanilino)-9-(tetrahydrofuran-2-yl)purine,
2-iodo-6-(2-methoxy-3-chloroanilino)-9-(tetrahydrofuran-2-yl)purine,
2-amino-6-(2-methoxy-3-chloroanilino)-9-(tetrahydrofuran-2-yl)purine,
2-hydroxy-6-(2-methoxy-3-chloroanilino)-9-(tetrahydrofuran-2-yl)purine,
2-thio-6-(2-methoxy-3-chloroanilino)-9-(tetrahydrofuran-2-yl)purine,
2-methylthio-6-(2-methoxy-3-chloroanilino)-9-(tetrahydrofuran-2-yl)purine,
2-chloro-6-(2-methoxy-4-chloroanilino)-9-(tetrahydropyran-2-yl)purine,
2-fluoro-6-(2-methoxy-4-chloroanilino)-9-(tetrahydropyran-2-yl)purine,
2-bromo-6-(2-methoxy-4-chloroanilino)-9-(tetrahydropyran-2-yl)purine,
2-iodo-6-(2-methoxy-4-chloroanilino)-9-(tetrahydropyran-2-yl)purine,
2-amino-6-(2-methoxy-4-chloroanilino)-9-(tetrahydropyran-2-yl)purine,
2-hydroxy-6-(2-methoxy-4-chloroanilino)-9-(tetrahydropyran-2-yl)purine,
2-thio-6-(2-methoxy-4-chloroanilino)-9-(tetrahydropyran-2-yl)purine,
2-methylthio-6-(2-methoxy-4-chloroanilino)-9-(tetrahydropyran-2-yl)purine,
2-chloro-6-(2-methoxy-4-chloroanilino)-9-(tetrahydrofuran-2-yl)purine,
2-fluoro-6-(2-methoxy-4-chloroanilino)-9-(tetrahydrofuran-2-yl)purine,
2-bromo-6-(2-methoxy-4-chloroanilino)-9-(tetrahydrofuran-2-yl)purine,
2-iodo-6-(2-methoxy-4-chloroanilino)-9-(tetrahydrofuran-2-yl)purine,
2-amino-6-(2-methoxy-4-chloroanilino)-9-(tetrahydrofuran-2-yl)purine,
2-hydroxy-6-(2-methoxy-4-chloroanilino)-9-(tetrahydrofuran-2-yl)purine,
2-thio-6-(2-methoxy-4-chloroanilino)-9-(tetrahydrofuran-2-yl)purine,
2-methylthio-6-(2-methoxy-4-chloroanilino)-9-(tetrahydrofuran-2-yl)purine,
and pharmaceutically acceptable salts thereof with alkali metals, ammonium or amines.

10. The substituted 6-anilino-9-heterocyclylpurines of general formula I according to claim 9, selected from the group consisting of:
2-chloro-6-(3-methoxyanilino)-9-(tetrahydropyran-2-yl)purine,
2-fluoro-6-(3-methoxyanilino)-9-(tetrahydropyran-2-yl)purine,
2-bromo-6-(3-methoxyanilino)-9-(tetrahydropyran-2-yl)purine,
2-chloro-6-(3-methoxyanilino)-9-(tetrahydrofuran-2-yl)purine,
2-fluoro-6-(3-methoxyanilino)-9-(tetrahydrofuran-2-yl)purine,
2-bromo-6-(3-methoxyanilino)-9-(tetrahydrofuran-2-yl)purine,
2-chloro-6-(2-hydroxy-3-methoxyanilino)-9-(tetrahydropyran-2-yl)purine,
2-fluoro-6-(2-hydroxy-3-methoxy anilino)-9-(tetrahydropyran-2-yl)purine,
2-bromo-6-(2-hydroxy-3-methoxyanilino)-9-(tetrahydropyran-2-yl)purine,
2-chloro-6-(2-hydroxy-3-methoxyanilino)-9-(tetrahydrofuran-2-yl)purine,
2-fluoro-6-(2-hydroxy-3-methoxy anilino)-9-(tetrahydrofuran-2-yl)purine,
2-bromo-6-(2-hydroxy-3-methoxyanilino)-9-(tetrahydrofuran-2-yl)purine,
2-chloro-6-(2-chloro-3-methoxyanilino)-9-(tetrahydropyran-2-yl)purine,
2-fluoro-6-(2-chloro-3-methoxyanilino)-9-(tetrahydropyran-2-yl)purine,
2-bromo-6-(2-chloro-3-methoxyanilino)-9-(tetrahydropyran-2-yl)purine,
2-chloro-6-(2-chloro-3-methoxyanilino)-9-(tetrahydrofuran-2-yl)purine,
2-fluoro-6-(2-chloro-3-methoxyanilino)-9-(tetrahydrofuran-2-yl)purine,
2-bromo-6-(2-chloro-3-methoxyanilino)-9-(tetrahydrofuran-2-yl)purine,
2-chloro-6-(2-bromo-3-methoxyanilino)-9-(tetrahydropyran-2-yl)purine,
2-fluoro-6-(2-bromo-3-methoxyanilino)-9-(tetrahydropyran-2-yl)purine, 2-bromo-6-(2-bromo-3-methoxyanilino)-9-(tetrahydropyran-2-yl)purine,
2-chloro-6-(2-bromo-3-methoxyanilino)-9-(tetrahydrofuran-2-yl)purine,
2-fluoro-6-(2-bromo-3-methoxyanilino)-9-(tetrahydrofuran-2-yl)purine,
2-bromo-6-(2-bromo-3-methoxyanilino)-9-(tetrahydrofuran-2-yl)purine,
2-chloro-6-(4-hydroxyanilino)-9-(tetrahydropyran-2-yl)purine,
2-fluoro-6-(4-hydroxyanilino)-9-(tetrahydropyran-2-yl)purine,
2-bromo-6-(4-hydroxyanilino)-9-(tetrahydropyran-2-yl)purine,
2-chloro-6-(4-hydroxyanilino)-9-(tetrahydrofuran-2-yl)purine,
2-fluoro-6-(4-hydroxyanilino)-9-(tetrahydrofuran-2-yl)purine,
2-bromo-6-(4-hydroxyanilino)-9-(tetrahydrofuran-2-yl)purine,
and salts thereof with alkali metals, ammonium or amines.

* * * * *